US011981745B2

(12) United States Patent
Correnti et al.

(10) Patent No.: US 11,981,745 B2
(45) Date of Patent: May 14, 2024

(54) ANTI-MESOTHELIN ANTIGEN-BINDING MOLECULES AND USES THEREOF

(71) Applicant: Link Immunotherapeutics, Inc., Seattle, WA (US)

(72) Inventors: Colin Correnti, Seattle, WA (US); Christopher Mehlin, Seattle, WA (US); David Meininger, Seattle, WA (US); Ashok Bandaranayake, Seattle, WA (US)

(*) Notice: Subject to any disclaimer, the term of this patent is extended or adjusted under 35 U.S.C. 154(b) by 0 days.

(21) Appl. No.: 18/163,659

(22) Filed: Feb. 2, 2023

(65) Prior Publication Data

US 2023/0235091 A1  Jul. 27, 2023

Related U.S. Application Data

(63) Continuation of application No. 17/938,349, filed on Oct. 6, 2022, now abandoned.

(60) Provisional application No. 63/369,989, filed on Aug. 1, 2022, provisional application No. 63/262,156, filed on Oct. 6, 2021.

(51) Int. Cl.
| C07K 16/30 | (2006.01) |
| *A61P 35/00* | (2006.01) |
| C07K 16/28 | (2006.01) |
| C07K 16/46 | (2006.01) |
| C12N 15/63 | (2006.01) |

(52) U.S. Cl.
CPC .............. *C07K 16/30* (2013.01); *A61P 35/00* (2018.01); *C07K 16/468* (2013.01); *C12N 15/63* (2013.01); *C07K 2317/31* (2013.01); *C07K 2317/565* (2013.01); *C07K 2317/622* (2013.01)

(58) Field of Classification Search
None
See application file for complete search history.

(56) References Cited

U.S. PATENT DOCUMENTS

| 6,083,502 A | 7/2000 | Pastan et al. |
| 7,592,426 B2 | 9/2009 | Ebel et al. |
| 8,268,970 B2 | 9/2012 | Terrett et al. |
| 8,357,783 B2 | 1/2013 | Dimitrov et al. |
| 8,460,660 B2 | 6/2013 | Ho et al. |
| 8,911,732 B2 | 12/2014 | Dennis et al. |
| 9,023,351 B2 | 5/2015 | Kahnert et al. |
| 9,416,190 B2 | 8/2016 | Ho et al. |
| 9,803,022 B2 | 10/2017 | Ho et al. |
| 10,100,121 B2 | 10/2018 | Fanslow, III et al. |
| 10,793,641 B2 | 10/2020 | Wang et al. |
| 10,851,175 B2 | 12/2020 | Kim et al. |
| 2008/0261245 A1 | 10/2008 | Pastan et al. |
| 2017/0029502 A1 | 2/2017 | Raum et al. |
| 2020/0247901 A1 | 8/2020 | Pastan et al. |
| 2020/0324001 A1 | 10/2020 | Matsuura et al. |
| 2021/0238304 A1 | 8/2021 | Albone et al. |
| 2021/0309755 A1 | 10/2021 | Correnti et al. |
| 2021/0340272 A1 | 11/2021 | Zhong et al. |
| 2021/0371526 A1 | 12/2021 | Li et al. |

FOREIGN PATENT DOCUMENTS

| WO | 2017020858 A1 | 2/2017 |
| WO | 2018209304 A1 | 11/2018 |
| WO | 2020/011970 A1 | 1/2020 |
| WO | 2020257407 A1 | 12/2020 |
| WO | 2021041300 A2 | 3/2021 |
| WO | 2021207242 A2 | 10/2021 |
| WO | 2021231969 A1 | 11/2021 |
| WO | 2021239987 A1 | 12/2021 |
| WO | 2022012097 A1 | 1/2022 |
| WO | 2022030730 A1 | 2/2022 |
| WO | 2022078286 A1 | 4/2022 |
| WO | 2022121941 A1 | 6/2022 |
| WO | 2022133116 A1 | 6/2022 |
| WO | 2022177913 A1 | 8/2022 |
| WO | 2022242703 A1 | 11/2022 |
| WO | 2022256498 A1 | 12/2022 |
| WO | 2022262859 A1 | 12/2022 |
| WO | 2023277361 A1 | 1/2023 |

OTHER PUBLICATIONS

Portolano (The Journal of Immunology, vol. 150, No. 3, p. 880-887, 1993) (Year: 1993).*
Rudikoff et al. (Proceedings of the National Academy of Sciences USA, vol. 79, p. 1979-1983, 1982) (Year: 1982).*
Dubel (Handbook of Therapeutic Antibodies, 2007, p. 100-101) (Year: 2007).*
Johnson and Wu (Methods in Molecular Biology, Antibody Engineering: Methods and Protocols, vol. 248, p. 11-25, 2004) (Year: 2004).*
Paul (Fundamental Immunology, 3rd Edition, 1993, pp. 292-295) (Year: 1993).*
Bendig M. M. (Methods: A Companion to Methods in Enzymology, 1995; 8:83-93) (Year: 1995).*
Hassan et al., "Mesothelin: a new target for immunotherapy," Clin Cancer Res. 2004; 10: 3937-3942.
Ho et al., "Mesothelin is shed from tumor cells," Cancer Epidemiol Biomarkers Prev. 2006; 15(9): 1751.

(Continued)

*Primary Examiner* — Michael Allen

(57) ABSTRACT

The present disclosure provides antibodies and polypeptides that specifically bind to mesothelin (MSLN), including bispecific antibodies that bind both MSLN and a T cell antigen (e.g., CD3). Also provided are pharmaceutical compositions comprising these antibodies, nucleic acids encoding these antibodies, expression vectors and host cells for making these antibodies, and methods of treating a subject using these antibodies.

26 Claims, 12 Drawing Sheets

Specification includes a Sequence Listing.

(56) References Cited

OTHER PUBLICATIONS

PCT International Search Report and Written Opinion from PCT/US2021/026013 dated Oct. 1, 2021.

* cited by examiner

SKOV3 (Day 5)

SKOV3 (Day 5)

SEQUENCE LISTING

```
Sequence total quantity: 85
SEQ ID NO: 1              moltype = AA  length = 119
FEATURE                   Location/Qualifiers
source                    1..119
                          mol_type = protein
                          organism = synthetic construct
SEQUENCE: 1
EVQLLESGGG LVQPGGSLRL SCAASGLTFR SYAMTWVRQA PGKGLEWVSG ISVSGGITYY  60
ADSVKGRFTI SRDNSKNTLY LQMNSLRAED TAVYYCAKRG AAVGSFDYWG QGTLVTVSS  119

SEQ ID NO: 2              moltype = AA  length = 107
FEATURE                   Location/Qualifiers
source                    1..107
                          mol_type = protein
                          organism = synthetic construct
```

```
SEQUENCE: 2
DIQMTQSPSS LSASVGDRVT ITCRSSQGIG SWLAWYQQKP EKAPQSLIYA ASSLQSGVPS    60
RFSGSGSGTD FTLTISNLQP EDFATYYCQQ YNSYPLTFGG GTKVEIK                 107

SEQ ID NO: 3              moltype = AA  length = 10
FEATURE                   Location/Qualifiers
source                    1..10
                          mol_type = protein
                          organism = synthetic construct
SEQUENCE: 3
GLTFRSYAMT                                                          10

SEQ ID NO: 4              moltype = AA  length = 17
FEATURE                   Location/Qualifiers
source                    1..17
                          mol_type = protein
                          organism = synthetic construct
SEQUENCE: 4
GISVSGGITY YADSVKG                                                  17

SEQ ID NO: 5              moltype = AA  length = 10
FEATURE                   Location/Qualifiers
source                    1..10
                          mol_type = protein
                          organism = synthetic construct
SEQUENCE: 5
RGAAVGSFDY                                                          10

SEQ ID NO: 6              moltype = AA  length = 11
FEATURE                   Location/Qualifiers
source                    1..11
                          mol_type = protein
                          organism = synthetic construct
SEQUENCE: 6
RSSQGIGSWL A                                                        11

SEQ ID NO: 7              moltype = AA  length = 7
FEATURE                   Location/Qualifiers
source                    1..7
                          mol_type = protein
                          organism = synthetic construct
SEQUENCE: 7
AASSLQS                                                              7

SEQ ID NO: 8              moltype = AA  length = 9
FEATURE                   Location/Qualifiers
source                    1..9
                          mol_type = protein
                          organism = synthetic construct
SEQUENCE: 8
QQYNSYPLT                                                            9

SEQ ID NO: 9              moltype = AA  length = 449
FEATURE                   Location/Qualifiers
source                    1..449
                          mol_type = protein
                          organism = synthetic construct
SEQUENCE: 9
EVQLLESGGG LVQPGGSLRL SCAASGLTFR SYAMTWVRQA PGKGLEWVSG ISVSGGITYY    60
ADSVKGRFTI SRDNSKNTLY LQMNSLRAED TAVYYCAKRG AAVGSFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYAS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 10             moltype = AA  length = 214
FEATURE                   Location/Qualifiers
source                    1..214
                          mol_type = protein
                          organism = synthetic construct
SEQUENCE: 10
DIQMTQSPSS LSASVGDRVT ITCRSSQGIG SWLAWYQQKP EKAPQSLIYA ASSLQSGVPS    60
RFSGSGSGTD FTLTISNLQP EDFATYYCQQ YNSYPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 11             moltype = AA  length = 119
```

```
FEATURE                 Location/Qualifiers
source                  1..119
                        mol_type = protein
                        organism = synthetic construct
VARIANT                 62
                        note = D, A, S, or E
VARIANT                 63
                        note = S, T, V, or A
SEQUENCE: 11
EVQLLESGGG LVQPGGSLRL SCAASGLTFR SYAMTWVRQA PGKGLEWVSG ISVSGGITYY    60
AXXVKGRFTI SRDNSKNTLY LQMNSLRAED TAVYYCAKRG AAVGSFDYWG QGTLVTVSS    119

SEQ ID NO: 12           moltype = AA  length = 107
FEATURE                 Location/Qualifiers
source                  1..107
                        mol_type = protein
                        organism = synthetic construct
VARIANT                 92
                        note = N, A, S, or K
VARIANT                 93
                        note = S, T, V, or A
SEQUENCE: 12
DIQMTQSPSS LSASVGDRVT ITCRSSQGIG SWLAWYQQKP EKAPQSLIYA ASSLQSGVPS    60
RFSGSGSGTD FTLTISNLQP EDFATYYCQQ YXXYPLTFGG GTKVEIK                107

SEQ ID NO: 13           moltype = AA  length = 17
FEATURE                 Location/Qualifiers
source                  1..17
                        mol_type = protein
                        organism = synthetic construct
VARIANT                 13
                        note = D, A, S, or E
VARIANT                 14
                        note = S, T, V, or A
SEQUENCE: 13
GISVSGGITY YAXXVKG                                                   17

SEQ ID NO: 14           moltype = AA  length = 9
FEATURE                 Location/Qualifiers
source                  1..9
                        mol_type = protein
                        organism = synthetic construct
VARIANT                 4
                        note = N, A, S, or K
VARIANT                 5
                        note = S, T, V, or A
SEQUENCE: 14
QQYXXYPLT                                                             9

SEQ ID NO: 15           moltype = AA  length = 449
FEATURE                 Location/Qualifiers
source                  1..449
                        mol_type = protein
                        organism = synthetic construct
VARIANT                 62
                        note = D, A, S, or E
VARIANT                 63
                        note = S, T, V, or A
SEQUENCE: 15
EVQLLESGGG LVQPGGSLRL SCAASGLTFR SYAMTWVRQA PGKGLEWVSG ISVSGGITYY    60
AXXVKGRFTI SRDNSKNTLY LQMNSLRAED TAVYYCAKRG AAVGSFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYAS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 16           moltype = AA  length = 214
FEATURE                 Location/Qualifiers
source                  1..214
                        mol_type = protein
                        organism = synthetic construct
VARIANT                 92
                        note = N, A, S, or K
VARIANT                 93
                        note = S, T, V, or A
SEQUENCE: 16
DIQMTQSPSS LSASVGDRVT ITCRSSQGIG SWLAWYQQKP EKAPQSLIYA ASSLQSGVPS    60
```

```
RFSGSGSGTD FTLTISNLQP EDFATYYCQQ YXXYPLTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 17            moltype = AA   length = 119
FEATURE                  Location/Qualifiers
source                   1..119
                         mol_type = protein
                         organism = synthetic construct
SEQUENCE: 17
EVQLLESGGG LVQPGGSLRL SCAASGLTFR SYAMTWVRQA PGKGLEWVSG ISVSGGITYY    60
AESVKGRFTI SRDNSKNTLY LQMNSLRAED TAVYYCAKRG AAVGSFDYWG QGTLVTVSS     119

SEQ ID NO: 18            moltype = AA   length = 119
FEATURE                  Location/Qualifiers
source                   1..119
                         mol_type = protein
                         organism = synthetic construct
SEQUENCE: 18
EVQLLESGGG LVQPGGSLRL SCAASGLTFR SYAMTWVRQA PGKGLEWVSG ISVSGGITYY    60
ASSVKGRFTI SRDNSKNTLY LQMNSLRAED TAVYYCAKRG AAVGSFDYWG QGTLVTVSS     119

SEQ ID NO: 19            moltype = AA   length = 119
FEATURE                  Location/Qualifiers
source                   1..119
                         mol_type = protein
                         organism = synthetic construct
SEQUENCE: 19
EVQLLESGGG LVQPGGSLRL SCAASGLTFR SYAMTWVRQA PGKGLEWVSG ISVSGGITYY    60
AASVKGRFTI SRDNSKNTLY LQMNSLRAED TAVYYCAKRG AAVGSFDYWG QGTLVTVSS     119

SEQ ID NO: 20            moltype = AA   length = 119
FEATURE                  Location/Qualifiers
source                   1..119
                         mol_type = protein
                         organism = synthetic construct
SEQUENCE: 20
EVQLLESGGG LVQPGGSLRL SCAASGLTFR SYAMTWVRQA PGKGLEWVSG ISVSGGITYY    60
ADTVKGRFTI SRDNSKNTLY LQMNSLRAED TAVYYCAKRG AAVGSFDYWG QGTLVTVSS     119

SEQ ID NO: 21            moltype = AA   length = 119
FEATURE                  Location/Qualifiers
source                   1..119
                         mol_type = protein
                         organism = synthetic construct
SEQUENCE: 21
EVQLLESGGG LVQPGGSLRL SCAASGLTFR SYAMTWVRQA PGKGLEWVSG ISVSGGITYY    60
ADVVKGRFTI SRDNSKNTLY LQMNSLRAED TAVYYCAKRG AAVGSFDYWG QGTLVTVSS     119

SEQ ID NO: 22            moltype = AA   length = 119
FEATURE                  Location/Qualifiers
source                   1..119
                         mol_type = protein
                         organism = synthetic construct
SEQUENCE: 22
EVQLLESGGG LVQPGGSLRL SCAASGLTFR SYAMTWVRQA PGKGLEWVSG ISVSGGITYY    60
ADAVKGRFTI SRDNSKNTLY LQMNSLRAED TAVYYCAKRG AAVGSFDYWG QGTLVTVSS     119

SEQ ID NO: 23            moltype = AA   length = 107
FEATURE                  Location/Qualifiers
source                   1..107
                         mol_type = protein
                         organism = synthetic construct
SEQUENCE: 23
DIQMTQSPSS LSASVGDRVT ITCRSSQGIG SWLAWYQQKP EKAPQSLIYA ASSLQSGVPS    60
RFSGSGSGTD FTLTISNLQP EDFATYYCQQ YKSYPLTFGG GTKVEIK                  107

SEQ ID NO: 24            moltype = AA   length = 107
FEATURE                  Location/Qualifiers
source                   1..107
                         mol_type = protein
                         organism = synthetic construct
SEQUENCE: 24
DIQMTQSPSS LSASVGDRVT ITCRSSQGIG SWLAWYQQKP EKAPQSLIYA ASSLQSGVPS    60
RFSGSGSGTD FTLTISNLQP EDFATYYCQQ YSSYPLTFGG GTKVEIK                  107

SEQ ID NO: 25            moltype = AA   length = 107
FEATURE                  Location/Qualifiers
source                   1..107
```

```
                            mol_type = protein
                            organism = synthetic construct
SEQUENCE: 25
DIQMTQSPSS LSASVGDRVT ITCRSSQGIG SWLAWYQQKP EKAPQSLIYA ASSLQSGVPS    60
RFSGSGSGTD FTLTISNLQP EDFATYYCQQ YASYPLTFGG GTKVEIK                 107

SEQ ID NO: 26           moltype = AA   length = 107
FEATURE                 Location/Qualifiers
source                  1..107
                        mol_type = protein
                        organism = synthetic construct
SEQUENCE: 26
DIQMTQSPSS LSASVGDRVT ITCRSSQGIG SWLAWYQQKP EKAPQSLIYA ASSLQSGVPS    60
RFSGSGSGTD FTLTISNLQP EDFATYYCQQ YNTYPLTFGG GTKVEIK                 107

SEQ ID NO: 27           moltype = AA   length = 107
FEATURE                 Location/Qualifiers
source                  1..107
                        mol_type = protein
                        organism = synthetic construct
SEQUENCE: 27
DIQMTQSPSS LSASVGDRVT ITCRSSQGIG SWLAWYQQKP EKAPQSLIYA ASSLQSGVPS    60
RFSGSGSGTD FTLTISNLQP EDFATYYCQQ YNVYPLTFGG GTKVEIK                 107

SEQ ID NO: 28           moltype = AA   length = 107
FEATURE                 Location/Qualifiers
source                  1..107
                        mol_type = protein
                        organism = synthetic construct
SEQUENCE: 28
DIQMTQSPSS LSASVGDRVT ITCRSSQGIG SWLAWYQQKP EKAPQSLIYA ASSLQSGVPS    60
RFSGSGSGTD FTLTISNLQP EDFATYYCQQ YNAYPLTFGG GTKVEIK                 107

SEQ ID NO: 29           moltype = AA   length = 17
FEATURE                 Location/Qualifiers
source                  1..17
                        mol_type = protein
                        organism = synthetic construct
SEQUENCE: 29
GISVSGGITY YAESVKG                                                   17

SEQ ID NO: 30           moltype = AA   length = 17
FEATURE                 Location/Qualifiers
source                  1..17
                        mol_type = protein
                        organism = synthetic construct
SEQUENCE: 30
GISVSGGITY YASSVKG                                                   17

SEQ ID NO: 31           moltype = AA   length = 17
FEATURE                 Location/Qualifiers
source                  1..17
                        mol_type = protein
                        organism = synthetic construct
SEQUENCE: 31
GISVSGGITY YAASVKG                                                   17

SEQ ID NO: 32           moltype = AA   length = 17
FEATURE                 Location/Qualifiers
source                  1..17
                        mol_type = protein
                        organism = synthetic construct
SEQUENCE: 32
GISVSGGITY YADTVKG                                                   17

SEQ ID NO: 33           moltype = AA   length = 17
FEATURE                 Location/Qualifiers
source                  1..17
                        mol_type = protein
                        organism = synthetic construct
SEQUENCE: 33
GISVSGGITY YADVVKG                                                   17

SEQ ID NO: 34           moltype = AA   length = 17
FEATURE                 Location/Qualifiers
source                  1..17
                        mol_type = protein
                        organism = synthetic construct
SEQUENCE: 34
```

-continued

```
GISVSGGITY YADAVKG                                                          17

SEQ ID NO: 35           moltype = AA  length = 9
FEATURE                 Location/Qualifiers
source                  1..9
                        mol_type = protein
                        organism = synthetic construct
SEQUENCE: 35
QQYKSYPLT                                                                    9

SEQ ID NO: 36           moltype = AA  length = 9
FEATURE                 Location/Qualifiers
source                  1..9
                        mol_type = protein
                        organism = synthetic construct
SEQUENCE: 36
QQYSSYPLT                                                                    9

SEQ ID NO: 37           moltype = AA  length = 9
FEATURE                 Location/Qualifiers
source                  1..9
                        mol_type = protein
                        organism = synthetic construct
SEQUENCE: 37
QQYASYPLT                                                                    9

SEQ ID NO: 38           moltype = AA  length = 9
FEATURE                 Location/Qualifiers
source                  1..9
                        mol_type = protein
                        organism = synthetic construct
SEQUENCE: 38
QQYNTYPLT                                                                    9

SEQ ID NO: 39           moltype = AA  length = 9
FEATURE                 Location/Qualifiers
source                  1..9
                        mol_type = protein
                        organism = synthetic construct
SEQUENCE: 39
QQYNVYPLT                                                                    9

SEQ ID NO: 40           moltype = AA  length = 9
FEATURE                 Location/Qualifiers
source                  1..9
                        mol_type = protein
                        organism = synthetic construct
SEQUENCE: 40
QQYNAYPLT                                                                    9

SEQ ID NO: 41           moltype = AA  length = 449
FEATURE                 Location/Qualifiers
source                  1..449
                        mol_type = protein
                        organism = synthetic construct
SEQUENCE: 41
EVQLLESGGG LVQPGGSLRL SCAASGLTFR SYAMTWVRQA PGKGLEWVSG ISVSGGITYY            60
AESVKGRFTI SRDNSKNTLY LQMNSLRAED TAVYYCAKRG AAVGSFDYWG QGTLVTVSSA           120
STKGPSVFPL APSSKSTSGG TAALGCLVKD YFPEPVTVSW NSGALTSGVH TFPAVLQSSG           180
LYSLSSVVTV PSSSLGTQTY ICNVNHKPSN TKVDKKVEPK SCDKTHTCPP CPAPELLGGP           240
SVFLFPPKPK DTLMISRTPE VTCVVVDVSH EDPEVKFNWY VDGVEVHNAK TKPREEQYAS           300
TYRVVSVLTV LHQDWLNGKE YKCKVSNKAL PAPIEKTISK AKGQPREPQV YTLPPSRDEL           360
TKNQVSLTCL VKGFYPSDIA VEWESNGQPE NNYKTTPPVL DSDGSFFLYS KLTVDKSRWQ           420
QGNVFSCSVM HEALHNHYTQ KSLSLSPGK                                            449

SEQ ID NO: 42           moltype = AA  length = 449
FEATURE                 Location/Qualifiers
source                  1..449
                        mol_type = protein
                        organism = synthetic construct
SEQUENCE: 42
EVQLLESGGG LVQPGGSLRL SCAASGLTFR SYAMTWVRQA PGKGLEWVSG ISVSGGITYY            60
ASSVKGRFTI SRDNSKNTLY LQMNSLRAED TAVYYCAKRG AAVGSFDYWG QGTLVTVSSA           120
STKGPSVFPL APSSKSTSGG TAALGCLVKD YFPEPVTVSW NSGALTSGVH TFPAVLQSSG           180
LYSLSSVVTV PSSSLGTQTY ICNVNHKPSN TKVDKKVEPK SCDKTHTCPP CPAPELLGGP           240
SVFLFPPKPK DTLMISRTPE VTCVVVDVSH EDPEVKFNWY VDGVEVHNAK TKPREEQYAS           300
TYRVVSVLTV LHQDWLNGKE YKCKVSNKAL PAPIEKTISK AKGQPREPQV YTLPPSRDEL           360
TKNQVSLTCL VKGFYPSDIA VEWESNGQPE NNYKTTPPVL DSDGSFFLYS KLTVDKSRWQ           420
QGNVFSCSVM HEALHNHYTQ KSLSLSPGK                                            449
```

```
SEQ ID NO: 43            moltype = AA  length = 449
FEATURE                  Location/Qualifiers
source                   1..449
                         mol_type = protein
                         organism = synthetic construct
SEQUENCE: 43
EVQLLESGGG LVQPGGSLRL SCAASGLTFR SYAMTWVRQA PGKGLEWVSG ISVSGGITYY  60
AASVKGRFTI SRDNSKNTLY LQMNSLRAED TAVYYCAKRG AAVGSFDYWG QGTLVTVSSA 120
STKGPSVFPL APSSKSTSGG TAALGCLVKD YFPEPVTVSW NSGALTSGVH TFPAVLQSSG 180
LYSLSSVVTV PSSSLGTQTY ICNVNHKPSN TKVDKKVEPK SCDKTHTCPP CPAPELLGGP 240
SVFLFPPKPK DTLMISRTPE VTCVVVDVSH EDPEVKFNWY VDGVEVHNAK TKPREEQYAS 300
TYRVVSVLTV LHQDWLNGKE YKCKVSNKAL PAPIEKTISK AKGQPREPQV YTLPPSRDEL 360
TKNQVSLTCL VKGFYPSDIA VEWESNGQPE NNYKTTPPVL DSDGSFFLYS KLTVDKSRWQ 420
QGNVFSCSVM HEALHNHYTQ KSLSLSPGK                                  449

SEQ ID NO: 44            moltype = AA  length = 449
FEATURE                  Location/Qualifiers
source                   1..449
                         mol_type = protein
                         organism = synthetic construct
SEQUENCE: 44
EVQLLESGGG LVQPGGSLRL SCAASGLTFR SYAMTWVRQA PGKGLEWVSG ISVSGGITYY  60
ADTVKGRFTI SRDNSKNTLY LQMNSLRAED TAVYYCAKRG AAVGSFDYWG QGTLVTVSSA 120
STKGPSVFPL APSSKSTSGG TAALGCLVKD YFPEPVTVSW NSGALTSGVH TFPAVLQSSG 180
LYSLSSVVTV PSSSLGTQTY ICNVNHKPSN TKVDKKVEPK SCDKTHTCPP CPAPELLGGP 240
SVFLFPPKPK DTLMISRTPE VTCVVVDVSH EDPEVKFNWY VDGVEVHNAK TKPREEQYAS 300
TYRVVSVLTV LHQDWLNGKE YKCKVSNKAL PAPIEKTISK AKGQPREPQV YTLPPSRDEL 360
TKNQVSLTCL VKGFYPSDIA VEWESNGQPE NNYKTTPPVL DSDGSFFLYS KLTVDKSRWQ 420
QGNVFSCSVM HEALHNHYTQ KSLSLSPGK                                  449

SEQ ID NO: 45            moltype = AA  length = 449
FEATURE                  Location/Qualifiers
source                   1..449
                         mol_type = protein
                         organism = synthetic construct
SEQUENCE: 45
EVQLLESGGG LVQPGGSLRL SCAASGLTFR SYAMTWVRQA PGKGLEWVSG ISVSGGITYY  60
ADVVKGRFTI SRDNSKNTLY LQMNSLRAED TAVYYCAKRG AAVGSFDYWG QGTLVTVSSA 120
STKGPSVFPL APSSKSTSGG TAALGCLVKD YFPEPVTVSW NSGALTSGVH TFPAVLQSSG 180
LYSLSSVVTV PSSSLGTQTY ICNVNHKPSN TKVDKKVEPK SCDKTHTCPP CPAPELLGGP 240
SVFLFPPKPK DTLMISRTPE VTCVVVDVSH EDPEVKFNWY VDGVEVHNAK TKPREEQYAS 300
TYRVVSVLTV LHQDWLNGKE YKCKVSNKAL PAPIEKTISK AKGQPREPQV YTLPPSRDEL 360
TKNQVSLTCL VKGFYPSDIA VEWESNGQPE NNYKTTPPVL DSDGSFFLYS KLTVDKSRWQ 420
QGNVFSCSVM HEALHNHYTQ KSLSLSPGK                                  449

SEQ ID NO: 46            moltype = AA  length = 449
FEATURE                  Location/Qualifiers
source                   1..449
                         mol_type = protein
                         organism = synthetic construct
SEQUENCE: 46
EVQLLESGGG LVQPGGSLRL SCAASGLTFR SYAMTWVRQA PGKGLEWVSG ISVSGGITYY  60
ADAVKGRFTI SRDNSKNTLY LQMNSLRAED TAVYYCAKRG AAVGSFDYWG QGTLVTVSSA 120
STKGPSVFPL APSSKSTSGG TAALGCLVKD YFPEPVTVSW NSGALTSGVH TFPAVLQSSG 180
LYSLSSVVTV PSSSLGTQTY ICNVNHKPSN TKVDKKVEPK SCDKTHTCPP CPAPELLGGP 240
SVFLFPPKPK DTLMISRTPE VTCVVVDVSH EDPEVKFNWY VDGVEVHNAK TKPREEQYAS 300
TYRVVSVLTV LHQDWLNGKE YKCKVSNKAL PAPIEKTISK AKGQPREPQV YTLPPSRDEL 360
TKNQVSLTCL VKGFYPSDIA VEWESNGQPE NNYKTTPPVL DSDGSFFLYS KLTVDKSRWQ 420
QGNVFSCSVM HEALHNHYTQ KSLSLSPGK                                  449

SEQ ID NO: 47            moltype = AA  length = 214
FEATURE                  Location/Qualifiers
source                   1..214
                         mol_type = protein
                         organism = synthetic construct
SEQUENCE: 47
DIQMTQSPSS LSASVGDRVT ITCRSSQGIG SWLAWYQQKP EKAPQSLIYA ASSLQSGVPS  60
RFSGSGSGTD FTLTISNLQP EDFATYYCQQ YKSYPLTFGG GTKVEIKRTV AAPSVFIFPP 120
SDEQLKSGTA SVVCLLNNFY PREAKVQWKV DNALQSGNSQ ESVTEQDSKD STYSLSSTLT 180
LSKADYEKHK VYACEVTHQG LSSPVTKSFN RGEC                            214

SEQ ID NO: 48            moltype = AA  length = 214
FEATURE                  Location/Qualifiers
source                   1..214
                         mol_type = protein
                         organism = synthetic construct
SEQUENCE: 48
DIQMTQSPSS LSASVGDRVT ITCRSSQGIG SWLAWYQQKP EKAPQSLIYA ASSLQSGVPS  60
```

```
RFSGSGSGTD FTLTISNLQP EDFATYYCQQ YSSYPLTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 49           moltype = AA   length = 214
FEATURE                 Location/Qualifiers
source                  1..214
                        mol_type = protein
                        organism = synthetic construct
SEQUENCE: 49
DIQMTQSPSS LSASVGDRVT ITCRSSQGIG SWLAWYQQKP EKAPQSLIYA ASSLQSGVPS    60
RFSGSGSGTD FTLTISNLQP EDFATYYCQQ YASYPLTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 50           moltype = AA   length = 214
FEATURE                 Location/Qualifiers
source                  1..214
                        mol_type = protein
                        organism = synthetic construct
SEQUENCE: 50
DIQMTQSPSS LSASVGDRVT ITCRSSQGIG SWLAWYQQKP EKAPQSLIYA ASSLQSGVPS    60
RFSGSGSGTD FTLTISNLQP EDFATYYCQQ YNTYPLTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 51           moltype = AA   length = 214
FEATURE                 Location/Qualifiers
source                  1..214
                        mol_type = protein
                        organism = synthetic construct
SEQUENCE: 51
DIQMTQSPSS LSASVGDRVT ITCRSSQGIG SWLAWYQQKP EKAPQSLIYA ASSLQSGVPS    60
RFSGSGSGTD FTLTISNLQP EDFATYYCQQ YNVYPLTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 52           moltype = AA   length = 214
FEATURE                 Location/Qualifiers
source                  1..214
                        mol_type = protein
                        organism = synthetic construct
SEQUENCE: 52
DIQMTQSPSS LSASVGDRVT ITCRSSQGIG SWLAWYQQKP EKAPQSLIYA ASSLQSGVPS    60
RFSGSGSGTD FTLTISNLQP EDFATYYCQQ YNAYPLTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 53           moltype = AA   length = 329
FEATURE                 Location/Qualifiers
source                  1..329
                        mol_type = protein
                        organism = Homo sapiens
SEQUENCE: 53
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                      329

SEQ ID NO: 54           moltype = AA   length = 329
FEATURE                 Location/Qualifiers
source                  1..329
                        mol_type = protein
                        organism = synthetic construct
SEQUENCE: 54
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYA    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                      329

SEQ ID NO: 55           moltype = AA   length = 329
FEATURE                 Location/Qualifiers
source                  1..329
                        mol_type = protein
                        organism = synthetic construct
```

-continued

```
SEQUENCE: 55
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELEGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LGAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 56           moltype = AA  length = 325
FEATURE                 Location/Qualifiers
source                  1..325
                        mol_type = protein
                        organism = synthetic construct
SEQUENCE: 56
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPPCP APPVAGPSVF   120
LFPPKPKDTL MISRTPEVTC VVVDVSHEDP EVQFNWYVDG VEVHNAKTKP REEQFASTFR   180
VVSVLTVVHQ DWLNGKEYKC KVSNKGLPAP IEKTISKTKG QPREPQVYTL PPSREEMTKN   240
QVSLTCLVKG FYPSDIAVEW ESNGQPENNY KTTPPMLDSD GSFFLYSKLT VDKSRWQQGN   300
VFSCSVMHEA LHNHYTQKSL SLSPG                                        325

SEQ ID NO: 57           moltype = AA  length = 125
FEATURE                 Location/Qualifiers
source                  1..125
                        mol_type = protein
                        organism = synthetic construct
SEQUENCE: 57
EVQLVESGGG LVQPGGSLKL SCAASGFTFN TYAMNWVRQA PGKGLEWVAR IRSKYNNYAT    60
YYADSVKDRF TISRDDSKNT AYLQMNNLKT EDTAVYYCVR HGNFGNSYVS WFAYWGQGTL   120
VTVSS                                                              125

SEQ ID NO: 58           moltype = AA  length = 109
FEATURE                 Location/Qualifiers
source                  1..109
                        mol_type = protein
                        organism = synthetic construct
SEQUENCE: 58
QTVVTQEPSL TVSPGGTVTL TCRSSTGAVT TSNYANWVQQ KPGQAPRGLI GGTNKRAPGT    60
PARFSGSLLG GKAALTLSGV QPEDEAEYYC ALWYSNLWVF GGGTKLTVL               109

SEQ ID NO: 59           moltype = AA  length = 119
FEATURE                 Location/Qualifiers
source                  1..119
                        mol_type = protein
                        organism = synthetic construct
SEQUENCE: 59
QVQLVQSGGG VVQPGRSLRL SCKASGYTFT RYTMHWVRQA PGKGLEWIGY INPSRGYTNY    60
NQKFKDRFTI SRDNSKNTAF LQMDSLRPED TGVYFCARYY DDHYSLDYWG QGTPVTVSS    119

SEQ ID NO: 60           moltype = AA  length = 107
FEATURE                 Location/Qualifiers
source                  1..107
                        mol_type = protein
                        organism = synthetic construct
SEQUENCE: 60
DIQMTQSPSS LSASVGDRVT ITCSASSSVS YMNWYQQTPG KAPKRWIYDT SKLASGVPSR    60
FSGSGSGTDY TFTISSLQPE DIATYYCQQW SSNPFTFGQG TKLQITR                 107

SEQ ID NO: 61           moltype = AA  length = 122
FEATURE                 Location/Qualifiers
source                  1..122
                        mol_type = protein
                        organism = synthetic construct
SEQUENCE: 61
EVQLVESGGG LVQPGGSLRL SCAASGYSFT GYTMNWVRQA PGKGLEWVAL INPYKGVTTY    60
ADSVKGRFTI SVDKSKNTAY LQMNSLRAED TAVYYCARSG YYGDSDWYFD VWGQGTLVTV   120
SS                                                                 122

SEQ ID NO: 62           moltype = AA  length = 107
FEATURE                 Location/Qualifiers
source                  1..107
                        mol_type = protein
                        organism = synthetic construct
SEQUENCE: 62
DIQMTQSPSS LSASVGDRVT ITCRASQDIR NYLNWYQQKP GKAPKLLIYY TSRLESGVPS    60
RFSGSGSGTD YTLTISSLQP EDFATYYCQQ GNTLPWTFGQ GTKVEIK                 107

SEQ ID NO: 63           moltype = AA  length = 4
FEATURE                 Location/Qualifiers
```

```
source          1..4
                mol_type = protein
                organism = synthetic construct
REPEAT          1..4
                note = 1, 2, 3, or 4
SEQUENCE: 63
GGGS                                                                    4

SEQ ID NO: 64   moltype = AA  length = 5
FEATURE         Location/Qualifiers
source          1..5
                mol_type = protein
                organism = synthetic construct
REPEAT          1..5
                note = 1, 2, 3, or 4
SEQUENCE: 64
GGGGS                                                                   5

SEQ ID NO: 65   moltype = AA  length = 448
FEATURE         Location/Qualifiers
source          1..448
                mol_type = protein
                organism = synthetic construct
VARIANT         62
                note = D, A, S, or E
VARIANT         63
                note = S, T, V, or A
SEQUENCE: 65
EVQLLESGGG LVQPGGSLRL SCAASGLTFR SYAMTWVRQA PGKGLEWVSG ISVSGGITYY    60
AXXVKGRFTI SRDNSKNTLY LQMNSLRAED TAVYYCAKRG AAVGSFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYAS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                      448

SEQ ID NO: 66   moltype = AA  length = 448
FEATURE         Location/Qualifiers
source          1..448
                mol_type = protein
                organism = synthetic construct
SEQUENCE: 66
EVQLLESGGG LVQPGGSLRL SCAASGLTFR SYAMTWVRQA PGKGLEWVSG ISVSGGITYY    60
AESVKGRFTI SRDNSKNTLY LQMNSLRAED TAVYYCAKRG AAVGSFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYAS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                      448

SEQ ID NO: 67   moltype = AA  length = 448
FEATURE         Location/Qualifiers
source          1..448
                mol_type = protein
                organism = synthetic construct
SEQUENCE: 67
EVQLLESGGG LVQPGGSLRL SCAASGLTFR SYAMTWVRQA PGKGLEWVSG ISVSGGITYY    60
ASSVKGRFTI SRDNSKNTLY LQMNSLRAED TAVYYCAKRG AAVGSFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYAS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                      448

SEQ ID NO: 68   moltype = AA  length = 448
FEATURE         Location/Qualifiers
source          1..448
                mol_type = protein
                organism = synthetic construct
SEQUENCE: 68
EVQLLESGGG LVQPGGSLRL SCAASGLTFR SYAMTWVRQA PGKGLEWVSG ISVSGGITYY    60
ASSVKGRFTI SRDNSKNTLY LQMNSLRAED TAVYYCAKRG AAVGSFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYAS   300
TYRVVSVLTV LHQDWLNGKE YKCKVSNKAL PAPIEKTISK AKGQPREPQV YTLPPSRDEL   360
```

```
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPG                                      448

SEQ ID NO: 69           moltype = AA  length = 448
FEATURE                 Location/Qualifiers
source                  1..448
                        mol_type = protein
                        organism = synthetic construct
SEQUENCE: 69
EVQLLESGGG LVQPGGSLRL SCAASGLTFR SYAMTWVRQA PGKGLEWVSG ISVSGGITYY    60
ADTVKGRFTI SRDNSKNTLY LQMNSLRAED TAVYYCAKRG AAVGSFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYAS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 70           moltype = AA  length = 448
FEATURE                 Location/Qualifiers
source                  1..448
                        mol_type = protein
                        organism = synthetic construct
SEQUENCE: 70
EVQLLESGGG LVQPGGSLRL SCAASGLTFR SYAMTWVRQA PGKGLEWVSG ISVSGGITYY    60
ADVVKGRFTI SRDNSKNTLY LQMNSLRAED TAVYYCAKRG AAVGSFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYAS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 71           moltype = AA  length = 448
FEATURE                 Location/Qualifiers
source                  1..448
                        mol_type = protein
                        organism = synthetic construct
SEQUENCE: 71
EVQLLESGGG LVQPGGSLRL SCAASGLTFR SYAMTWVRQA PGKGLEWVSG ISVSGGITYY    60
ADAVKGRFTI SRDNSKNTLY LQMNSLRAED TAVYYCAKRG AAVGSFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYAS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 72           moltype = AA  length = 329
FEATURE                 Location/Qualifiers
source                  1..329
                        mol_type = protein
                        organism = synthetic construct
SEQUENCE: 72
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELEGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPSSIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 73           moltype = AA  length = 17
FEATURE                 Location/Qualifiers
source                  1..17
                        mol_type = protein
                        organism = synthetic construct
SEQUENCE: 73
GGGGSGGGSG GGSGGGG                                                  17

SEQ ID NO: 74           moltype = AA  length = 17
FEATURE                 Location/Qualifiers
source                  1..17
                        mol_type = protein
                        organism = synthetic construct
SEQUENCE: 74
GGGSGGGGSG GGGSGGG                                                  17

SEQ ID NO: 75           moltype = AA  length = 13
FEATURE                 Location/Qualifiers
```

```
source                  1..13
                        mol_type = protein
                        organism = synthetic construct
SEQUENCE: 75
GGGGSGGGSG GGG                                                              13

SEQ ID NO: 76           moltype = AA  length = 251
FEATURE                 Location/Qualifiers
source                  1..251
                        mol_type = protein
                        organism = synthetic construct
SEQUENCE: 76
EVQLVESGGG LVQPGGSLKL SCAASGFTFN TYAMNWVRQA PGKGLEWVAR IRSKYNNYAT           60
YYADSVKDRF TISRDDSKNT AYLQMNNLKT EDTAVYYCVR HGNFGNSYVS WFAYWGQGTL          120
VTVSSGGGGS GGGGSGGGSG GGGQTVVTQEP SLTVSPGGTV TLTCRSSTGA VTTSNYANWV         180
QQKPGQAPRG LIGGTNKRAP GTPARFSGSL LGGKAALTLS GVQPEDEAEY YCALWYSNLW          240
VFGGGTKLTV L                                                              251

SEQ ID NO: 77           moltype = AA  length = 482
FEATURE                 Location/Qualifiers
source                  1..482
                        mol_type = protein
                        organism = synthetic construct
SEQUENCE: 77
DIQMTQSPSS LSASVGDRVT ITCRSSQGIG SWLAWYQQKP EKAPQSLIYA ASSLQSGVPS           60
RFSGSGSGTD FTLTISNLQP EDFATYYCQQ YKSYPLTFGG GTKVEIKRTV AAPSVFIFPP         120
SDEQLKSGTA SVVCLLNNFY PREAKVQWKV DNALQSGNSQ ESVTEQDSKD STYSLSSTLT         180
LSKADYEKHK VYACEVTHQG LSSPVTKSFN RGECGGGGSG GGSGGGGSGG GEVQLVESGG         240
GLVQPGGSLK LSCAASGFTF NTYAMNWVRQ APGKGLEWVA RIRSKYNNYA TYYADSVKDR         300
FTISRDDSKN TAYLQMNNLK TEDTAVYYCV RHGNFGNSYV SWFAYWGQGT LVTVSSGGGG         360
SGGGSGGGSG GGGQTVVTQE PSLTVSPGGT VTLTCRSSTG AVTTSNYANW VQQKPGQAPR         420
GLIGGTNKRA PGTPARFSGS LLGGKAALTL SGVQPEDEAE YYCALWYSNL WVFGGGTKLT         480
VL                                                                        482

SEQ ID NO: 78           moltype = AA  length = 482
FEATURE                 Location/Qualifiers
source                  1..482
                        mol_type = protein
                        organism = synthetic construct
SEQUENCE: 78
DIQMTQSPSS LSASVGDRVT ITCRSSQGIG SWLAWYQQKP EKAPQSLIYA ASSLQSGVPS           60
RFSGSGSGTD FTLTISNLQP EDFATYYCQQ YSSYPLTFGG GTKVEIKRTV AAPSVFIFPP         120
SDEQLKSGTA SVVCLLNNFY PREAKVQWKV DNALQSGNSQ ESVTEQDSKD STYSLSSTLT         180
LSKADYEKHK VYACEVTHQG LSSPVTKSFN RGECGGGGSG GGSGGGGSGG GEVQLVESGG         240
GLVQPGGSLK LSCAASGFTF NTYAMNWVRQ APGKGLEWVA RIRSKYNNYA TYYADSVKDR         300
FTISRDDSKN TAYLQMNNLK TEDTAVYYCV RHGNFGNSYV SWFAYWGQGT LVTVSSGGGG         360
SGGGSGGGSG GGGQTVVTQE PSLTVSPGGT VTLTCRSSTG AVTTSNYANW VQQKPGQAPR         420
GLIGGTNKRA PGTPARFSGS LLGGKAALTL SGVQPEDEAE YYCALWYSNL WVFGGGTKLT         480
VL                                                                        482

SEQ ID NO: 79           moltype = AA  length = 482
FEATURE                 Location/Qualifiers
source                  1..482
                        mol_type = protein
                        organism = synthetic construct
SEQUENCE: 79
DIQMTQSPSS LSASVGDRVT ITCRSSQGIG SWLAWYQQKP EKAPQSLIYA ASSLQSGVPS           60
RFSGSGSGTD FTLTISNLQP EDFATYYCQQ YASYPLTFGG GTKVEIKRTV AAPSVFIFPP         120
SDEQLKSGTA SVVCLLNNFY PREAKVQWKV DNALQSGNSQ ESVTEQDSKD STYSLSSTLT         180
LSKADYEKHK VYACEVTHQG LSSPVTKSFN RGECGGGGSG GGSGGGGSGG GEVQLVESGG         240
GLVQPGGSLK LSCAASGFTF NTYAMNWVRQ APGKGLEWVA RIRSKYNNYA TYYADSVKDR         300
FTISRDDSKN TAYLQMNNLK TEDTAVYYCV RHGNFGNSYV SWFAYWGQGT LVTVSSGGGG         360
SGGGSGGGSG GGGQTVVTQE PSLTVSPGGT VTLTCRSSTG AVTTSNYANW VQQKPGQAPR         420
GLIGGTNKRA PGTPARFSGS LLGGKAALTL SGVQPEDEAE YYCALWYSNL WVFGGGTKLT         480
VL                                                                        482

SEQ ID NO: 80           moltype = AA  length = 482
FEATURE                 Location/Qualifiers
source                  1..482
                        mol_type = protein
                        organism = synthetic construct
SEQUENCE: 80
DIQMTQSPSS LSASVGDRVT ITCRSSQGIG SWLAWYQQKP EKAPQSLIYA ASSLQSGVPS           60
RFSGSGSGTD FTLTISNLQP EDFATYYCQQ YNTYPLTFGG GTKVEIKRTV AAPSVFIFPP         120
SDEQLKSGTA SVVCLLNNFY PREAKVQWKV DNALQSGNSQ ESVTEQDSKD STYSLSSTLT         180
LSKADYEKHK VYACEVTHQG LSSPVTKSFN RGECGGGGSG GGSGGGGSGG GEVQLVESGG         240
GLVQPGGSLK LSCAASGFTF NTYAMNWVRQ APGKGLEWVA RIRSKYNNYA TYYADSVKDR         300
FTISRDDSKN TAYLQMNNLK TEDTAVYYCV RHGNFGNSYV SWFAYWGQGT LVTVSSGGGG         360
SGGGSGGGSG GGGQTVVTQE PSLTVSPGGT VTLTCRSSTG AVTTSNYANW VQQKPGQAPR         420
```

```
GLIGGTNKRA PGTPARFSGS LLGGKAALTL SGVQPEDEAE YYCALWYSNL WVFGGGTKLT    480
VL                                                                  482

SEQ ID NO: 81            moltype = AA   length = 482
FEATURE                  Location/Qualifiers
source                   1..482
                         mol_type = protein
                         organism = synthetic construct
SEQUENCE: 81
DIQMTQSPSS LSASVGDRVT ITCRSSQGIG SWLAWYQQKP EKAPQSLIYA ASSLQSGVPS    60
RFSGSGSGTD FTLTISNLQP EDFATYYCQQ YNVYPLTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGECGGGGSG GGSGGGSGGG GEVQLVESGG    240
GLVQPGGSLK LSCAASGFTF NTYAMNWVRQ APGKGLEWVA RIRSKYNNYA TYYADSVKDR    300
FTISRDDSKN TAYLQMNNLK TEDTAVYYCV RHGNFGNSYV SWFAYWGQGT LVTVSSGGGG    360
SGGGGSGGGS GGGGQTVVTQE PSLTVSPGGT VTLTCRSSTG AVTTSNYANW VQQKPGQAPR    420
GLIGGTNKRA PGTPARFSGS LLGGKAALTL SGVQPEDEAE YYCALWYSNL WVFGGGTKLT    480
VL                                                                  482

SEQ ID NO: 82            moltype = AA   length = 482
FEATURE                  Location/Qualifiers
source                   1..482
                         mol_type = protein
                         organism = synthetic construct
SEQUENCE: 82
DIQMTQSPSS LSASVGDRVT ITCRSSQGIG SWLAWYQQKP EKAPQSLIYA ASSLQSGVPS    60
RFSGSGSGTD FTLTISNLQP EDFATYYCQQ YNAYPLTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGECGGGGSG GGSGGGSGGG GEVQLVESGG    240
GLVQPGGSLK LSCAASGFTF NTYAMNWVRQ APGKGLEWVA RIRSKYNNYA TYYADSVKDR    300
FTISRDDSKN TAYLQMNNLK TEDTAVYYCV RHGNFGNSYV SWFAYWGQGT LVTVSSGGGG    360
SGGGGSGGGS GGGGQTVVTQE PSLTVSPGGT VTLTCRSSTG AVTTSNYANW VQQKPGQAPR    420
GLIGGTNKRA PGTPARFSGS LLGGKAALTL SGVQPEDEAE YYCALWYSNL WVFGGGTKLT    480
VL                                                                  482

SEQ ID NO: 83            moltype = AA   length = 449
FEATURE                  Location/Qualifiers
source                   1..449
                         mol_type = protein
                         organism = synthetic construct
SEQUENCE: 83
EVQLLESGGG LVQPGGSLRL SCAASGLTFR SYAMTWVRQA PGKGLEWVSG ISVSGGITYY    60
ASSVKGRFTI SRDNSKNTLY LQMNSLRAED TAVYYCAKRG AAVGSFDYWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELEGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL GAPIEKTISK AKGQPREPQV YTLPPSRDEL    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPGK                                      449

SEQ ID NO: 84            moltype = AA   length = 448
FEATURE                  Location/Qualifiers
source                   1..448
                         mol_type = protein
                         organism = synthetic construct
SEQUENCE: 84
EVQLLESGGG LVQPGGSLRL SCAASGLTFR SYAMTWVRQA PGKGLEWVSG ISVSGGITYY    60
ASSVKGRFTI SRDNSKNTLY LQMNSLRAED TAVYYCAKRG AAVGSFDYWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELEGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL GAPIEKTISK AKGQPREPQV YTLPPSRDEL    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPG                                       448

SEQ ID NO: 85            moltype = AA   length = 622
FEATURE                  Location/Qualifiers
source                   1..622
                         mol_type = protein
                         organism = Homo sapiens
SEQUENCE: 85
MALPTARPLL GSCGTPALGS LLFLLFSLGW VQPSRTLAGE TGQEAAPLDG VLANPPNISS    60
LSPRQLLGFP CAEVSGLSTE RVRELAVALA QKNVKLSTEQ LRCLAHRLSE PPEDLDALPL    120
DLLLFLNPDA FSGPQACTRF FSRITKANVD LLPRGAPERQ RLLPAALACW GVRGSLLSEA    180
DVRALGGLAC DLPGRFVAES AEVLLPRLVS CPGPLDQDQQ EAARAALQGG GPPYGPPSTW    240
SVSTMDALRG LLPVLGQPII RSIPQGIVAA WRQRSSRDPS WRQPERTILR PRFRREVEKT    300
ACPSGKKARE IDESLIFYKK WELEACVDAA LLATQMDRVN AIPFTYEQLD VKHKLDELY    360
PQGYPESVIQ HLGYLFLKMS PEDIRKWNVT SLETLKALLE VNKGHEMSPQ VATLIDRFVK    420
GRGQLDKDTL DTLTAFYPGY LCSLSPEELS SVPPSSIWAV RPQDLDVCDP RQLDVLYPKA    480
```

```
RLAFQNMNGS EYFVKIQSFL GGAPTEDLKA LSQQNVSMDL ATFMKLRTDA VLPLTVAEVQ   540
KLLGPHVEGL KAEERHRPVR DWILRQRQDD LDTLGLGLQG GIPNGYLVLD LSMQEALSGT   600
PCLLGPGPVL TVLALLLAST LA                                           622
```

ANTI-MESOTHELIN ANTIGEN-BINDING MOLECULES AND USES THEREOF

RELATED APPLICATION

This application is a Continuation of U.S. application Ser. No. 17/938,349, filed on Oct. 6, 2022, which claims benefit to U.S. Provisional Application No. 63/262,156, filed on Oct. 6, 2021, and U.S. Provisional Application No. 63/369,989, filed on Aug. 1, 2022, the contents of which are herein incorporated by reference in their entireties.

SEQUENCE LISTING

The content of the electronically submitted Sequence Listing XML (Name: 196964_SL; Size: 97,367 bytes; Created: Aug. 30, 2023) is herein incorporated by reference in its entirety.

FIELD

The present disclosure relates to antibodies that are specific for human mesothelin (MSLN), including bispecific antibodies that bind MSLN and a T cell antigen (e.g., CD3), and methods of use thereof.

BACKGROUND

Mesothelin (MSLN) is a cell surface glycoprotein with normal expression limited to mesothelial cells lining the pleura, pericardium, and peritoneum. The mesothelin gene encodes a 71-kDa precursor protein that is cleaved by the endoprotease furin into a 40-kDa membrane-bound protein, termed mesothelin, and a 31-kDa shed fragment that is released from the cell, called megakaryocyte-potentiating factor (MPF). A soluble form of the mesothelin protein is likely the result of an abnormal splicing event resulting in a frameshift mutation and premature termination, which deletes the amino acids at the C-terminus that are responsible for the protein's association with the cell membrane (Hassan et al., Clinical Cancer Research, 10:3937-3942, 2004).

Mesothelin is highly expressed in a variety of tumor types, including mesotheliomas, pancreatic cancers, ovarian cancers, and stomach and lung adenocarcinomas. The limited distribution of mesothelin on normal tissues makes it a promising target for tumor-specific therapy. Evidence suggests that the extracellular domain of membrane-bound mesothelin is shed from tumor cells, although the precise mechanism associated with this shedding has not yet been elucidated (Ho and Lively, Cancer Epidemiol Biomarkers Prev., 15(9):1751, 2006). These soluble forms of mesothelin can impede tumor cell-directed immunotherapies by producing an antigen sink that binds anti-MSLN antibodies.

CD3 is a homodimeric or heterodimeric antigen expressed on T cells in association with the T cell receptor complex (TCR) and is required for T cell activation. Functional CD3 is formed from dimeric arrangement of four different chains, including gamma/epsilon, delta/epsilon, and zeta/zeta. Antibodies against CD3 have been shown to cluster CD3 on T cells, thereby causing T cell activation in a manner similar to the engagement of the TCR by peptide-loaded MHC molecules. Bispecific antibodies that are capable of binding CD3 and a target antigen have been proposed for therapeutic uses involving targeted T cell immune responses to tissues and cells expressing the target antigen.

Thus, there is a need for therapies, including bispecific antibodies that bind MSLN and a T cell antigen (e.g., CD3), for targeting and T cell-mediated killing of tumor cells that express MSLN.

SUMMARY

The present disclosure provides antibodies and polypeptides that specifically bind to MSLN (e.g., human MSLN), including bispecific antibodies that bind both MSLN and a T cell antigen (e.g., CD3). Also provided are pharmaceutical compositions comprising these antibodies, nucleic acids encoding these antibodies, expression vectors and host cells for making these antibodies, and methods of treating a subject using these antibodies. The antibodies disclosed herein are particularly advantageous in that they have high isoelectric points and unexpectedly fast serum clearance in human FcRn knock-in mice. This type of pharmacokinetic profile has been shown to result in increased biodistribution and tissue retention in a subject, relative antibodies with low isoelectric points and slow serum clearance (see, e.g., Li et al., MAbs., 6(5):1255-64, 2014; Boswell et al., Bioconjug Chem., 21(12):2153-63, 2010). Applicant anticipates that this increased biodistribution will be advantageous for the treatment of tumors in a human subject.

In one aspect, the present disclosure provides an antibody that specifically binds human MSLN, the antibody comprising: a VH comprising the CDRH1, CDRH2, and CDRH3 amino acid sequences of the VH amino acid sequence set forth in SEQ ID NO: 11; and a VL comprising the CDRL1, CDRL2, and CDRL3 amino acid sequences of the VL amino acid sequence set forth in SEQ ID NO: 12, wherein the antibody does not comprise SEQ ID NO: 4 and/or 8.

In an embodiment, the antibody comprises the CDRH1, CDRH2, and CDRH3 amino acid sequences, respectively, set forth in SEQ ID NOs: 3, 13, and 5.

In an embodiment, the antibody comprises the CDRL1, CDRL2, and CDRL3 amino acid sequences, respectively, set forth in SEQ ID NOs: 6, 7, and 14.

In an embodiment, the antibody comprises the CDRH1, CDRH2, CDRH3, CDRL1, CDRL2, and CDRL3 amino acid sequences, respectively, set forth in SEQ ID NOs: 3, 13, 5, 6, 7, and 14.

In an embodiment, the antibody comprises the CDRH1, CDRH2, and CDRH3 amino acid sequences, respectively, set forth in SEQ ID NOs: 3, 30, and 5; 3, 29, and 5; 3, 31, and 5; 3, 32, and 5; 3, 33, and 5; or 3, 34, and 5.

In an embodiment, the antibody comprises the CDRL1, CDRL2, and CDRL3 amino acid sequences, respectively, set forth in SEQ ID NOs: 6, 7, and 35; 6, 7, and 36; 6, 7, and 37; 6, 7, and 38; 6, 7, and 39; or 6, 7, and 40.

In an embodiment, the antibody comprises the CDRH1, CDRH2, CDRH3, CDRL1, CDRL2, and CDRL3 amino acid sequences, respectively, set forth in SEQ ID NOs: 3, 30, 5, 6, 7, and 35; 3, 29, 5, 6, 7, and 35; 3, 29, 5, 6, 7, and 36; 3, 29, 5, 6, 7, and 37; 3, 29, 5, 6, 7, and 38; 3, 29, 5, 6, 7, and 39; 3, 29, 5, 6, 7, and 40; 3, 30, 5, 6, 7, and 36; 3, 30, 5, 6, 7, and 37; 3, 30, 5, 6, 7, and 38; 3, 30, 5, 6, 7, and 39; 3, 30, 5, 6, 7, and 40; 3, 31, 5, 6, 7, and 35; 3, 31, 5, 6, 7, and 36; 3, 31, 5, 6, 7, and 37; 3, 31, 5, 6, 7, and 38; 3, 31, 5, 6, 7, and 39; 3, 31, 5, 6, 7, and 40; 3, 32, 5, 6, 7, and 35; 3, 32, 5, 6, 7, and 36; 3, 32, 5, 6, 7, and 37; 3, 32, 5, 6, 7, and 38; 3, 32, 5, 6, 7, and 39; 3, 32, 5, 6, 7, and 40; 3, 33, 5, 6, 7, and 35; 3, 33, 5, 6, 7, and 36; 3, 33, 5, 6, 7, and 37; 3, 33, 5, 6, 7, and 38; 3, 33, 5, 6, 7, and 39; 3, 33, 5, 6, 7, and 40; 3, 34, 5, 6, 7, and 35; 3, 34, 5, 6, 7, and 36; 3, 34, 5, 6, 7, and 37; 3, 34, 5, 6, 7, and 38; 3, 34, 5, 6, 7, and 39; or 3, 34, 5, 6, 7, and 40.

In an embodiment, the antibody comprises the VH amino acid sequence of SEQ ID NO: 11.

In an embodiment, the antibody comprises the VH amino acid sequence of SEQ ID NO: 18, 17, 19, 20, 21, or 22.

In an embodiment, the antibody comprises a heavy chain constant region, optionally selected from the group consisting of human IgG1, IgG2, IgG3, IgG4, IgA1, and IgA2.

In an embodiment, the antibody comprises a heavy chain constant region that is a variant of a wild-type heavy chain constant region, wherein the variant heavy chain constant region binds to an FcγR with lower affinity than the wild-type heavy chain constant region binds to the FcγR.

In an embodiment, the heavy chain constant region comprises the amino acid sequence of SEQ ID NO: 53, 54, 55, 56, or 72.

In an embodiment, the antibody comprises a heavy chain comprising the amino acid sequence of SEQ ID NO: 83, 84, 41, 42, 43, 44, 45, 46, 66, 67, 68, 69, 70, or 71.

In an embodiment, the antibody comprises the VL amino acid sequence of SEQ ID NO: 12.

In an embodiment, the antibody comprises the VL amino acid sequence of SEQ ID NO: 24, 23, 25, 26, 27, or 28.

In an embodiment, the antibody comprises a light chain comprising the amino acid sequence of SEQ ID NO: 48, 47, 49, 50, 51, or 52.

In an embodiment, the VH and VL comprise the amino acid sequences, respectively, set forth in SEQ ID NOs: 18 and 24, 17 and 23, 17 and 24, 17 and 25, 17 and 26, 17 and 27, 17 and 28, 18 and 23, 18 and 25, 18 and 26, 18 and 27, 18 and 28, 19 and 23, 19 and 24, 19 and 25, 19 and 26, 19 and 27, 19 and 28, 20 and 23, 20 and 24, 20 and 25, 20 and 26, 20 and 27, 20 and 28, 21 and 23, 21 and 24, 21 and 25, 21 and 26, 21 and 27, 21 and 28, 22 and 23, 22 and 24, 22 and 25, 22 and 26, 22 and 27, or 22 and 28.

In an embodiment, the heavy chain and light chain comprise the amino acid sequences, respectively, set forth in SEQ ID NOs: 83 and 48, 84 and 48, 83 and 49, 84 and 49, 83 and 50, 84 and 50, 83 and 51, 84 and 51, 83 and 52, 84 and 52, 83 and 47, 84 and 47, 41 and 47, 41 and 48, 41 and 49, 41 and 50, 41 and 51, 41 and 52, 42 and 47, 42 and 48, 42 and 49, 42 and 50, 42 and 51, 42 and 52, 43 and 47, 43 and 48, 43 and 49, 43 and 50, 43 and 51, 43 and 52, 44 and 47, 44 and 48, 44 and 49, 44 and 50, 44 and 51, 44 and 52, 45 and 47, 45 and 48, 45 and 49, 45 and 50, 45 and 51, 45 and 52, 46 and 47, 46 and 48, 46 and 49, 46 and 50, 46 and 51, 46 and 52, 66 and 47, 66 and 48, 66 and 49, 66 and 50, 66 and 51, 66 and 52, 67 and 47, 67 and 48, 67 and 49, 67 and 50, 67 and 51, 67 and 52, 68 and 47, 68 and 48, 68 and 49, 68 and 50, 68 and 51, 68 and 52, 69 and 47, 69 and 48, 69 and 49, 69 and 50, 69 and 51, 69 and 52, 70 and 47, 70 and 48, 70 and 49, 70 and 50, 70 and 51, 70 and 52, 71 and 47, 71 and 48, 71 and 49, 71 and 50, 71 and 51, or 71 and 52.

In an embodiment, the antibody further comprises a CD3 binding moiety.

In an embodiment, the CD3 binding moiety is a polypeptide. In an embodiment, the CD3 binding moiety is an antibody. In an embodiment, the CD3 binding moiety is a single-chain fragment variable (scFv). In an embodiment, the scFv comprises the amino acid sequence set forth in SEQ ID NO: 76.

In an embodiment, the CD3 binding moiety is covalently linked to the light chain. In an embodiment, the CD3 binding moiety is covalently linked to the C-terminus of the light chain. In an embodiment, the CD3 binding moiety is covalently linked to the C-terminus of the light chain via a peptide linker, optionally wherein the peptide linker comprises the amino acid sequence set forth in SEQ ID NO: 63, 64, 73, 74, or 75.

In an embodiment, the light chain comprises the amino acid sequence set forth in SEQ ID NO: 77, 78, 79, 80, 81, or 82.

In one aspect, the present disclosure provides an antibody that specifically binds human MSLN, the antibody comprising a heavy chain and a light chain comprising the amino acid sequences, respectively, set forth in SEQ ID NOs: 83 and 77, 84 and 77, 41 and 77, 42 and 77, 43 and 77, 44 and 77, 45 and 77, 46 and 77, 66 and 77, 67 and 77, 68 and 77, 69 and 77, 70 and 77, 71 and 77, 83 and 78, 84 and 78, 41 and 78, 42 and 78, 43 and 78, 44 and 78, 45 and 78, 46 and 78, 66 and 78, 67 and 78, 68 and 78, 69 and 78, 70 and 78, 71 and 78, 83 and 79, 84 and 79, 41 and 79, 42 and 79, 43 and 79, 44 and 79, 45 and 79, 46 and 79, 66 and 79, 67 and 79, 68 and 79, 69 and 79, 70 and 79, 71 and 79, 83 and 80, 84 and 80, 41 and 80, 42 and 80, 43 and 80, 44 and 80, 45 and 80, 46 and 80, 66 and 80, 67 and 80, 68 and 80, 69 and 80, 70 and 80, 71 and 80, 83 and 81, 84 and 81, 41 and 81, 42 and 81, 43 and 81, 44 and 81, 45 and 81, 46 and 81, 66 and 81, 67 and 81, 68 and 81, 69 and 81, 70 and 81, 71 and 81, 83 and 82, 84 and 82, 41 and 82, 42 and 82, 43 and 82, 44 and 82, 45 and 82, 46 and 82, 66 and 82, 67 and 82, 68 and 82, 69 and 82, 70 and 82, or 71 and 82.

In an embodiment, the heavy chain and the light chain comprise the amino acid sequences, respectively, set forth in SEQ ID NOs: 83 and 77.

In one aspect, the present disclosure provides a polypeptide comprising a VH comprising the CDRH1, CDRH2, and CDRH3 amino acid sequences of the VH amino acid sequence set forth in SEQ ID NO: 11, wherein the polypeptide does not comprise SEQ ID NO: 4. In an embodiment, the VH comprises the CDRH1, CDRH2, and CDRH3 amino acid sequences, respectively, set forth in SEQ ID NOs: 3, 13, and 5. In an embodiment, the VH comprises the CDRH1, CDRH2, and CDRH3 amino acid sequences, respectively, set forth in SEQ ID NOs: 3, 30, and 5; 3, 29, and 5; 3, 31, and 5; 3, 32, and 5; 3, 33, and 5; or 3, 34, and 5. In an embodiment, the VH comprises the amino acid sequence of SEQ ID NO: 11. In an embodiment, the VH comprises the amino acid sequence of SEQ ID NO: 18, 17, 19, 20, 21, or 22.

In an embodiment, the polypeptide comprises a heavy chain comprising the amino acid sequence of SEQ ID NO: 83, 84, 41, 42, 43, 44, 45, 46, 66, 67, 68, 69, 70, or 71.

In one aspect, the present disclosure provides a polypeptide comprising a VL comprising the CDRL1, CDRL2, and CDRL3 amino acid sequences of the VL amino acid sequence set forth in SEQ ID NO: 12, wherein the polypeptide does not comprise SEQ ID NO: 8. In an embodiment, the VL comprises the CDRL1, CDRL2, and CDRL3 amino acid sequences, respectively, set forth in SEQ ID NOs: 6, 7, and 14. In an embodiment, the VL comprises the CDRL1, CDRL2, and CDRL3 amino acid sequences, respectively, set forth in SEQ ID NOs: 6, 7, and 35; 6, 7, and 36; 6, 7, and 37; 6, 7, and 38; 6, 7, and 39; or 6, 7, and 40. In an embodiment, the VL comprises the amino acid sequence of SEQ ID NO: 12. In an embodiment, the VL comprises the amino acid sequence of SEQ ID NO: 24, 23, 25, 26, 27, or 28.

In an embodiment, the polypeptide comprises a light chain comprising the amino acid sequence of SEQ ID NO: 77, 47, 48, 49, 50, 51, 52, 78, 79, 80, 81, or 82.

In one aspect, the present disclosure provides a polypeptide comprising the amino acid sequence set forth in SEQ ID NO: 73, 74, or 75.

In an embodiment, an antibody or polypeptide disclosed herein is conjugated to a cytotoxic agent, cytostatic agent, toxin, radionuclide, or detectable label.

In one aspect, the present disclosure provides a polynucleotide encoding: a VH, a VL, a heavy chain, and/or a light chain of an antibody disclosed herein; or a polypeptide disclosed herein.

In one aspect, the present disclosure provides a vector comprising a polynucleotide disclosed herein.

In one aspect, the present disclosure provides a recombinant host cell comprising:
(a) a polynucleotide disclosed herein;
(b) a vector disclosed herein;
(c) a first polynucleotide encoding a heavy chain variable region or a heavy chain of an antibody disclosed herein, and a second polynucleotide encoding a light chain variable region or a light chain of an antibody disclosed herein;
(d) a first vector comprising a first polynucleotide encoding a heavy chain variable region or a heavy chain of an antibody disclosed herein, and a second vector comprising a second polynucleotide encoding a light chain variable region or a light chain of an antibody disclosed herein.

In one aspect, the present disclosure provides a pharmaceutical composition comprising an antibody disclosed herein, a polypeptide disclosed herein, a polynucleotide disclosed herein, a vector disclosed herein, a host cell disclosed herein, and a pharmaceutically acceptable carrier or excipient.

In one aspect, the present disclosure provides a method of producing an antibody, the method comprising culturing a host cell disclosed herein under suitable conditions such that the polynucleotide is expressed, and the antibody is produced.

In one aspect, the present disclosure provides a method of treating cancer in a subject, the method comprising administering to the subject an effective amount of an antibody disclosed herein, a polypeptide disclosed herein, a polynucleotide disclosed herein, a vector disclosed herein, a host cell disclosed herein, or a pharmaceutical composition disclosed herein.

In one aspect, the present disclosure provides use of an antibody disclosed herein, a polypeptide disclosed herein, a polynucleotide disclosed herein, a vector disclosed herein, a host cell disclosed herein, or a pharmaceutical composition disclosed herein, for the manufacture of a medicament for the treatment of cancer in a subject in need thereof.

In one aspect, the present disclosure provides an antibody disclosed herein, a polypeptide disclosed herein, a polynucleotide disclosed herein, a vector disclosed herein, a host cell disclosed herein, or a pharmaceutical composition disclosed herein, for use in medicine.

In one aspect, the present disclosure provides an antibody disclosed herein, a polypeptide disclosed herein, a polynucleotide disclosed herein, a vector disclosed herein, a host cell disclosed herein, or a pharmaceutical composition disclosed herein, for use in the treatment of cancer in a subject in need thereof.

BRIEF DESCRIPTION OF THE DRAWINGS

In FIG. 1B, the y-axis is a measure of the intensity of absorbance in milli-absorbance units (mAU) and the x-axis is in minutes used to determine the retention time for each peak.

FIG. 5A shows a size exclusion chromatogram obtained from running crude protein extract comprising the bispecific molecule through a Superdex 200 10/300 GL prepacked gel filtration column. FIG. 5B shows a size exclusion chromatogram obtained from running post-Ni-NTA purified protein extract comprising the bispecific molecule through a Superdex 200 10/300 GL prepacked gel filtration column, resulting in a homogenous single peak of protein centered at about 11 mL. In FIGS. 5A-5B, the y-axis is a measure of the intensity of absorbance in milli-absorbance units (mAU) and the x-axis is in milliliters (mL) used to determine the retention volume for each peak.

FIG. 6A shows a size exclusion chromatogram obtained from running crude protein extract comprising the bispecific molecule through a Superdex 200 10/300 GL prepacked gel filtration column. FIG. 6B shows a size exclusion chromatogram obtained from running post-Ni-NTA purified protein extract comprising the bispecific molecule through a Superdex 200 10/300 GL prepacked gel filtration column, resulting in a homogenous single peak of protein centered at about 13 mL. In FIGS. 6A-6B, the y-axis is a measure of the intensity of absorbance in milli-absorbance units (mAU) and the x-axis is in milliliters (mL) used to determine the retention volume for each peak.

DETAILED DESCRIPTION

Figure 1A:
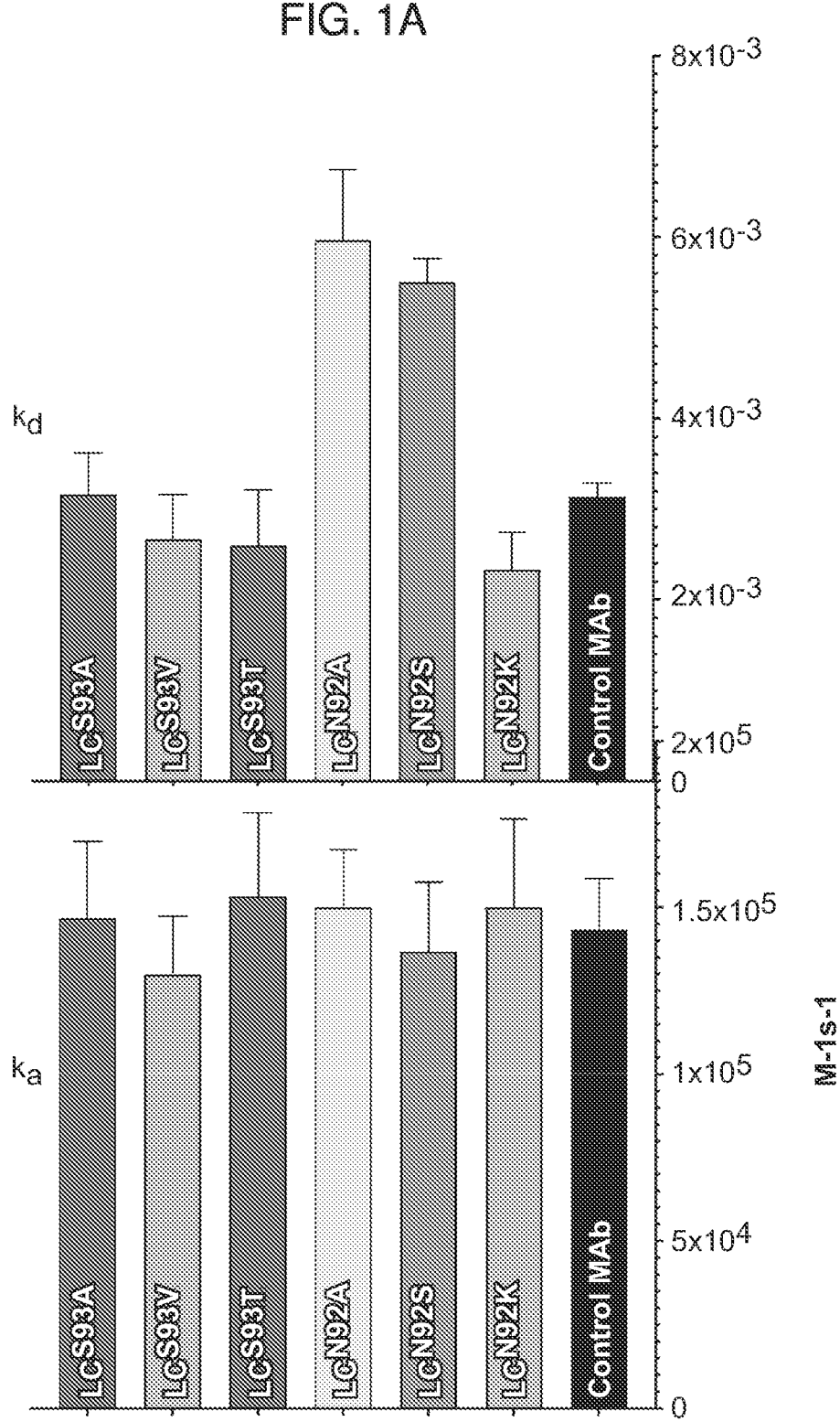
FIG. 1A is a graph showing $K_a$ and $K_d$ (left and right, respectively) for light chain variants of the anti-MSLN 1A12 antibody. Control MAb represents the anti-MSLN 1A12 antibody alone.
Figure 1B:
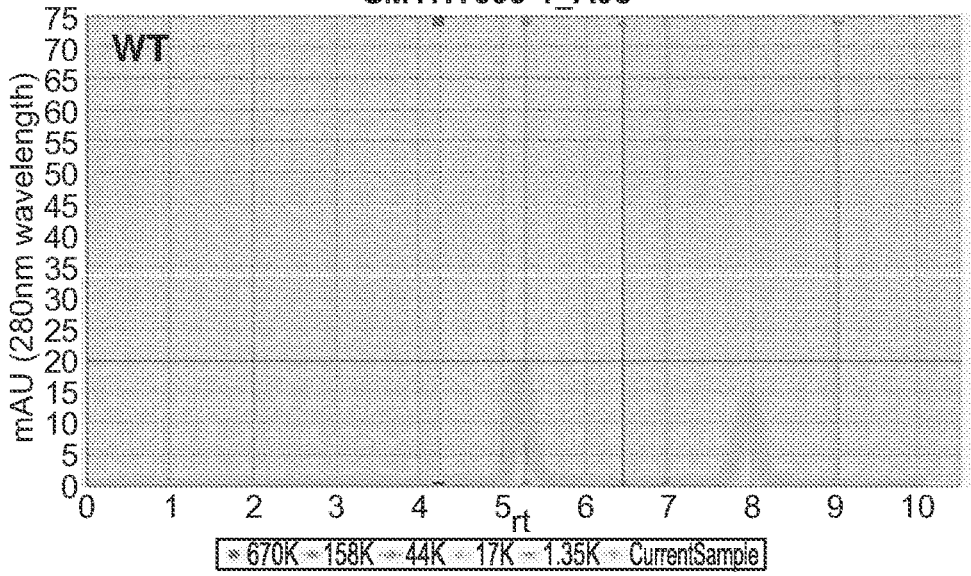
FIG. 1B is a graph showing the effects of the same light chain mutations on antibody expression.
Figure 1B:
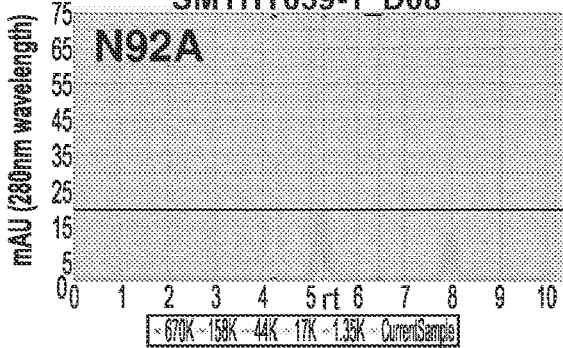
Figure 1B:
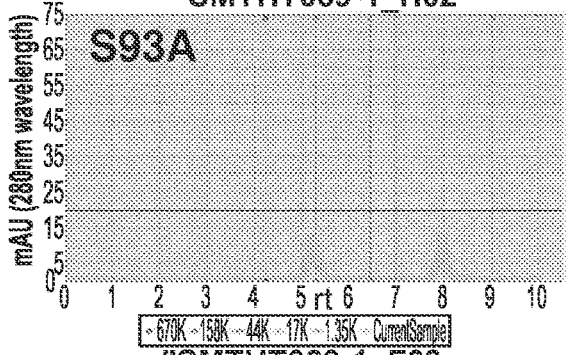
Figure 1B:
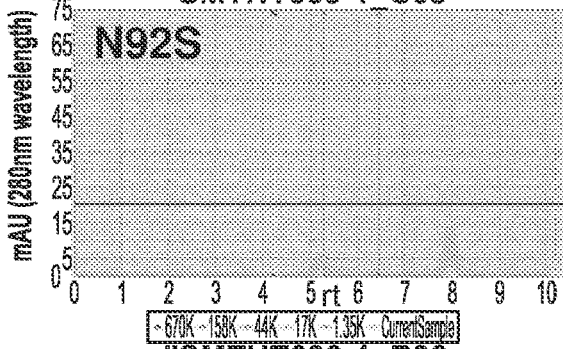
Figure 1B:
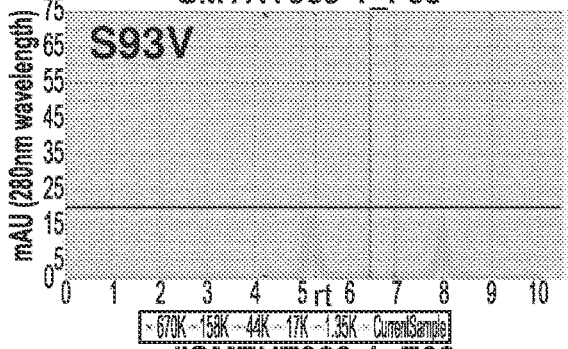
Figure 1B:
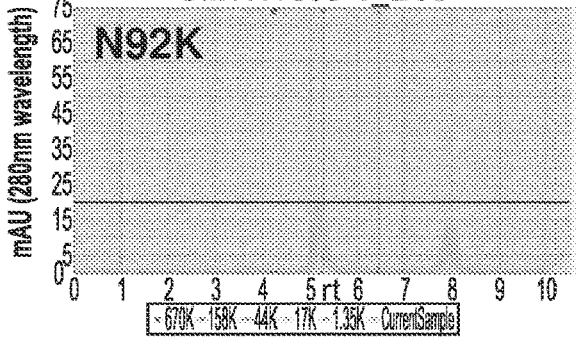
Figure 1B:
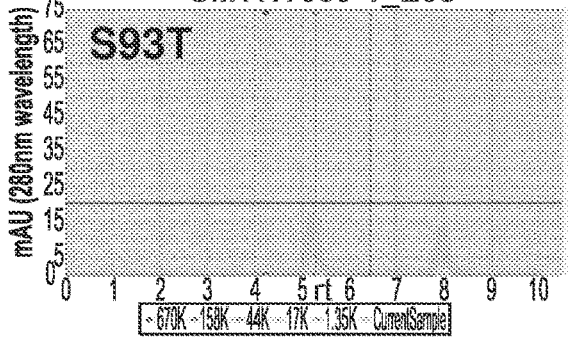

The instant disclosure provides anti-MSLN antibodies and polypeptides, including bispecific antibodies that bind both MSLN and a T cell antigen (e.g., CD3). Also provided are pharmaceutical compositions comprising these antibodies, nucleic acids encoding these antibodies, expression vectors and host cells for making these antibodies, and methods of treating a subject using these antibodies. The antibodies disclosed herein are particularly useful for treating cancer in a subject.

Definitions

The expression "MSLN," as used herein, refers to meso-thelin. The amino acid sequence of human mesothelin can be found below. MSLN is a cell surface glycoprotein that is highly expressed in pancreatic cancers, ovarian cancers, mesotheliomas, and some other cancer types. Mesothelin is expressed on normal mesothelial cells lining the pleura, pericardium, and peritoneum, but has limited distribution on normal tissues. All references to proteins, polypeptides and protein fragments herein are intended to refer to the human version of the respective protein, polypeptide or protein fragment unless explicitly specified as being from a non-human species. Thus, the expression "MSLN" means human MSLN unless specified as being from a non-human species, e.g., "mouse MSLN," "monkey MSLN," etc. MALPTAR-PLLGSCGTPALGSLLFLLFSLGWVQPSRTLAG-ETGQEAAPLDGVLANPPNISS LSPRQLLGFP-CAEVSGLSTERVRELAVALAQKNVKLSTEQLRCLA HRLSEPPEDLDALPL DLLLFLNPDAFSGPQACTRFF-SRITKANVDLLPRGAPERQRLLPAALACWGVRGSLL-SEA DVRALGGLACDLPGRFVAESAEVLLPRLVSCPG-PLDQDQQEAARAALQGGGPPYGPPST WSVSTMDALRGLLPVLGQPIIRSIPQ-GIVAAWRQRSSRDPSWRQPERTILRPRFRREVEKT ACPSGKKAREIDESLIFYKKWELEACVDAAL-LATQMDRVNAIPFTYEQLDVLKHKLDEL YPQGYPESVIQHLGYLFLKMSPEDIRKWNVTSLETL-KALLEVNKGHEMSPQVATLIDRF VKGRGQLDKDTLDTLTAFYPGYLCSL-SPEELSSVPPSSIWAVRPQDLDTCDPRQLDVLYP KAR-LAFQNMNGSEYFVKIQSFLGGAPTEDL-KALSQQNVSMDLATFMKLRTDAVLPLTV AEVQKLLGPHVEGLKAEERHRPVRDWILRQRQD-DLDTLGLGLQGGIPNGYLVLDLSMQ EALSGTPCLLGPGPVLTVLALLLASTLA (SEQ ID NO: 85)

The expression "CD3," as used herein, refers to an antigen which is expressed on T cells as part of the multi-molecular T cell receptor (TCR) and which consists of a homodimer or heterodimer formed from the association of two of four receptor chains: CD3-epsilon, CD3-delta, CD3-zeta, and CD3-gamma.

As used herein, the terms "antibody" and "antibodies" include full-length antibodies, antigen-binding fragments of full-length antibodies, and molecules comprising antibody CDRs, VH regions, and/or VL regions. Examples of antibodies include, without limitation, monoclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, antibody-drug conjugates, single domain antibodies, monovalent antibodies, single-chain antibodies or single-chain Fvs (scFv), camelized antibodies, affibodies, Fab fragments, F(ab')$_2$ fragments, disulfide-linked Fvs (sdFv), anti-idiotypic (anti-Id) antibodies (including, e.g., anti-anti-Id antibodies), and antigen-binding fragments of any of the above. In certain embodiments, antibodies described herein refer to polyclonal antibody populations. Antibodies can be of any type (e.g., IgG, IgE, IgM, IgD, IgA, or IgY), any class (e.g., IgG$_1$, IgG$_2$, IgG$_3$, IgG$_4$, IgA$_1$, or IgA$_2$), or any subclass (e.g., IgG$_2$a or IgG$_2$b) of immunoglobulin molecule. In certain embodiments, antibodies described herein are IgG antibodies, or a class (e.g., human IgG$_1$ or IgG$_4$) or subclass thereof. In a specific embodiment, the antibody is a humanized monoclonal antibody. In another specific embodiment, the antibody is a human monoclonal antibody.

"Multispecific antibodies" are antibodies (e.g., bispecific antibodies) that specifically bind to two or more different antigens or two or more different regions of the same antigen. Multispecific antibodies include bispecific antibodies that contain two different antigen-binding sites (exclusive of the Fc region). Multispecific antibodies can include, for example, recombinantly produced antibodies, human antibodies, humanized antibodies, resurfaced antibodies, chimeric antibodies, immunoglobulins, synthetic antibodies, tetrameric antibodies comprising two heavy chain and two light chain molecules, an antibody light chain monomer, heteroconjugate antibodies, linked single-chain antibodies or linked-single-chain Fvs (scFv), camelized antibodies, affybodies, linked Fab fragments, F(ab')2 fragments, chemically-linked Fvs, and disulfide-linked Fvs (sdFv). Multispecific antibodies can be of any type (e.g., IgG, IgE, IgM, IgD, IgA, or IgY), any class (e.g., IgG$_1$, IgG$_2$, IgG$_3$, IgG$_4$, IgA$_1$, or IgA$_2$), or any subclass (e.g., IgG$_2$a or IgG$_2$b) of immunoglobulin molecule. In certain embodiments, multispecific antibodies described herein are IgG antibodies, or a class (e.g., human IgG$_1$, IgG$_2$, or IgG$_4$) or subclass thereof.

As used herein, the term "CDR" or "complementarity determining region" means the noncontiguous antigen combining sites found within the variable regions of heavy and light chain polypeptides. These particular regions have been described by, for example, Kabat et al., J. Biol. Chem. 252, 6609-6616 (1977) and Kabat et al., Sequences of protein of immunological interest. (1991), by Chothia et al., J. Mol. Biol. 196:901-917 (1987), and by MacCallum et al., J. Mol. Biol. 262:732-745 (1996), all of which are herein incorporated by reference in their entireties, where the definitions include overlapping or subsets of amino acid residues when compared against each other. In certain embodiments, the term "CDR" is a CDR as defined by MacCallum et al., J. Mol. Biol. 262:732-745 (1996) and Martin A. "Protein Sequence and Structure Analysis of Antibody Variable Domains," in Antibody Engineering, Kontermann and Dubel, eds., Chapter 31, pp. 422-439, Springer-Verlag, Berlin (2001). In certain embodiments, the term "CDR" is a CDR as defined by Kabat et al., J. Biol. Chem. 252, 6609-6616 (1977) and Kabat et al., Sequences of protein of immunological interest. (1991). In certain embodiments, heavy chain CDRs and light chain CDRs of an antibody are defined using different conventions. In certain embodiments, heavy chain CDRs and/or light chain CDRs are defined by performing structural analysis of an antibody and identifying residues in the variable region(s) predicted to make contact with an epitope region of a target molecule (e.g., human MSLN). CDRH1, CDRH2, and CDRH3 denote the heavy chain CDRs, and CDRL1, CDRL2, and CDRL3 denote the light chain CDRs.

As used herein, the terms "variable region" and "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable region are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In certain embodiments, the variable region is a primate (e.g., non-human primate) variable region. In certain embodiments, the variable region comprises rodent or murine CDRs and primate (e.g., non-human primate) framework regions (FRs).

As used herein, the terms "VH" and "VL" refer to antibody heavy and light chain variable regions, respectively, as described in Kabat et al., (1991) Sequences of Proteins of Immunological Interest (NIH Publication No. 91-3242, Bethesda), which is herein incorporated by reference in its entirety.

As used herein, the term "constant region" is common in the art. The constant region is an antibody portion, e.g., a carboxyl terminal portion of a light and/or heavy chain, which is not directly involved in binding of an antibody to antigen but which can exhibit various effector functions, such as interaction with an Fc receptor (e.g., Fc gamma receptor).

As used herein, the term "heavy chain" when used in reference to an antibody can refer to any distinct type, e.g., alpha (α), delta (δ), epsilon (ε), gamma (γ), and mu (μ), based on the amino acid sequence of the constant region, which give rise to IgA, IgD, IgE, IgG, and IgM classes of antibodies, respectively, including subclasses of IgG, e.g., $IgG_1$, $IgG_2$, $IgG_3$, and $IgG_4$.

As used herein, the term "light chain" when used in reference to an antibody can refer to any distinct type, e.g., kappa (κ) or lambda (λ), based on the amino acid sequence of the constant region. Light chain amino acid sequences are well known in the art. In specific embodiments, the light chain is a human light chain.

As used herein, the terms "specifically binds," "specifically recognizes," "immunospecifically binds," and "immunospecifically recognizes" are analogous terms in the context of antibodies and refer to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, ID), or other assays known in the art. In a specific embodiment, molecules that specifically bind to an antigen bind to the antigen with a $K_A$ that is at least 2 logs (e.g., factors of 10), 2.5 logs, 3 logs, 4 logs, or greater than the $K_A$ when the molecules bind non-specifically to another antigen.

As used herein, the term "affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein.

As used herein, the term "EU numbering system" refers to the EU numbering convention for the constant regions of an antibody, as described in Edelman, G. M. et al., Proc. Natl. Acad. USA, 63, 78-85 (1969) and Kabat et al, Sequences of Proteins of Immunological Interest, U.S. Dept. Health and Human Services, 5th edition, 1991, each of which is herein incorporated by reference in its entirety.

As used herein, the term "treat," "treating," and "treatment" refer to therapeutic or preventative measures described herein. The methods of "treatment" employ administration of an antibody to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein, the term "subject" includes any human or non-human animal. In certain embodiments, the subject is a human or non-human mammal. In certain embodiments, the subject is a human.

As used herein with respect to an antibody or polynucleotide, the term "isolated" refers to an antibody or polynucleotide that is separated from one or more contaminants (e.g., polypeptides, polynucleotides, lipids, or carbohydrates, etc.) which are present in a natural source of the antibody or polynucleotide. All instances of "isolated antibodies" described herein are additionally contemplated as antibodies that may be, but need not be, isolated. All instances of "isolated polynucleotides" described herein are additionally contemplated as polynucleotides that may be, but need not be, isolated. All instances of "antibodies" described herein are additionally contemplated as antibodies that may be, but need not be, isolated. All instances of "polynucleotides" described herein are additionally contemplated as polynucleotides that may be, but need not be, isolated.

The determination of "percent identity" between two sequences (e.g., amino acid sequences or nucleic acid sequences) can be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877, each of which is herein incorporated by reference in its entirety. Such an algorithm is incorporated into the NBLAST and XBLAST programs of Altschul S F et al., (1990) J Mol Biol 215: 403, which is herein incorporated by reference in its entirety. BLAST nucleotide searches can be performed with the NBLAST nucleotide program parameters set, e.g., for score=100, wordlength=12 to obtain nucleotide sequences homologous to a nucleic acid molecule described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389-3402, which is herein incorporated by reference in its entirety. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, 1988, CABIOS 4:11-17, which is herein incorporated by reference in its entirety. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

Anti-MSLN Antibodies

In one aspect, the instant disclosure provides antibodies that specifically bind to MSLN (e.g., human MSLN). The amino acid sequences of exemplary antibodies are set forth in Table 1.

TABLE 1

Amino acid sequences of exemplary anti-MSLN antibodies.

| Description | Amino Acid Sequence | SEQ ID NO |
|---|---|---|
| 1A12 (Parent Clone) VH | EVQLLESGGGLVQPGGSLRLSCAASGLTFRSYAMTWVRQAPGKGLEWVSG ISVSGGITYYADSVKGRFTISRDNSKNTLYLQMNSLRAEDTAVYYCAKRG AAVGSFDYWGQGTLVTVSS | 1 |
| 1A12 VL | DIQMTQSPSSLSASVGDRVTITCRSSQGIGSWLAWYQQKPEKAPQSLIYA ASSLQSGVPSRFSGSGSGTDFTLTISNLQPEDFATYYCQQYNSYPLTFGG GTKVEIK | 2 |
| 1A12 CDRH1 | GLTFRSYAMT | 3 |
| 1A12 CDRH2 | GISVSGGITYYADSVKG | 4 |
| 1A12 CDRH3 | RGAAVGSFDY | 5 |
| 1A12 CDRL1 | RSSQGIGSWLA | 6 |
| 1A12 CDRL2 | AASSLQS | 7 |
| 1A12 CDRL3 | QQYNSYPLT | 8 |
| 1A12 HC | EVQLLESGGGLVQPGGSLRLSCAASGLTFRSYAMTWVRQAPGKGLEWVSG ISVSGGITYYADSVKGRFTISRDNSKNTLYLQMNSLRAEDTAVYYCAKRG AAVGSFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYAS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK | 9 |

TABLE 1-continued

Amino acid sequences of exemplary anti-MSLN antibodies.

| Description | Amino Acid Sequence | SEQ ID NO |
|---|---|---|
| 1A12 LC | DIQMTQSPSSLSASVGDRVTITCRSSQGIGSWLAWYQQKPEKAPQSLIYA ASSLQSGVPSRFSGSGSGTDFTLTISNLQPEDFATYYCQQYNSYPLTFGG GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC | 10 |
| Consensus sequence VH | EVQLLESGGGLVQPGGSLRLSCAASGLTFRSYAMTWVRQAPGKGLEWVSG ISVSGGITYYAX$_1$X$_2$VKGRFTISRDNSKNTLYLQMNSLRAEDTAVYYCAK RGAAVGSFDYWGQGTLVTVSS<br>X$_1$ is D, A, S, or E<br>X$_2$ is S, T, V, or A | 11 |
| Consensus sequence VL | DIQMTQSPSSLSASVGDRVTITCRSSQGIGSWLAWYQQKPEKAPQSLIYA ASSLQSGVPSRFSGSGSGTDFTLTISNLQPEDFATYYCQQYX$_1$X$_2$YPLTF GGGTKVEIK<br>X$_1$ is N, A, S, or K<br>X$_2$ is S, T, V, or A | 12 |
| Consensus sequence CDRH2 | GISVSGGITYYAX$_1$X$_2$VKG<br>X$_1$ is D, A, S, or E<br>X$_2$ is S, T, V, or A | 13 |
| Consensus sequence CDRL3 | QQYX$_1$X$_2$YPLT<br>X$_1$ is N, A, S, or K<br>X$_2$ is S, T, V, or A | 14 |
| Consensus sequence HC | EVQLLESGGGLVQPGGSLRLSCAASGLTFRSYAMTWVRQAPGKGLEWVSG ISVSGGITYYAX$_1$X$_2$VKGRFTISRDNSKNTLYLQMNSLRAEDTAVYYCAK RGAAVGSFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPK PKDTLMISRTPEVTCVVVDVSHEDPEVKFNWYVDGVEVHNAKTKPREEQY ASTYRVVSVLTVLHQDWLNGKEYKCKVSNKALPAPIEKTISKAKGQPREP QVYTLPPSRDELTKNQVSLTCLVKGFYPSDIAVEWESNGQPENNYKTTPP VLDSDGSFFLYSKLTVDKSRWQQGNVFSCSVMHEALHNHYTQKSLSLSPG K<br>X$_1$ is D, A, S, or E<br>X$_2$ is S, T, V, or A | 15 |
| Consensus sequence HC | EVQLLESGGGLVQPGGSLRLSCAASGLTFRSYAMTWVRQAPGKGLEWVSG ISVSGGITYYAX$_1$X$_2$VKGRFTISRDNSKNTLYLQMNSLRAEDTAVYYCAK RGAAVGSFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPK PKDTLMISRTPEVTCVVVDVSHEDPEVKFNWYVDGVEVHNAKTKPREEQY ASTYRVVSVLTVLHQDWLNGKEYKCKVSNKALPAPIEKTISKAKGQPREP QVYTLPPSRDELTKNQVSLTCLVKGFYPSDIAVEWESNGQPENNYKTTPP VLDSDGSFFLYSKLTVDKSRWQQGNVFSCSVMHEALHNHYTQKSLSLSPG<br>X$_1$ is D, A, S, or E<br>X$_2$ is S, T, V, or A | 65 |
| Consensus sequence LC | DIQMTQSPSSLSASVGDRVTITCRSSQGIGSWLAWYQQKPEKAPQSLIYA ASSLQSGVPSRFSGSGSGTDFTLTISNLQPEDFATYYCQQYX$_1$X$_2$YPLTF GGGTKVEIKRTVAAPSVFIFPPSDEQLKSGTASVVCLLNNFYPREAKVQW KVDNALQSGNSQESVTEQDSKDSTYSLSSTLTLSKADYEKHKVYACEVTH QGLSSPVTKSFNRGEC<br>X$_1$ is N, A, S, or K<br>X$_2$ is S, T, V, or A | 16 |
| SMT577 (D62E) VH | EVQLLESGGGLVQPGGSLRLSCAASGLTFRSYAMTWVRQAPGKGLEWVSG ISVSGGITYYAESVKGRFTISRDNSKNTLYLQMNSLRAEDTAVYYCAKRG AAVGSFDYWGQGTLVTVSS | 17 |
| SMT578 (D62S) VH | EVQLLESGGGLVQPGGSLRLSCAASGLTFRSYAMTWVRQAPGKGLEWVSG ISVSGGITYYASSVKGRFTISRDNSKNTLYLQMNSLRAEDTAVYYCAKRG AAVGSFDYWGQGTLVTVSS | 18 |
| SMT579 (D62A) VH | EVQLLESGGGLVQPGGSLRLSCAASGLTFRSYAMTWVRQAPGKGLEWVSG ISVSGGITYYAASVKGRFTISRDNSKNTLYLQMNSLRAEDTAVYYCAKRG AAVGSFDYWGQGTLVTVSS | 19 |
| SMT580 (S63T) VH | EVQLLESGGGLVQPGGSLRLSCAASGLTFRSYAMTWVRQAPGKGLEWVSG ISVSGGITYYADTVKGRFTISRDNSKNTLYLQMNSLRAEDTAVYYCAKRG AAVGSFDYWGQGTLVTVSS | 20 |

TABLE 1-continued

Amino acid sequences of exemplary anti-MSLN antibodies.

| Description | Amino Acid Sequence | SEQ ID NO |
|---|---|---|
| SMT581 (S63V) VH | EVQLLESGGGLVQPGGSLRLSCAASGLTFRSYAMTWVRQAPGKGLEWVSG ISVSGGITYYADVVKGRFTISRDNSKNTLYLQMNSLRAEDTAVYYCAKRG AAVGSFDYWGQGTLVTVSS | 21 |
| SMT582 (S63A) VH | EVQLLESGGGLVQPGGSLRLSCAASGLTFRSYAMTWVRQAPGKGLEWVSG ISVSGGITYYADAVKGRFTISRDNSKNTLYLQMNSLRAEDTAVYYCAKRG AAVGSFDYWGQGTLVTVSS | 22 |
| SMT571 (N92K) VL | DIQMTQSPSSLSASVGDRVTITCRSSQGIGSWLAWYQQKPEKAPQSLIYA ASSLQSGVPSRFSGSGSGTDFTLTISNLQPEDFATYYCQQYKSYPLTFGG GTKVEIK | 23 |
| SMT572 (N92S) VL | DIQMTQSPSSLSASVGDRVTITCRSSQGIGSWLAWYQQKPEKAPQSLIYA ASSLQSGVPSRFSGSGSGTDFTLTISNLQPEDFATYYCQQYSSYPLTFGG GTKVEIK | 24 |
| SMT573 (N92A) VL | DIQMTQSPSSLSASVGDRVTITCRSSQGIGSWLAWYQQKPEKAPQSLIYA ASSLQSGVPSRFSGSGSGTDFTLTISNLQPEDFATYYCQQYASYPLTFGG GTKVEIK | 25 |
| SMT574 (S93T) VL | DIQMTQSPSSLSASVGDRVTITCRSSQGIGSWLAWYQQKPEKAPQSLIYA ASSLQSGVPSRFSGSGSGTDFTLTISNLQPEDFATYYCQQYNTYPLTFGG GTKVEIK | 26 |
| SMT575 (S93V) VL | DIQMTQSPSSLSASVGDRVTITCRSSQGIGSWLAWYQQKPEKAPQSLIYA ASSLQSGVPSRFSGSGSGTDFTLTISNLQPEDFATYYCQQYNVYPLTFGG GTKVEIK | 27 |
| SMT576 (S93A) VL | DIQMTQSPSSLSASVGDRVTITCRSSQGIGSWLAWYQQKPEKAPQSLIYA ASSLQSGVPSRFSGSGSGTDFTLTISNLQPEDFATYYCQQYNAYPLTFGG GTKVEIK | 28 |
| SMT577 (D62E) CDRH2 | GISVSGGITYYAESVKG | 29 |
| SMT578 (D62S) CDRH2 | GISVSGGITYYASSVKG | 30 |
| SMT579 (D62A) CDRH2 | GISVSGGITYYAASVKG | 31 |
| SMT580 (S63T) CDRH2 | GISVSGGITYYADTVKG | 32 |
| SMT581 (S63V) CDRH2 | GISVSGGITYYADVVKG | 33 |
| SMT582 (S63A) CDRH2 | GISVSGGITYYADAVKG | 34 |
| SMT571 (N92K) CDRL3 | QQYKSYPLT | 35 |
| SMT572 (N92S) CDRL3 | QQYSSYPLT | 36 |
| SMT573 (N92A) CDRL3 | QQYASYPLT | 37 |
| SMT574 (S93T) CDRL3 | QQYNTYPLT | 38 |
| SMT575 (S93V) CDRL3 | QQYNVYPLT | 39 |

TABLE 1-continued

Amino acid sequences of exemplary anti-MSLN antibodies.

| Description | Amino Acid Sequence | SEQ ID NO |
|---|---|---|
| SMT576 (S93A) CDRL3 | QQYNAYPLT | 40 |
| SMT577 (D62E) HC | EVQLLESGGGLVQPGGSLRLSCAASGLTFRSYAMTWVRQAPGKGLEWVSG ISVSGGITYYAESVKGRFTISRDNSKNTLYLQMNSLRAEDTAVYYCAKRG AAVGSFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYAS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK | 41 |
| SMT577 (D62E) HC | EVQLLESGGGLVQPGGSLRLSCAASGLTFRSYAMTWVRQAPGKGLEWVSG ISVSGGITYYAESVKGRFTISRDNSKNTLYLQMNSLRAEDTAVYYCAKRG AAVGSFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYAS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 66 |
| SMT578 (D62S) HC | EVQLLESGGGLVQPGGSLRLSCAASGLTFRSYAMTWVRQAPGKGLEWVSG ISVSGGITYYASSVKGRFTISRDNSKNTLYLQMNSLRAEDTAVYYCAKRG AAVGSFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYAS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK | 42 |
| SMT578 (D62S) HC | EVQLLESGGGLVQPGGSLRLSCAASGLTFRSYAMTWVRQAPGKGLEWVSG ISVSGGITYYASSVKGRFTISRDNSKNTLYLQMNSLRAEDTAVYYCAKRG AAVGSFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYAS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 67 |
| SMT579 (D62A) HC | EVQLLESGGGLVQPGGSLRLSCAASGLTFRSYAMTWVRQAPGKGLEWVSG ISVSGGITYYAASVKGRFTISRDNSKNTLYLQMNSLRAEDTAVYYCAKRG AAVGSFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYAS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK | 43 |
| SMT578 (D62S) HC | EVQLLESGGGLVQPGGSLRLSCAASGLTFRSYAMTWVRQAPGKGLEWVSG ISVSGGITYYASSVKGRFTISRDNSKNTLYLQMNSLRAEDTAVYYCAKRG AAVGSFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYAS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 68 |
| SMT580 (S63T) HC | EVQLLESGGGLVQPGGSLRLSCAASGLTFRSYAMTWVRQAPGKGLEWVSG ISVSGGITYYADTVKGRFTISRDNSKNTLYLQMNSLRAEDTAVYYCAKRG AAVGSFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYAS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK | 44 |

TABLE 1-continued

Amino acid sequences of exemplary anti-MSLN antibodies.

| Description | Amino Acid Sequence | SEQ ID NO |
|---|---|---|
| SMT580 (S63T) HC | EVQLLESGGGLVQPGGSLRLSCAASGLTFRSYAMTWVRQAPGKGLEWVSG ISVSGGITYYADTVKGRFTISRDNSKNTLYLQMNSLRAEDTAVYYCAKRG AAVGSFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYAS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 69 |
| SMT581 (S63V) HC | EVQLLESGGGLVQPGGSLRLSCAASGLTFRSYAMTWVRQAPGKGLEWVSG ISVSGGITYYADVVKGRFTISRDNSKNTLYLQMNSLRAEDTAVYYCAKRG AAVGSFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYAS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK | 45 |
| SMT581 (S63V) HC | EVQLLESGGGLVQPGGSLRLSCAASGLTFRSYAMTWVRQAPGKGLEWVSG ISVSGGITYYADVVKGRFTISRDNSKNTLYLQMNSLRAEDTAVYYCAKRG AAVGSFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYAS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 70 |
| SMT582 (S63A) HC | EVQLLESGGGLVQPGGSLRLSCAASGLTFRSYAMTWVRQAPGKGLEWVSG ISVSGGITYYADAVKGRFTISRDNSKNTLYLQMNSLRAEDTAVYYCAKRG AAVGSFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYAS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK | 46 |
| SMT582 (S63A) HC | EVQLLESGGGLVQPGGSLRLSCAASGLTFRSYAMTWVRQAPGKGLEWVSG ISVSGGITYYADAVKGRFTISRDNSKNTLYLQMNSLRAEDTAVYYCAKRG AAVGSFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYAS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 71 |
| SMT571 (N92K) LC | DIQMTQSPSSLSASVGDRVTITCRSSQGIGSWLAWYQQKPEKAPQSLIYA ASSLQSGVPSRFSGSGSGTDFTLTISNLQPEDFATYYCQQYKSYPLTFGG GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC | 47 |
| SMT572 (N92S) LC | DIQMTQSPSSLSASVGDRVTITCRSSQGIGSWLAWYQQKPEKAPQSLIYA ASSLQSGVPSRFSGSGSGTDFTLTISNLQPEDFATYYCQQYSSYPLTFGG GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC | 48 |
| SMT573 (N92A) LC | DIQMTQSPSSLSASVGDRVTITCRSSQGIGSWLAWYQQKPEKAPQSLIYA ASSLQSGVPSRFSGSGSGTDFTLTISNLQPEDFATYYCQQYASYPLTFGG GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC | 49 |
| SMT574 (S93T) LC | DIQMTQSPSSLSASVGDRVTITCRSSQGIGSWLAWYQQKPEKAPQSLIYA ASSLQSGVPSRFSGSGSGTDFTLTISNLQPEDFATYYCQQYNTYPLTFGG GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC | 50 |

TABLE 1-continued

Amino acid sequences of exemplary anti-MSLN antibodies.

| Description | Amino Acid Sequence | SEQ ID NO |
|---|---|---|
| SMT575 (S93V) LC | DIQMTQSPSSLSASVGDRVTITCRSSQGIGSWLAWYQQKPEKAPQSLIYA ASSLQSGVPSRFSGSGSGTDFTLTISNLQPEDFATYYCQQYNVYPLTFGG GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC | 51 |
| SMT576 (S93A) LC | DIQMTQSPSSLSASVGDRVTITCRSSQGIGSWLAWYQQKPEKAPQSLIYA ASSLQSGVPSRFSGSGSGTDFTLTISNLQPEDFATYYCQQYNAYPLTFGG GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC | 52 |
| WT IgG1 heavy chain constant region | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPG | 53 |
| N297A IgG1 heavy chain constant region | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVS HEDPEVKFNWYVDGVEVHNAKTKPREEQYASTYRVVSVLTVLHQDWLNGK EYKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPG | 54 |
| LEPG IgG1 heavy chain constant region | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELEGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALGAPIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPG | 55 |
| LEASPS IgG1 heavy chain constant region | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELEGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPSSIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPG | 72 |
| N297A Ig2 heavy chain constant region | ASTKGPSVFPLAPCSRSTSESTAALGCLVKDYFPEPVTVSWNSGALTSGV HTFPAVLQSSGLYSLSSVVTVPSSNFGTQTYTCNVDHKPSNTKVDKTVER KCCVECPPCPAPPVAGPSVFLFPPKPKDTLMISRTPEVTCVVVDVSHEDP EVQFNWYVDGVEVHNAKTKPREEQFASTFRVVSVLTVVHQDWLNGKEYKC KVSNKGLPAPIEKTISKTKGQPREPQVYTLPPSREEMTKNQVSLTCLVKG FYPSDIAVEWESNGQPENNYKTTPPMLDSDGSFFLYSKLTVDKSRWQQGN VFSCSVMHEALHNHYTQKSLSLSPG | 56 |

In certain embodiments, the instant disclosure provides an antibody that specifically binds to MSLN (e.g., human MSLN), the antibody comprising a VH domain comprising one, two, or all three of the CDRs of a VH domain set forth in Table 1. In certain embodiments, the antibody comprises the CDRH1 of a VH domain set forth in Table 1. In certain embodiments, the antibody comprises the CDRH2 of a VH domain set forth in Table 1. In certain embodiments, the antibody comprises the CDRH3 of a VH domain set forth in Table 1.

In certain embodiments, the instant disclosure provides an antibody that specifically binds to MSLN (e.g., human MSLN), the antibody comprising a VL domain comprising one, two, or all three of the CDRs of a VL domain disclosed in Table 1. In certain embodiments, the antibody comprises the CDRL1 of a VL domain set forth in Table 1. In certain embodiments, the antibody comprises the CDRL2 of a VL domain set forth in Table 1. In certain embodiments, the antibody comprises the CDRL3 of a VL domain set forth in Table 1.

The individual CDRs of an antibody disclosed herein can be determined according to any CDR numbering scheme known in the art.

In certain embodiments, one or more of the CDRs of an antibody disclosed herein can be determined according to Kabat et al., J. Biol. Chem. 252, 6609-6616 (1977) and Kabat et al., Sequences of protein of immunological interest (1991), each of which is herein incorporated by reference in its entirety.

In certain embodiments, the instant disclosure provides antibodies that specifically bind to MSLN (e.g., human MSLN) and comprise CDRs of an antibody disclosed in Table 1 herein as determined by the Kabat numbering scheme.

In certain embodiments, one or more of the CDRs of an antibody disclosed herein can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226, all of which are herein incorporated by reference in their entireties).

In certain embodiments, the instant disclosure provides antibodies that specifically bind to MSLN (e.g., human MSLN) and comprise CDRs of an antibody disclosed in Table 1 herein, as determined by the Chothia numbering system.

In certain embodiments, one or more of the CDRs of an antibody disclosed herein can be determined according to MacCallum R M et al., (1996) J Mol Biol 262: 732-745, herein incorporated by reference in its entirety. See also, e.g., Martin A. "Protein Sequence and Structure Analysis of Antibody Variable Domains," in Antibody Engineering, Kontermann and Dubel, eds., Chapter 31, pp. 422-439, Springer-Verlag, Berlin (2001), herein incorporated by reference in its entirety.

In certain embodiments, the instant disclosure provides antibodies that specifically bind to MSLN (e.g., human MSLN) and comprise CDRs of an antibody disclosed in Table 1 herein, as determined by the MacCallum numbering system.

In certain embodiments, the CDRs of an antibody disclosed herein can be determined according to the IMGT numbering system as described in: Lefranc M-P, (1999) The Immunologist 7: 132-136; Lefranc M-P et al., (1999) Nucleic Acids Res 27: 209-212, each of which is herein incorporated by reference in its entirety; and Lefranc M-P et al., (2009) Nucleic Acids Res 37: D1006-D1012.

In certain embodiments, the instant disclosure provides antibodies that specifically bind to MSLN (e.g., human MSLN) and comprise CDRs of an antibody disclosed in Table 1 herein, as determined by the IMGT numbering system.

In certain embodiments, the CDRs of an antibody disclosed herein can be determined according to the AbM numbering scheme, which refers to AbM hypervariable regions, which represent a compromise between the Kabat CDRs and Chothia structural loops, and are used by Oxford Molecular's AbM antibody modeling software (Oxford Molecular Group, Inc.), herein incorporated by reference in its entirety.

In certain embodiments, the instant disclosure provides antibodies that specifically bind to MSLN (e.g., human MSLN) and comprise CDRs of an antibody disclosed in Table 1 herein as determined by the AbM numbering scheme.

In certain embodiments, the CDRs of an antibody disclosed herein can be determined according to the AHo numbering system, as described in Honegger and Pluckthun, A., J. Mol. Biol. 309:657-670 (2001), herein incorporated by reference in its entirety.

In certain embodiments, the instant disclosure provides antibodies that specifically bind to MSLN (e.g., human MSLN) and comprise CDRs of an antibody disclosed in Table 1 herein, as determined by the AHo numbering system.

In certain embodiments, the individual CDRs of an antibody disclosed herein are each independently determined according to one of the Kabat, Chothia, MacCallum, IMGT, AHo, or AbM numbering schemes, or by structural analysis of the multispecific molecule, wherein the structural analysis identifies residues in the variable region(s) predicted to make contact with an epitope region of MSLN.

In certain embodiments, the instant disclosure provides an antibody that specifically bind MSLN (e.g., human MSLN) comprising a VH comprising the CDRH1, CDRH2, and CDRH3 amino acid sequences of the VH amino acid sequence set forth in SEQ ID NO: 11, and a VL comprising the CDRL1, CDRL2, and CDRL3 amino acid sequences of the VL amino acid sequence set forth in SEQ ID NO: 12, wherein each CDR is independently determined according to one of the Kabat, Chothia, MacCallum, IMGT, AHo, or AbM numbering schemes, or by structural analysis of the multispecific molecule, wherein the structural analysis identifies residues in the variable region(s) predicted to make contact with an epitope region of MSLN (e.g., human MSLN). In some embodiments, the antibody does not comprise SEQ ID NO: 4 and/or SEQ ID NO: 8.

In certain embodiments, the instant disclosure provides an antibody that specifically binds to MSLN (e.g., human MSLN), wherein the antibody comprises a VH comprising the CDRH1, CDRH2 and CDRH3 amino acid sequences set forth in SEQ ID NOs: 3, 13, and 5, respectively.

In certain embodiments, the instant disclosure provides an antibody that specifically binds to MSLN (e.g., human MSLN), wherein the antibody comprises a VL comprising the CDRL1, CDRL2, and CDRL3 amino acid sequences set forth in SEQ ID NOs: 6, 7, and 14, respectively.

In certain embodiments, the instant disclosure provides an antibody that specifically binds to MSLN (e.g., human MSLN), wherein the antibody comprises a VH comprising CDRH1, CDRH2, and CDRH3 regions, and a VL comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 3, 13, 5, 6, 7, and 14, respectively.

In certain embodiments, the instant disclosure provides an antibody that specifically binds to MSLN (e.g., human MSLN), wherein the antibody comprises the CDRH1, CDRH2, and CDRH3 amino acid sequences, set forth in SEQ ID NOs: 3, 29, and 5; 3, 30, and 5; 3, 31, and 5; 3, 32, and 5; 3, 33, and 5; or 3, 34, and 5, respectively.

In certain embodiments, the instant disclosure provides an antibody that specifically binds to MSLN (e.g., human MSLN), wherein the antibody comprises the CDRL1, CDRL2, and CDRL3 amino acid sequences, set forth in SEQ ID NOs: 6, 7, and 35; 6, 7, and 36; 6, 7, and 37; 6, 7, and 38; 6, 7, and 39; or 6, 7, and 40, respectively.

In certain embodiments, the instant disclosure provides an antibody that specifically binds to MSLN (e.g., human MSLN), wherein the antibody comprises the CDRH1, CDRH2, CDRH3, CDRL1, CDRL2, and CDRL3 amino acid sequences, set forth in SEQ ID NOs: 3, 29, 5, 6, 7, and 35; 3, 29, 5, 6, 7, and 36; 3, 29, 5, 6, 7, and 37; 3, 29, 5, 6, 7, and 38; 3, 29, 5, 6, 7, and 39; 3, 29, 5, 6, 7, and 40; 3, 30, 5, 6, 7, and 35; 3, 30, 5, 6, 7, and 36; 3, 30, 5, 6, 7, and 37; 3, 30, 5, 6, 7, and 38; 3, 30, 5, 6, 7, and 39; 3, 30, 5, 6, 7, and 40; 3, 31, 5, 6, 7, and 35; 3, 31, 5, 6, 7, and 36; 3, 31, 5, 6, 7, and 37; 3, 31, 5, 6, 7, and 38; 3, 31, 5, 6, 7, and 39; 3, 31, 5, 6, 7, and 40; 3, 32, 5, 6, 7, and 35; 3, 32, 5, 6, 7, and 36; 3, 32, 5, 6, 7, and 37; 3, 32, 5, 6, 7, and 38; 3, 32, 5, 6, 7, and 39; 3, 32, 5, 6, 7, and 40; 3, 33, 5, 6, 7, and 35; 3, 33, 5, 6, 7, and 36; 3, 33, 5, 6, 7, and 37; 3, 33, 5, 6, 7, and 38; 3, 33, 5, 6, 7, and 39; 3, 33, 5, 6, 7, and 40; 3, 34, 5, 6, 7, and 35; 3, 34, 5, 6, 7, and 36; 3, 34, 5, 6, 7, and 37; 3, 34, 5, 6, 7, and 38; 3, 34, 5, 6, 7, and 39; or 3, 34, 5, 6, 7, and 40, respectively.

In certain embodiments, the instant disclosure provides an antibody that specifically binds to MSLN (e.g., human MSLN) comprising a VH comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 11. In certain embodiments, the instant disclosure provides an antibody that specifically binds to MSLN (e.g., human MSLN), comprising a VH comprising an amino acid sequence set forth in SEQ ID NO: 11. In certain embodiments, the amino acid sequence of the VH consists of the amino acid sequence set forth in SEQ ID NO: 11.

In certain embodiments, the instant disclosure provides an antibody that specifically binds to MSLN (e.g., human MSLN), comprising a VL comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 12. In certain embodiments, the instant disclosure provides an antibody that specifically binds to MSLN (e.g., human MSLN), comprising a VL comprising an amino acid sequence set forth in SEQ ID NO: 12. In certain embodiments, the amino acid sequence of the VL consists of the amino acid sequence set forth in SEQ ID NO: 12.

In certain embodiments, the instant disclosure provides an antibody that specifically binds to MSLN (e.g., human MSLN), comprising a VH comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 11, and a VL comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 12. In certain embodiments, the instant disclosure provides an antibody that specifically binds to MSLN (e.g., human MSLN), comprising a VH comprising an amino acid sequence of SEQ ID NO: 11, and a VL comprising an amino acid sequence of SEQ ID NO: 12. In certain embodiments, the amino acid sequence of the VH consists of the amino acid sequence set forth in SEQ ID NO: 11; and the amino acid sequence of the VL consists of the amino acid sequence set forth in SEQ ID NO: 12.

In certain embodiments, the instant disclosure provides an antibody that specifically binds to MSLN (e.g., human MSLN), comprising the VH and VL amino acid sequences set forth in SEQ ID NOs: 11 and 12, respectively. In certain embodiments, the amino acid sequences of VH and VL consist of the amino acid sequences set forth in SEQ ID NOs: 11 and 12, respectively.

In certain embodiments, the instant disclosure provides an antibody that specifically binds to MSLN (e.g., human MSLN), comprising a VH amino acid sequence of SEQ ID NO: 17, 18, 19, 20, 21, or 22. In certain embodiments, the instant disclosure provides an antibody that specifically binds to MSLN (e.g., human MSLN), consisting of a VH amino acid sequence of SEQ ID NO: 17, 18, 19, 20, 21, or 22.

In certain embodiments, the instant disclosure provides an antibody that specifically binds to MSLN (e.g., human MSLN), comprising a VL amino acid sequence of SEQ ID NO: 23, 24, 25, 26, 27, or 28. In certain embodiments, the instant disclosure provides an antibody that specifically binds to MSLN (e.g., human MSLN), consisting of a VL amino acid sequence of SEQ ID NO: 23, 24, 25, 26, 27, or 28.

In certain embodiments, the instant disclosure provides an antibody that specifically binds to MSLN (e.g., human MSLN), wherein the VH and VL comprise the amino acid sequences set forth in SEQ ID NOs: 17 and 23, 17 and 24, 17 and 25, 17 and 26, 17 and 27, 17 and 28, 18 and 23, 18 and 24, 18 and 25, 18 and 26, 18 and 27, 18 and 28, 19 and 23, 19 and 24, 19 and 25, 19 and 26, 19 and 27, 19 and 28, 20 and 23, 20 and 24, 20 and 25, 20 and 26, 20 and 27, 20 and 28, 21 and 23, 21 and 24, 21 and 25, 21 and 26, 21 and 27, 21 and 28, 22 and 23, 22 and 24, 22 and 25, 22 and 26, 22 and 27, or 22 and 28, respectively. In certain embodiments, the instant disclosure provides an antibody that specifically binds to MSLN (e.g., human MSLN), wherein the VH and VL consist of the amino acid sequences set forth in SEQ ID NOs: 17 and 23, 17 and 24, 17 and 25, 17 and 26, 17 and 27, 17 and 28, 18 and 23, 18 and 24, 18 and 25, 18 and 26, 18 and 27, 18 and 28, 19 and 23, 19 and 24, 19 and 25, 19 and 26, 19 and 27, 19 and 28, 20 and 23, 20 and 24, 20 and 25, 20 and 26, 20 and 27, 20 and 28, 21 and 23, 21 and 24, 21 and 25, 21 and 26, 21 and 27, 21 and 28, 22 and 23, 22 and 24, 22 and 25, 22 and 26, 22 and 27, or 22 and 28, respectively.

In certain embodiments, the instant disclosure provides an antibody that cross-competes for binding to MSLN (e.g., human MSLN) with an antibody comprising the VH and VL amino acid sequences set forth in SEQ ID NOs: 11 and 12, respectively. In certain embodiments, the instant disclosure provides an antibody that cross-competes for binding to MSLN (e.g., human MSLN) with an antibody comprising the VH and VL amino acid sequences set forth in SEQ ID NOs: 17 and 23, 17 and 24, 17 and 25, 17 and 26, 17 and 27, 17 and 28, 18 and 23, 18 and 24, 18 and 25, 18 and 26, 18 and 27, 18 and 28, 19 and 23, 19 and 24, 19 and 25, 19 and 26, 19 and 27, 19 and 28, 20 and 23, 20 and 24, 20 and 25, 20 and 26, 20 and 27, 20 and 28, 21 and 23, 21 and 24, 21 and 25, 21 and 26, 21 and 27, 21 and 28, 22 and 23, 22 and 24, 22 and 25, 22 and 26, 22 and 27, or 22 and 28, respectively.

In certain embodiments, the instant disclosure provides an antibody that binds to the same or an overlapping epitope of MSLN (e.g., an epitope of human MSLN) as an antibody described herein, e.g., an antibody comprising the VH and VL amino acid sequences set forth in SEQ ID NOs: 11 and 12, respectively. In certain embodiments, the instant disclosure provides an antibody that binds to the same or an overlapping epitope of MSLN (e.g., an epitope of human MSLN) as an antibody described herein, e.g., an antibody comprising the VH and VL amino acid sequences set forth in SEQ ID NOs: 17 and 23, 17 and 24, 17 and 25, 17 and 26, 17 and 27, 17 and 28, 18 and 23, 18 and 24, 18 and 25, 18 and 26, 18 and 27, 18 and 28, 19 and 23, 19 and 24, 19 and 25, 19 and 26, 19 and 27, 19 and 28, 20 and 23, 20 and 24, 20 and 25, 20 and 26, 20 and 27, 20 and 28, 21 and 23, 21 and 24, 21 and 25, 21 and 26, 21 and 27, 21 and 28, 22 and 23, 22 and 24, 22 and 25, 22 and 26, 22 and 27, or 22 and 28, respectively.

In certain embodiments, the epitope of an antibody can be determined by, e.g., NMR spectroscopy, surface plasmon resonance (BIAcore®), X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303, all of which are herein incorporated by reference in their entireties). Antibody:antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.; U.S. Patent Application No. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323, all of which are herein incorporated by reference in their entireties). Mutagenesis mapping studies may be accomplished using any method known to one of skill in the art. See, e.g., Champe M et al., (1995) supra and Cunningham B C & Wells J A (1989) supra for a description of mutagenesis techniques, including alanine scanning mutagenesis techniques. In a specific embodiment, the epitope of an antibody is determined using alanine scanning mutagenesis studies. In addition, or antibodies that recognize and bind to the same or overlapping epitopes of MSLN (e.g., human MSLN) can be identified using routine techniques such as an immunoassay, for example, by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as MSLN (e.g., human MSLN). Numerous types of competitive binding assays are known, for example: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using I-125 label (see Morel G A et al., (1988) Mol Immunol 25(1): 7-15); solid phase direct biotin-avidin EIA (see Cheung R C et al., (1990) Virology 176: 546-52); and direct labeled RIA (see Moldenhauer G et al., (1990) Scand J Immunol 32: 77-82), all of which are herein incorporated by reference in their entireties. Typically, such an assay involves the use of purified antigen (e.g., MSLN, such as human MSLN) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually, the test immunoglobulin is present in excess. Usually, when a competing antibody is present in excess, it will inhibit specific binding of a reference or antibody to a common antigen by at least 50-55%, 55-60%, 60-65%, 65-70%, 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors supra, pp. 386-389, all of which are herein incorporated by reference in their entireties.

In certain embodiments, the instant disclosure provides an antibody that specifically binds to MSLN (e.g., human MSLN), the antibody comprising a heavy chain comprising the amino acid sequence set forth in SEQ ID NO: 83, 84, 41, 42, 43, 44, 45, 46, 66, 67, 68, 69, 70, or 71. In certain embodiments, the amino acid sequence of the heavy chain consists of the amino acid sequence set forth in SEQ ID NO: 83, 84, 41, 42, 43, 44, 45, 46, 66, 67, 68, 69, 70, or 71.

In certain embodiments, the instant disclosure provides an antibody that specifically binds to MSLN (e.g., human MSLN), the antibody comprising a light chain comprising the amino acid sequence set forth in SEQ ID NO: 47, 48, 49, 50, 51, or 52. In certain embodiments, the amino acid sequence of the light chain consists of an amino acid sequence selected from the group consisting of SEQ ID NO: 47, 48, 49, 50, 51, or 52.

In certain embodiments, the instant disclosure provides an antibody that specifically binds to MSLN (e.g., human MSLN), comprising the heavy chain and light chain, wherein the heavy chain and light chain comprise the amino acid sequences of SEQ ID NOs: 83 and 48, 84 and 48, 83 and 49, 84 and 49, 83 and 50, 84 and 50, 83 and 51, 84 and 51, 83 and 52, 84 and 52, 83 and 47, 84 and 47, 41 and 47, 41 and 48, 41 and 49, 41 and 50, 41 and 51, 41 and 52, 42 and 47, 42 and 48, 42 and 49, 42 and 50, 42 and 51, 42 and 52, 43 and 47, 43 and 48, 43 and 49, 43 and 50, 43 and 51, 43 and 52, 44 and 47, 44 and 48, 44 and 49, 44 and 50, 44 and 51, 44 and 52, 45 and 47, 45 and 48, 45 and 49, 45 and 50, 45 and 51, 45 and 52, 46 and 47, 46 and 48, 46 and 49, 46 and 50, 46 and 51, 46 and 52, 66 and 47, 66 and 48, 66 and 49, 66 and 50, 66 and 51, 66 and 52, 67 and 47, 67 and 48, 67 and 49, 67 and 50, 67 and 51, 67 and 52, 68 and 47, 68 and 48, 68 and 49, 68 and 50, 68 and 51, 68 and 52, 69 and 47, 69 and 48, 69 and 49, 69 and 50, 69 and 51, 69 and 52, 70 and 47, 70 and 48, 70 and 49, 70 and 50, 70 and 51, 70 and 52, 71 and 47, 71 and 48, 71 and 49, 71 and 50, 71 and 51, or 71 and 52, respectively.

In certain embodiments, the amino acid sequences of the heavy chain and light chain consist of amino acid sequences selected from the groups consisting of SEQ ID NOs: 83 and 48, 84 and 48, 83 and 49, 84 and 49, 83 and 50, 84 and 50, 83 and 51, 84 and 51, 83 and 52, 84 and 52, 83 and 47, 84 and 47, 41 and 47, 41 and 48, 41 and 49, 41 and 50, 41 and 51, 41 and 52, 42 and 47, 42 and 48, 42 and 49, 42 and 50, 42 and 51, 42 and 52, 43 and 47, 43 and 48, 43 and 49, 43 and 50, 43 and 51, 43 and 52, 44 and 47, 44 and 48, 44 and 49, 44 and 50, 44 and 51, 44 and 52, 45 and 47, 45 and 48, 45 and 49, 45 and 50, 45 and 51, 45 and 52, 46 and 47, 46 and 48, 46 and 49, 46 and 50, 46 and 51, 46 and 52, 66 and 47, 66 and 48, 66 and 49, 66 and 50, 66 and 51, 66 and 52, 67 and 47, 67 and 48, 67 and 49, 67 and 50, 67 and 51, 67 and 52, 68 and 47, 68 and 48, 68 and 49, 68 and 50, 68 and 51, 68 and 52, 69 and 47, 69 and 48, 69 and 49, 69 and 50, 69 and 51, 69 and 52, 70 and 47, 70 and 48, 70 and 49, 70 and 50, 70 and 51, 70 and 52, 71 and 47, 71 and 48, 71 and 49, 71 and 50, 71 and 51, or 71 and 52, respectively.

In certain embodiments, the instant disclosure provides antibodies that specifically bind to MSLN (e.g., human MSLN) and a T cell antigen (e.g., CD3).

In certain embodiments, the instant disclosure provides an antibody that specifically binds to MSLN (e.g., human MSLN), and further comprises a CD3 binding moiety. Any CD3 binding moiety known in the art may be used in the antibodies and polypeptides disclosed herein, including, without limitation, polypeptides, aptamers, and small molecule CD3 binding moieties. In certain embodiments, the CD3 binding moiety is an antibody. In certain embodiments, the CD3 binding moiety is a single-chain fragment variable (scFv). The VH and VL amino acid sequences of exemplary anti-CD3 antibodies (e.g., scFv) are set forth in Table 2.

TABLE 2

Amino acid sequences of exemplary anti-CD3 binding moieties, linkers, and anti-MSLN antibodies comprising anti-CD3 binding moieties.

| Description | Amino Acid Sequence | SEQ ID NO |
|---|---|---|
| Micro194 VH | EVQLVESGGGLVQPGGSLKLSCAASGFTFNTYAMNWVRQAPGKG LEWVARIRSKYNNYATYYADSVKDRFTISRDDSKNTAYLQMNNL KTEDTAVYYCVRHGNFGNSYVSWFAYWGQGTLVTVSS | 57 |
| Micro194 VL | QTVVTQEPSLTVSPGGTVTLTCRSSTGAVTTSNYANWVQQKPGQ APRGLIGGTNKRAPGTPARFSGSLLGGKAALTLSGVQPEDEAEY YCALWYSNLWVFGGGTKLTVL | 58 |
| Humanized OKT3 VH | QVQLVQSGGGVVQPGRSLRLSCKASGYTFTRYTMHWVRQAPGKG LEWIGYINPSRGYTNYNQKFKDRFTISRDNSKNTAFLQMDSLRP EDTGVYFCARYYDDHYSLDYWGQGTPVTVSS | 59 |
| Humanized OKT3 VL | DIQMTQSPSSLSASVGDRVTITCSASSSVSYMNWYQQTPGKAPK RWIYDTSKLASGVPSRFSGSGSGTDYTFTISSLQPEDIATYYCQ QWSSNPFTFGQGTKLQITR | 60 |
| Humanized UCHT1 VH | EVQLVESGGGLVQPGGSLRLSCAASGYSFTGYTMNWVRQAPGKG LEWVALINPYKGVTTYADSVKGRFTISVDKSKNTAYLQMNSLRA EDTAVYYCARSGYYGDSDWYFDVWGQGTLVTVSS | 61 |
| Humanized UCHT1 VL | DIQMTQSPSSLSASVGDRVTITCRASQDIRNYLNWYQQKPGKAP KLLIYYTSRLESGVPSRFSGSGSGTDYTLTISSLQPEDFATYYC QQGNTLPWTFGQGTKVEIK | 62 |
| GGGS linker sequence | (GGGS)$_n$ $n$ = 1, 2, 3, or 4 | 63 |
| GGGGS linker sequence | (GGGGS)$_n$ $n$ = 1, 2, 3, or 4 | 64 |
| Linker sequence | GGGGSGGGSGGGSGGGG | 73 |
| Linker sequence | GGGSGGGGSGGGGSGGG | 74 |
| Linker sequence | GGGGSGGGSGGGG | 75 |
| Micro194 scFv | EVQLVESGGGLVQPGGSLKLSCAASGFTFNTYAMNWVRQAPGKG LEWVARIRSKYNNYATYYADSVKDRFTISRDDSKNTAYLQMNNL KTEDTAVYYCVRHGNFGNSYVSWFAYWGQGTLVTVSSGGGGSGG GSGGGGSGGGGQTVVTQEPSLTVSPGGTVTLTCRSSTGAVTTSNY ANWVQQKPGQAPRGLIGGTNKRAPGTPARFSGSLLGGKAALTLS GVQPEDEAEYYCALWYSNLWVFGGGTKLTVL | 76 |
| M-3654 full length light chain (SMT571 (N92K) LC + linker + Micro194 scFv) | DIQMTQSPSSLSASVGDRVTITCRSSQGIGSWLAWYQQKPEKAP QSLIYAASSLQSGVPSRFSGSGSGTDFTLTISNLPEDFATYYC QQYKSYPLTFGGGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGECGGGGSG GGSGGGSGGGGEVQLVESGGGLVQPGGSLKLSCAASGFTFNTYA MNWVRQAPGKGLEWVARIRSKYNNYATYYADSVKDRFTISRDDS KNTAYLQMNNLKTEDTAVYYCVRHGNFGNSYVSWFAYWGQGTLV TVSSGGGGSGGGSGGGSGGGGQTVVTQEPSLTVSPGGTVTLTCR SSTGAVTTSNYANWVQQKPGQAPRGLIGGTNKRAPGTPARFSGS LLGGKAALTLSGVQPEDEAEYYCALWYSNLWVFGGGTKLTVL | 77 |
| SMT572 (N92S) LC + linker + Micro194 scFv | DIQMTQSPSSLSASVGDRVTITCRSSQGIGSWLAWYQQKPEKAP QSLIYAASSLQSGVPSRFSGSGSGTDFTLTISNLPEDFATYYC QQYSSYPLTFGGGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGECGGGGSG GGSGGGSGGGGEVQLVESGGGLVQPGGSLKLSCAASGFTFNTYA MNWVRQAPGKGLEWVARIRSKYNNYATYYADSVKDRFTISRDDS | 78 |

TABLE 2-continued

Amino acid sequences of exemplary anti-CD3 binding moieties, linkers, and anti-MSLN antibodies comprising anti-CD3 binding moieties.

| Description | Amino Acid Sequence | SEQ ID NO |
|---|---|---|
| | KNTAYLQMNNLKTEDTAVYYCVRHGNFGNSYVSWFAYWGQGTLV TVSSGGGGSGGGSGGGSGGGGQTVVTQEPSLTVSPGGTVTLTCR SSTGAVTTSNYANWVQQKPGQAPRGLIGGTNKRAPGTPARFSGS LLGGKAALTLSGVQPEDEAEYYCALWYSNLWVFGGGTKLTVL | |
| SMT573 (N92A) LC + linker + Micro194 scFv | DIQMTQSPSSLSASVGDRVTITCRSSQGIGSWLAWYQQKPEKAP QSLIYAASSLQSGVPSRFSGSGSGTDFTLTISNLQPEDFATYYC QQYASYPLTFGGGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGECGGGGSG GGSGGGSGGGGEVQLVESGGGLVQPGGSLKLSCAASGFTFNTYA MNWVRQAPGKGLEWVARIRSKYNNYATYYADSVKDRFTISRDDS KNTAYLQMNNLKTEDTAVYYCVRHGNFGNSYVSWFAYWGQGTLV TVSSGGGGSGGGSGGGSGGGGQTVVTQEPSLTVSPGGTVTLTCR SSTGAVTTSNYANWVQQKPGQAPRGLIGGTNKRAPGTPARFSGS LLGGKAALTLSGVQPEDEAEYYCALWYSNLWVFGGGTKLTVL | 79 |
| SMT574 (S93T) LC + linker + Micro194 scFv | DIQMTQSPSSLSASVGDRVTITCRSSQGIGSWLAWYQQKPEKAP QSLIYAASSLQSGVPSRFSGSGSGTDFTLTISNLQPEDFATYYC QQYNTYPLTFGGGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGECGGGGSG GGSGGGSGGGGEVQLVESGGGLVQPGGSLKLSCAASGFTFNTYA MNWVRQAPGKGLEWVARIRSKYNNYATYYADSVKDRFTISRDDS KNTAYLQMNNLKTEDTAVYYCVRHGNFGNSYVSWFAYWGQGTLV TVSSGGGGSGGGSGGGSGGGGQTVVTQEPSLTVSPGGTVTLTCR SSTGAVTTSNYANWVQQKPGQAPRGLIGGTNKRAPGTPARFSGS LLGGKAALTLSGVQPEDEAEYYCALWYSNLWVFGGGTKLTVL | 80 |
| SMT575 (S93V) LC + linker + Micro194 scFv | DIQMTQSPSSLSASVGDRVTITCRSSQGIGSWLAWYQQKPEKAP QSLIYAASSLQSGVPSRFSGSGSGTDFTLTISNLQPEDFATYYC QQYNVYPLTFGGGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGECGGGGSG GGSGGGSGGGGEVQLVESGGGLVQPGGSLKLSCAASGFTFNTYA MNWVRQAPGKGLEWVARIRSKYNNYATYYADSVKDRFTISRDDS KNTAYLQMNNLKTEDTAVYYCVRHGNFGNSYVSWFAYWGQGTLV TVSSGGGGSGGGSGGGSGGGGQTVVTQEPSLTVSPGGTVTLTCR SSTGAVTTSNYANWVQQKPGQAPRGLIGGTNKRAPGTPARFSGS LLGGKAALTLSGVQPEDEAEYYCALWYSNLWVFGGGTKLTVL | 81 |
| SMT576 (S93A) LC + linker + Micro194 scFv | DIQMTQSPSSLSASVGDRVTITCRSSQGIGSWLAWYQQKPEKAP QSLIYAASSLQSGVPSRFSGSGSGTDFTLTISNLQPEDFATYYC QQYNAYPLTFGGGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGECGGGGSG GGSGGGSGGGGEVQLVESGGGLVQPGGSLKLSCAASGFTFNTYA MNWVRQAPGKGLEWVARIRSKYNNYATYYADSVKDRFTISRDDS KNTAYLQMNNLKTEDTAVYYCVRHGNFGNSYVSWFAYWGQGTLV TVSSGGGGSGGGSGGGSGGGGQTVVTQEPSLTVSPGGTVTLTCR SSTGAVTTSNYANWVQQKPGQAPRGLIGGTNKRAPGTPARFSGS LLGGKAALTLSGVQPEDEAEYYCALWYSNLWVFGGGTKLTVL | 82 |
| M-3654 full length heavy chain (SMT578 (D62S) VH + IgG1 LEPG) | EVQLLESGGGLVQPGGSLRLSCAASGLTFRSYAMTWVRQAPGKG LEWVSGISVSGGITYYASSVKGRFTISRDNSKNTLYLQMNSLRA EDTAVYYCAKRGAAVGSFDYWGQGTLVTVSSASTKGPSVFPLAP SSKSTSGGTAALGCLVKDYFPEPVTVSWNSGALTSGVHTFPAVL QSSGLYSLSSVVTVPSSSLGTQTYICNVNHKPSNTKVDKKVEPK SCDKTHTCPPCPAPELEGGPSVFLFPPKPKDTLMISRTPEVTCV VVDVSHEDPEVKFNWYVDGVEVHNAKTKPREEQYNSTYRVVSVL TVLHQDWLNGKEYKCKVSNKALGAPIEKTISKAKGQPREPQVYT LPPSRDELTKNQVSLTCLVKGFYPSDIAVEWESNGQPENNYKTT PPVLDSDGSFFLYSKLTVDKSRWQQGNVFSCSVMHEALHNHYTQ KSLSLSPGK | 83 |
| M-3654 full length heavy chain (SMT578 (D62S) VH + IgG1 LEPG) without terminal lysine | EVQLLESGGGLVQPGGSLRLSCAASGLTFRSYAMTWVRQAPGKG LEWVSGISVSGGITYYASSVKGRFTISRDNSKNTLYLQMNSLRA EDTAVYYCAKRGAAVGSFDYWGQGTLVTVSSASTKGPSVFPLAP SSKSTSGGTAALGCLVKDYFPEPVTVSWNSGALTSGVHTFPAVL QSSGLYSLSSVVTVPSSSLGTQTYICNVNHKPSNTKVDKKVEPK SCDKTHTCPPCPAPELEGGPSVFLFPPKPKDTLMISRTPEVTCV VVDVSHEDPEVKFNWYVDGVEVHNAKTKPREEQYNSTYRVVSVL | 84 |

TABLE 2-continued

Amino acid sequences of exemplary anti-CD3 binding moieties, linkers, and anti-MSLN antibodies comprising anti-CD3 binding moieties.

| Description | Amino Acid Sequence | SEQ ID NO |
|---|---|---|
| | TVLHQDWLNGKEYKCKVSNKALGAPIEKTISKAKGQPREPQVYT LPPSRDELTKNQVSLTCLVKGFYPSDIAVEWESNGQPENNYKTT PPVLDSDGSFFLYSKLTVDKSRWQQGNVFSCSVMHEALHNHYTQ KSLSLSPG | |

In certain embodiments, the CD3 binding moiety is an anti-CD3 antibody (e.g., scFv) comprising the amino acid sequence set forth in SEQ ID NO: 76. In certain embodiments, the amino acid sequence of the CD3 binding moiety consists of the amino acid sequence set forth in SEQ ID NO: 76.

In certain embodiments, the CD3 binding moiety is covalently linked to the light chain. In certain embodiments, the CD3 binding moiety is covalently linked to the C-terminus of the light chain. In certain embodiments, the CD3 binding moiety is covalently linked to the C-terminus of the light chain via a peptide linker. In certain embodiments, the peptide linker comprises the amino acid sequence set forth in SEQ ID NO: 63, 64, 73, 74, or 75.

In certain embodiments, the antibody that specifically binds to MSLN (e.g., human MSLN), and further comprises a CD3 binding moiety has a light chain comprising an amino acid sequence set forth in any one of SEQ ID NOs: 77, 78, 79, 80, 81, or 82. In certain embodiments, the antibody that specifically binds to MSLN (e.g., human MSLN), and further comprises a CD3 binding moiety has a light chain consisting of an amino acid sequence set forth in any one of SEQ ID NOs: 77, 78, 79, 80, 81, or 82.

In certain embodiments, the antibody that specifically binds to MSLN (e.g., human MSLN), and further comprises a CD3 binding moiety comprises a heavy chain and a light chain comprising the amino acid sequences, respectively, set forth in SEQ ID NOs: 83 and 77, 84 and 77, 41 and 77, 42 and 77, 43 and 77, 44 and 77, 45 and 77, 46 and 77, 66 and 77, 67 and 77, 68 and 77, 69 and 77, 70 and 77, 71 and 77, 83 and 78, 84 and 78, 41 and 78, 42 and 78, 43 and 78, 44 and 78, 45 and 78, 46 and 78, 66 and 78, 67 and 78, 68 and 78, 69 and 78, 70 and 78, 71 and 78, 83 and 79, 84 and 79, 41 and 79, 42 and 79, 43 and 79, 44 and 79, 45 and 79, 46 and 79, 66 and 79, 67 and 79, 68 and 79, 69 and 79, 70 and 79, 71 and 79, 83 and 80, 84 and 80, 41 and 80, 42 and 80, 43 and 80, 44 and 80, 45 and 80, 46 and 80, 66 and 80, 67 and 80, 68 and 80, 69 and 80, 70 and 80, 71 and 80, 83 and 81, 84 and 81, 41 and 81, 42 and 81, 43 and 81, 44 and 81, 45 and 81, 46 and 81, 66 and 81, 67 and 81, 68 and 81, 69 and 81, 70 and 81, 71 and 81, 83 and 82, 84 and 82, 41 and 82, 42 and 82, 43 and 82, 44 and 82, 45 and 82, 46 and 82, 66 and 82, 67 and 82, 68 and 82, 69 and 82, 70 and 82, or 71 and 82.

In certain embodiments, the antibody that specifically binds to MSLN (e.g., human MSLN), and further comprises a CD3 binding moiety comprises a heavy chain and a light chain consisting of the amino acid sequences, respectively, set forth in SEQ ID NOs: 83 and 77, 84 and 77, 41 and 77, 42 and 77, 43 and 77, 44 and 77, 45 and 77, 46 and 77, 66 and 77, 67 and 77, 68 and 77, 69 and 77, 70 and 77, 71 and 77, 83 and 78, 84 and 78, 41 and 78, 42 and 78, 43 and 78, 44 and 78, 45 and 78, 46 and 78, 66 and 78, 67 and 78, 68 and 78, 69 and 78, 70 and 78, 71 and 78, 83 and 79, 84 and 79, 41 and 79, 42 and 79, 43 and 79, 44 and 79, 45 and 79, 46 and 79, 66 and 79, 67 and 79, 68 and 79, 69 and 79, 70 and 79, 71 and 79, 83 and 80, 84 and 80, 41 and 80, 42 and 80, 43 and 80, 44 and 80, 45 and 80, 46 and 80, 66 and 80, 67 and 80, 68 and 80, 69 and 80, 70 and 80, 71 and 80, 83 and 81, 84 and 81, 41 and 81, 42 and 81, 43 and 81, 44 and 81, 45 and 81, 46 and 81, 66 and 81, 67 and 81, 68 and 81, 69 and 81, 70 and 81, 71 and 81, 83 and 82, 84 and 82, 41 and 82, 42 and 82, 43 and 82, 44 and 82, 45 and 82, 46 and 82, 66 and 82, 67 and 82, 68 and 82, 69 and 82, 70 and 82, or 71 and 82.

In certain embodiments, the antibody that specifically binds to MSLN (e.g., human MSLN), and further comprises a CD3 binding moiety comprises a heavy chain and a light chain comprising the amino acid sequences, respectively, set forth in SEQ ID NOs: 83 and 77. In certain embodiments, the antibody that specifically binds to MSLN (e.g., human MSLN), and further comprises a CD3 binding moiety comprises a heavy chain and a light chain consisting of the amino acid sequences, respectively, set forth in SEQ ID NOs: 83 and 77.

Figure 4:
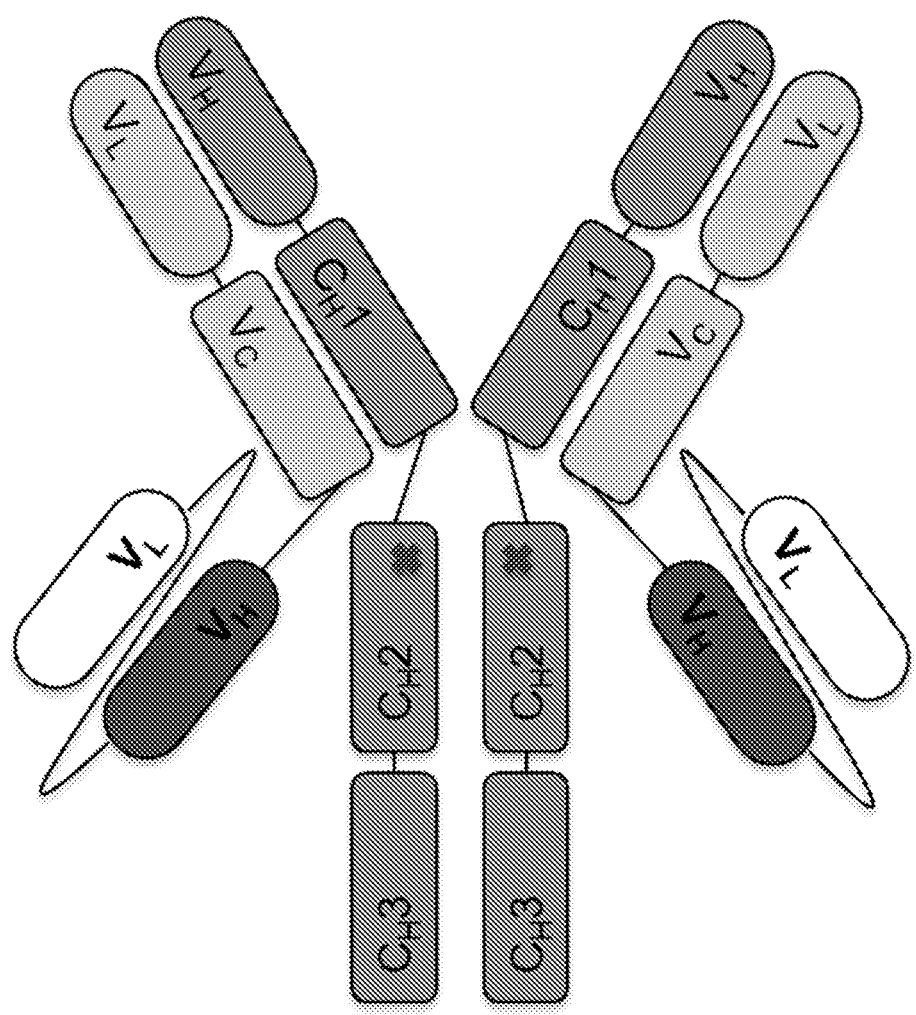
FIG. 4 is a schematic of a bispecific IgG-scFv antibody comprising Fab domains (e.g., anti-cancer Fab domains) linked to scFv domains (e.g., anti-T cell scFv domains) and an immunoglobulin Fc domain. The crosses shown in the CH2 domains represent optional mutations which inhibit interaction of the antibody with Fc receptors.

In certain embodiments, the antibody that specifically binds to MSLN (e.g., human MSLN), and further comprises a CD3 binding moiety is a bispecific antigen-binding molecule having the structure of FIG. 4. The molecules having the structure of FIG. 4 are both bispecific and bivalent for each of the target antigens (e.g., MSLN and CD3), and are also referred to herein as IgG-scFv molecules. These molecules comprise a conventional monospecific antibody structure in which the antigen-binding domains are specific for MSLN, but also include two scFv domains covalently linked to the C-terminus of the two light chain constant regions, respectively, in which the scFv domains are oriented in a VH-VL orientation (i.e., the VH portion of each of the two scFv domains is covalently linked to the C-terminus of the respective light chain constant region), and which are specific for a T cell antigen (TCA) (e.g., CD3). In any of the bispecific molecules disclosed herein, including those having the structures of FIG. 4, the anti-cancer or anti-MSLN antigen-binding domain(s) may be derived from any of the anti-MSLN antibodies disclosed herein. For example, the anti-MSLN antigen-binding domains may comprise the CDRs and/or the variable regions of the anti-MSLN antibodies disclosed herein. The anti-MSLN monospecific antibodies or anti-MSLN×anti-TCA (e.g., CD3) bispecific antigen-binding molecules of the present disclosure can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bispecific or a multispecific antibody with a second or additional binding specificity.

In certain embodiments, the antibody disclosed herein is conjugated to a cytotoxic agent, cytostatic agent, toxin, radionuclide, or detectable label. In certain embodiments, the cytotoxic agent is able to induce death or destruction of a cell in contact therewith. In certain embodiments, the cytostatic agent is able to prevent or substantially reduce proliferation and/or inhibits the activity or function of a cell in contact therewith. In certain embodiments, the cytotoxic agent or cytostatic agent is a chemotherapeutic agent. In certain embodiments, the radionuclide is selected from the group consisting of the isotopes $^{3}$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac, and $^{186}$Re. In certain embodiments, the detectable label comprises a fluorescent moiety or a click chemistry handle.

Any immunoglobulin (Ig) constant region can be used in the antibodies disclosed herein. In certain embodiments, the Ig region is a human IgG, IgE, IgM, IgD, IgA, or IgY immunoglobulin molecule, any class (e.g., $IgG_1$, $IgG_2$, $IgG_3$, $IgG_4$, $IgA_1$, and $IgA_2$), or any subclass (e.g., $IgG_2$a and $IgG_2$b) of immunoglobulin molecule.

In certain embodiments, the instant disclosure provides an antibody that specifically binds to MSLN (e.g., human MSLN), the antibody comprising a heavy chain constant region, optionally selected from the group consisting of human $IgG_1$, $IgG_2$, $IgG_3$, $IgG_4$, $IgA_1$, and $IgA_2$.

In certain embodiments, the instant disclosure provides an antibody that specifically binds to MSLN (e.g., human MSLN), the antibody comprising a heavy chain constant region that is a variant of a wild-type heavy chain constant region, wherein the variant heavy chain constant region binds to an FcγR with lower affinity than the wild-type heavy chain constant region binds to the FcγR.

In certain embodiments, the instant disclosure provides an antibody that specifically binds to MSLN (e.g., human MSLN), the antibody comprising a heavy chain constant region comprising the amino acid sequence of SEQ ID NO: 72, 53, 54, 55, or 56. In certain embodiments, the instant disclosure provides an antibody that specifically binds to MSLN (e.g., human MSLN), the antibody comprising a heavy chain constant region consisting of the amino acid sequence of SEQ ID NO: 72, 53, 54, 55, or 56.

In certain embodiments, one, two, or more mutations (e.g., amino acid substitutions) are introduced into an Fc region (e.g., a CH2 domain (residues 231-340 of human $IgG_1$)) and/or a CH3 domain (residues 341-447 of human $IgG_1$, numbered according to the EU numbering system) and/or a hinge region (residues 216-230, numbered according to the EU numbering system) of an antibody described herein, to alter one or more functional properties of the antibody, such as serum half-life, complement fixation, Fc receptor binding, and/or antigen-dependent cellular cytotoxicity.

In certain embodiments, one, two, or more mutations (e.g., amino acid substitutions) are introduced into the hinge region of an antibody described herein, such that the number of cysteine residues in the hinge region is altered (e.g., increased or decreased) as described in, e.g., U.S. Pat. No. 5,677,425, herein incorporated by reference in its entirety. The number of cysteine residues in the hinge region may be altered to, e.g., facilitate assembly of the light and heavy chains, or to alter (e.g., increase or decrease) the stability of the antibody.

In a specific embodiment, one, two, or more amino acid mutations (e.g., substitutions, insertions, or deletions) are introduced into an IgG constant region, or FcRn-binding fragment thereof (preferably an Fc or hinge-Fc fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745, all of which are herein incorporated by reference in their entireties, for examples of mutations that will alter (e.g., decrease or increase) the half-life of an antibody in vivo. In certain embodiments, one, two or more amino acid mutations (e.g., substitutions, insertions, or deletions) are introduced into an IgG constant region, or FcRn-binding fragment thereof (preferably an Fc or hinge-Fc fragment) to decrease the half-life of the antibody in vivo. In other embodiments, one, two or more amino acid mutations (e.g., substitutions, insertions, or deletions) are introduced into an IgG constant region, or FcRn-binding fragment thereof (preferably an Fc or hinge-Fc fragment) to increase the half-life of the antibody in vivo. In a specific embodiment, the antibodies may have one or more amino acid mutations (e.g., substitutions) in the second constant (CH2) domain (residues 231-340 of human $IgG_1$) and/or the third constant (CH3) domain (residues 341-447 of human $IgG_1$), numbered according to the EU numbering system. In a specific embodiment, the constant region of the $IgG_1$ of antibody described herein comprises a methionine (M) to tyrosine (Y) substitution in position 252, a serine (S) to threonine (T) substitution in position 254, and a threonine (T) to glutamic acid (E) substitution in position 256, numbered according to the EU numbering system. See U.S. Pat. No. 7,658,921, which is herein incorporated by reference in its entirety. This type of mutant IgG, referred to as "YTE mutant" has been shown to display fourfold increased half-life as compared to wild-type versions of the same antibody (see Dall'Acqua W F et al., (2006) J Biol Chem 281: 23514-24, which is herein incorporated by reference in its entirety). In certain embodiments, an antibody comprises an IgG constant region comprising one, two, three or more amino acid substitutions of amino acid residues at positions 251-257, 285-290, 308-314, 385-389, and 428-436, numbered according to the EU numbering system.

In certain embodiments, one, two, or more mutations (e.g., amino acid substitutions) are introduced into an Fc region (e.g., a CH2 domain (residues 231-340 of human $IgG_1$)) and/or a CH3 domain (residues 341-447 of human $IgG_1$, numbered according to the EU numbering system) and/or a hinge region (residues 216-230, numbered according to the EU numbering system) of an antibody described herein, to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, all of which are herein incorporated by reference in their entireties.

In certain embodiments, the antibody comprises a heavy chain constant region that is a variant of a wild-type heavy chain constant region, wherein the variant heavy chain constant region binds to FcγRIIB with higher affinity than the wild-type heavy chain constant region binds to FcγRIIB. In certain embodiments, the variant heavy chain constant region is a variant human heavy chain constant region, e.g., a variant human $IgG_1$, a variant human $IgG_2$, or a variant human IgG$_4$ heavy chain constant region. In certain embodiments, the variant human IgG heavy chain constant region comprises one or more of the following amino acid mutations, according to the EU numbering system: G236D, P238D, S239D, S267E, L328F, and L328E. In certain embodiments, the variant human IgG heavy chain constant region comprises a set of amino acid mutations selected from the group consisting of: S267E and L328F; P238D and L328E; P238D and one or more substitutions selected from the group consisting of E233D, G237D, H268D, P271G, and A330R; P238D, E233D, G237D, H268D, P271G, and A330R; G236D and S267E; S239D and S267E; V262E, S267E, and L328F; and V264E, S267E, and L328F, according to the EU numbering system. In certain embodiments, the FcγRIIB is expressed on a cell selected from the group consisting of macrophages, monocytes, B cells, dendritic cells, endothelial cells, and activated T cells.

In a further embodiment, one, two, or more amino acid substitutions are introduced into an IgG constant region Fc region to alter the effector function(s) of the antibody. For example, one or more amino acids selected from amino acid residues 234, 235, 236, 237, 239, 243, 267, 292, 297, 300, 318, 320, 322, 328, 330, 332, and 396, numbered according to the EU numbering system, can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, each of which is herein incorporated by reference in its entirety. In certain embodiments, the deletion or inactivation (through point mutations or other means) of a constant region domain may reduce Fc receptor binding of the circulating antibody thereby increasing tumor localization. See, e.g., U.S. Pat. Nos. 5,585,097 and 8,591,886, each of which is herein incorporated by reference in its entirety, for a description of mutations that delete or inactivate the constant region and thereby increase tumor localization. In certain embodiments, one or more amino acid substitutions may be introduced into the Fc region of an antibody described herein to remove potential glycosylation sites on the Fc region, which may reduce Fc receptor binding (see, e.g., Shields R L et al., (2001) J Biol Chem 276: 6591-604, which is herein incorporated by reference in its entirety). In various embodiments, one or more of the following mutations in the constant region of an antibody described herein may be made: an N297A substitution; an N297Q substitution; an L234A substitution; an L234F substitution; an L235A substitution; an L235F substitution; an L235V substitution; an L237A substitution; an S239D substitution; an E233P substitution; an L234V substitution; an L235A substitution; a C236 deletion; a P238A substitution; an S239D substitution; an F243L substitution; a D265A substitution; an S267E substitution; an L328F substitution; an R292P substitution; a Y300L substitution; an A327Q substitution; a P329A substitution; an A330L substitution; an I332E substitution; or a P396L substitution, numbered according to the EU numbering system.

In certain embodiments, a mutation selected from the group consisting of D265A, P329A, and a combination thereof, numbered according to the EU numbering system, may be made in the constant region of an antibody described herein. In certain embodiments, a mutation selected from the group consisting of L235A, L237A, and a combination thereof, numbered according to the EU numbering system, may be made in the constant region of an antibody described herein. In certain embodiments, a mutation selected from the group consisting of S267E, L328F, and a combination thereof, numbered according to the EU numbering system, may be made in the constant region of an antibody described herein. In certain embodiments, a mutation selected from the group consisting of S239D, I332E, optionally A330L, and a combination thereof, numbered according to the EU numbering system, may be made in the constant region of an antibody described herein. In certain embodiments, a mutation selected from the group consisting of L235V, F243L, R292P, Y300L, P396L, and a combination thereof, numbered according to the EU numbering system, may be made in the constant region of an antibody described herein. In certain embodiments, a mutation selected from the group consisting of S267E, L328F, and a combination thereof, numbered according to the EU numbering system, may be made in the constant region of an antibody described herein.

In a specific embodiment, an antibody described herein comprises the constant region of an IgG$_1$ with an N297Q or N297A amino acid substitution, numbered according to the EU numbering system. In certain embodiments, an antibody described herein comprises the constant region of an IgG$_1$ with a mutation selected from the group consisting of D265A, P329A, and a combination thereof, numbered according to the EU numbering system. In another embodiment, an antibody described herein comprises the constant region of an IgG$_1$ with a mutation selected from the group consisting of L234A, L235A, and a combination thereof, numbered according to the EU numbering system. In another embodiment, an antibody described herein comprises the constant region of an IgG$_1$ with a mutation selected from the group consisting of L234F, L235F, N297A, and a combination thereof, numbered according to the EU numbering system. In certain embodiments, amino acid residues in the constant region of an antibody described herein in the positions corresponding to positions L234, L235, and D265 in a human IgG$_1$ heavy chain, numbered according to the EU numbering system, are not L, L, and D, respectively. This approach is described in detail in International Publication No. WO 14/108483, which is herein incorporated by reference in its entirety. In certain embodiments, the amino acids corresponding to positions L234, L235, and D265 in a human IgG$_1$ heavy chain are F, E, and A; or A, A, and A, respectively, numbered according to the EU numbering system.

In certain embodiments, one or more amino acids selected from amino acid residues 329, 331, and 322 in the constant region of an antibody described herein, numbered according to the EU numbering system, can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al.), which is herein incorporated by reference in its entirety. In certain embodiments, one or more amino acid residues within amino acid positions 231 to 238 in the N-terminal region of the CH2 domain of an antibody described herein are altered to thereby alter the ability of the antibody to fix complement, numbered according to the EU numbering system. This approach is described further in International Publication No. WO 94/29351, which is herein incorporated by reference in its entirety. In certain embodiments, the Fc region of an antibody described herein is modified to increase the ability of the antibody to mediate antibody dependent cellular cytotoxicity (ADCC) and/or to increase the affinity of the antibody for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU numbering system. This approach is described further in International Publication No. WO 00/42072, which is herein incorporated by reference in its entirety.

In certain embodiments, an antibody described herein comprises a modified constant region of an IgG$_1$, wherein the modification increases the ability of the antibody to mediate antibody dependent cellular cytotoxicity (ADCC). In certain embodiments, 0.1, 1, or 10 μg/mL of the antibody is capable of inducing cell death of at least 20%, 25%, 30%, 35%, 40%, 45%, 50%, 55%, or 60% of MSLN-expressing cells within 1, 2, or 3 hours, as assessed by methods described herein and/or known to a person of skill in the art. In certain embodiments, the modified constant region of an IgG$_1$ comprises S239D and I332E substitutions, numbered according to the EU numbering system. In certain embodiments, the modified constant region of an IgG$_1$ comprises S239D, A330L, and I332E substitutions, numbered according to the EU numbering system. In certain embodiments, the modified constant region of an IgG$_1$ comprises L235V, F243L, R292P, Y300L, and P396L substitutions, numbered according to the EU numbering system. In certain embodiments, the antibody is capable of inducing cell death in effector T cells and Tregs, wherein the percentage of Tregs that undergo cell death is higher than the percentage of effector T cells that undergo cell death by at least 1.2 fold, 1.3 fold, 1.4 fold, 1.5 fold, 1.6 fold, 1.7 fold, 1.8 fold, 1.9 fold, 2 fold, 2.5 fold, 3 fold, 3.5 fold, 4 fold, 4.5 fold, or 5 fold.

In certain embodiments, an antibody described herein comprises the constant region of an IgG$_4$ antibody and the serine at amino acid residue 228 of the heavy chain, numbered according to the EU numbering system, is substituted for proline. In certain embodiments, the instant disclosure provides an antibody that specifically binds to MSLN (e.g., human MSLN), the antibody comprising a heavy chain constant region comprising the amino acid sequence of SEQ ID NO: 16 or 22.

In certain embodiments, any of the constant region mutations or modifications described herein can be introduced into one or both heavy chain constant regions of an antibody described herein having two heavy chain constant regions.

Pharmaceutical Compositions

Provided herein are compositions comprising an anti-MSLN antibody disclosed herein having the desired degree of purity in a physiologically acceptable carrier, excipient, or stabilizer (see, e.g., Remington's Pharmaceutical Sciences (1990) Mack Publishing Co., Easton, PA). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates, including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In a specific embodiment, pharmaceutical compositions comprise an anti-MSLN antibody disclosed herein, and optionally one or more additional prophylactic or therapeutic agents, in a pharmaceutically acceptable carrier. In a specific embodiment, pharmaceutical compositions comprise an anti-MSLN antibody disclosed herein, and optionally one or more additional prophylactic or therapeutic agents, in a pharmaceutically acceptable carrier. In certain embodiments, the antibody is the only active ingredient included in the pharmaceutical composition. Pharmaceutical compositions described herein can be useful in increasing or promoting MSLN (e.g., human MSLN) activity and treating a condition, such as cancer. In certain embodiments, the present disclosure relates to a pharmaceutical composition of the present disclosure comprising an anti-MSLN antibody of the present disclosure for use as a medicament. In another embodiment, the present disclosure relates to a pharmaceutical composition of the present disclosure for use in a method for the treatment of cancer.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering, or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol, and propylene glycol for water miscible vehicles; and sodium hydroxide, hydrochloric acid, citric acid or lactic acid for pH adjustment.

A pharmaceutical composition can be formulated for any route of administration to a subject. Specific examples of routes of administration include intranasal, oral, pulmonary, transdermal, intradermal, and parenteral. Parenteral administration, characterized by either subcutaneous, intramuscular, or intravenous injection, is also contemplated herein. Injectables can be prepared in conventional forms, either as liquid solutions or suspensions, solid forms suitable for solution or suspension in liquid prior to injection, or as emulsions. The injectables, solutions, and emulsions also contain one or more excipients. Suitable excipients are, for example, water, saline, dextrose, glycerol, or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate, and cyclodextrins.

Preparations for parenteral administration of antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol, and mixtures thereof.

Topical mixtures comprising an antibody are prepared as described for the local and systemic administration. The resulting mixture can be a solution, suspension, emulsions, or the like and can be formulated as creams, gels, ointments, emulsions, solutions, elixirs, lotions, suspensions, tinctures, pastes, foams, aerosols, irrigations, sprays, suppositories, bandages, dermal patches, or any other formulations suitable for topical administration.

An anti-MSLN antibody disclosed herein can be formulated as an aerosol for topical application, such as by inhalation (see, e.g., U.S. Pat. Nos. 4,044,126, 4,414,209 and 4,364,923, which describe aerosols for delivery of a steroid useful for treatment of inflammatory diseases, particularly asthma and are herein incorporated by reference in their entireties). These formulations for administration to the respiratory tract can be in the form of an aerosol or solution for a nebulizer, or as a microfine powder for insufflations, alone or in combination with an inert carrier such as lactose. In such a case, the particles of the formulation will, in certain embodiments, have diameters of less than 50 microns, In certain embodiments less than 10 microns.

An anti-MSLN antibody disclosed herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957, all of which are herein incorporated by reference in their entireties.

In certain embodiments, a pharmaceutical composition comprising antibody described herein is a lyophilized powder, which can be reconstituted for administration as solutions, emulsions, and other mixtures. It may also be reconstituted and formulated as solids or gels. The lyophilized powder is prepared by dissolving antibody described herein, or a pharmaceutically acceptable derivative thereof, in a suitable solvent. In certain embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose, or other suitable agent. The solvent may also contain a buffer, such as citrate, sodium or potassium phosphate or other such buffer known to those of skill in the art at, In certain embodiments, about neutral pH. Subsequent sterile filtration of the solution followed by lyophilization under standard conditions known to those of skill in the art provides the desired formulation. In certain embodiments, the resulting solution will be apportioned into vials for lyophilization. Each vial will contain a single dosage or multiple dosages of the compound. The lyophilized powder can be stored under appropriate conditions, such as at about 4° C. to room temperature. Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The anti-MSLN antibodies disclosed herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874, all of which are herein incorporated by reference in their entireties. In a specific embodiment, an antibody described herein is targeted to a tumor.

The compositions to be used for in vivo administration can be sterile. This is readily accomplished by filtration through, e.g., sterile filtration membranes.

Methods of Use and Uses

In another aspect, the instant disclosure provides a method of treating a subject using the anti-MSLN antibodies disclosed herein. Any disease or disorder in a subject that would benefit from decrease of MSLN (e.g., human MSLN) function can be treated using the anti-MSLN antibodies disclosed herein. In certain embodiments, the disease or disorder is resistant to a checkpoint targeting agent (e.g., an antagonist anti-CTLA-4 antibody, an antagonist anti-PD-L1 antibody, an antagonist anti-PD-L2 antibody, or an antagonist anti-PD-1 antibody). In certain embodiments, the disease or disorder is recurrent after treatment with a checkpoint targeting agent (e.g., an antagonist anti-CTLA-4 antibody, an antagonist anti-PD-L1 antibody, an antagonist anti-PD-L2 antibody, or an antagonist anti-PD-1 antibody).

The anti-MSLN antibodies disclosed herein are particularly useful for inhibiting immune system tolerance to tumors, and accordingly can be used as an immunotherapy for subjects with cancer. For example, in certain embodiments, the instant disclosure provides a method of increasing T cell (e.g., $CD8^+$ cytotoxic T cells, $CD4^+$ helper T cells, NKT cells, effector T cells, or memory T cells) activation in response to an antigen in a subject, the method comprising administering to the subject an effective amount of an anti-MSLN antibody or pharmaceutical composition thereof as disclosed herein. In certain embodiments, the instant disclosure provides a method of treating cancer in a subject, the method comprising administering to the subject an effective amount of the antibody or pharmaceutical composition, as disclosed herein.

Cancers that can be treated with the anti-MSLN antibodies or pharmaceutical compositions disclosed herein include, without limitation, a solid tumor, a hematological cancer (e.g., leukemia, lymphoma, myeloma, e.g., multiple myeloma), and a metastatic lesion. In certain embodiments, the cancer is a solid tumor. Examples of solid tumors include malignancies, e.g., sarcomas and carcinomas, e.g., adenocarcinomas of the various organ systems, such as those affecting the lung, breast, ovarian, lymphoid, gastrointestinal (e.g., colon), anal, genitals and genitourinary tract (e.g., renal, urothelial, bladder cells, prostate), pharynx, CNS (e.g., brain, neural or glial cells), head and neck, skin (e.g., melanoma), and pancreas, as well as adenocarcinomas which include malignancies such as colon cancers, rectal cancer, renal-cell carcinoma, liver cancer, lung cancer (e.g., non-small cell lung cancer or small cell lung cancer), cancer of the small intestine and cancer of the esophagus. The cancer may be at an early, intermediate, late stage, or metastatic cancer. In certain embodiments, the cancer is resistant to a checkpoint targeting agent (e.g., an antagonist anti-CTLA-4 antibody, an antagonist anti-PD-L1 antibody, an antagonist anti-PD-L2 antibody, or an antagonist anti-PD-1 antibody). In certain embodiments, the cancer is recurrent after treatment with a checkpoint targeting agent (e.g., an antagonist anti-CTLA-4 antibody, an antagonist anti-PD-L1 antibody, an antagonist anti-PD-L2 antibody, or an antagonist anti-PD-1 antibody).

In certain embodiments, the cancer is chosen from lung cancer (e.g., lung adenocarcinoma or non-small cell lung cancer (NSCLC) (e.g., NSCLC with squamous and/or non-squamous histology, or NSCLC adenocarcinoma)), melanoma (e.g., an advanced melanoma), renal cancer (e.g., a renal cell carcinoma), liver cancer (e.g., hepatocellular carcinoma), myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), an ovarian cancer, a colorectal cancer, a pancreatic cancer, a head and neck cancer (e.g., head and neck squamous cell carcinoma (HNSCC)), anal cancer, gastro-esophageal cancer (e.g., esophageal squamous cell carcinoma), mesothelioma, nasopharyngeal cancer, thyroid cancer, cervical cancer, epithelial cancer, peritoneal cancer, or a lymphoproliferative disease (e.g., a post-transplant lymphoproliferative disease).

In certain embodiments, the cancer is a hematological cancer, for example, a leukemia, a lymphoma, or a myeloma. In certain embodiments, the cancer is a leukemia, for example, acute lymphoblastic leukemia (ALL), acute myelogenous leukemia (AML), acute myeloblastic leukemia (AML), chronic lymphocytic leukemia (CLL), chronic myelogenous leukemia (CML), chronic myeloid leukemia (CML), chronic myelomonocytic leukemia (CMML), chronic lymphocytic leukemia (CLL), or hairy cell leukemia. In certain embodiments, the cancer is a lymphoma, for example, B cell lymphoma, diffuse large B-cell lymphoma (DLBCL), activated B-cell like (ABC) diffuse large B cell lymphoma, germinal center B cell (GCB) diffuse large B cell lymphoma, mantle cell lymphoma, Hodgkin lymphoma, non-Hodgkin lymphoma, relapsed non-Hodgkin lymphoma, refractory non-Hodgkin lymphoma, recurrent follicular non-Hodgkin lymphoma, Burkitt lymphoma, small lymphocytic lymphoma, follicular lymphoma, lymphoplasmacytic lymphoma, or extranodal marginal zone lymphoma. In certain embodiments the cancer is a myeloma, for example, multiple myeloma.

In another embodiment, the cancer is chosen from a carcinoma (e.g., advanced or metastatic carcinoma), melanoma or a lung carcinoma, e.g., a non-small cell lung carcinoma.

In certain embodiments, the cancer is a lung cancer, e.g., a lung adenocarcinoma, non-small cell lung cancer, or small cell lung cancer.

In certain embodiments, the cancer is a melanoma, e.g., an advanced melanoma. In certain embodiments, the cancer is an advanced or unresectable melanoma that does not respond to other therapies. In other embodiments, the cancer is a melanoma with a BRAF mutation (e.g., a BRAF V600 mutation). In yet other embodiments, the anti-MSLN antibodies or pharmaceutical composition disclosed herein is administered after treatment with an anti-CTLA-4 antibody (e.g., ipilimumab) with or without a BRAF inhibitor (e.g., vemurafenib or dabrafenib).

In another embodiment, the cancer is a hepatocarcinoma, e.g., an advanced hepatocarcinoma, with or without a viral infection, e.g., a chronic viral hepatitis.

In another embodiment, the cancer is a prostate cancer, e.g., an advanced prostate cancer.

In yet another embodiment, the cancer is a myeloma, e.g., multiple myeloma.

In yet another embodiment, the cancer is a renal cancer, e.g., a renal cell carcinoma (RCC) (e.g., a metastatic RCC, clear cell renal cell carcinoma (CCRCC) or kidney papillary cell carcinoma).

In yet another embodiment, the cancer is chosen from a lung cancer, a melanoma, a renal cancer, a breast cancer, a colorectal cancer, a leukemia, or a metastatic lesion of the cancer.

In certain embodiments, these methods further comprise administering an additional therapeutic agent to the subject. In certain embodiments, the additional therapeutic agent is a chemotherapeutic, a radiotherapeutic, or a checkpoint targeting agent. In certain embodiments, the chemotherapeutic agent is a hypomethylating agent (e.g., azacitidine). In certain embodiments, the chemotherapeutic agent is a DNA damage-inducing agent (e.g., gemcitabine). In certain embodiments, the checkpoint targeting agent is selected from the group consisting of an antagonist anti-CTLA-4 antibody, an antagonist anti-PD-L1 antibody, an antagonist anti-PD-L2 antibody, an antagonist anti-PD-1 antibody, an antagonist anti-TIM-3 antibody, an antagonist anti-LAG-3 antibody, an antagonist anti-VISTA antibody, an antagonist anti-CD96 antibody, an antagonist anti-CEACAM1 antibody, an agonist anti-CD137 antibody, an agonist anti-GITR antibody, and an agonist anti-OX40 antibody. In certain embodiments, the checkpoint targeting agent is selected from the group consisting of an antagonist anti-CTLA-4 antibody, an antagonist anti-PD-L1 antibody, an antagonist anti-PD-L2 antibody, and an antagonist anti-PD-1 antibody, wherein the MSLN (e.g., human MSLN) antibodies or pharmaceutical compositions disclosed herein synergize with the checkpoint targeting agent.

In certain embodiments, the present disclosure relates to an antibody and/or pharmaceutical composition of the present disclosure for use in a method of the present disclosure, wherein the method further comprises administering an additional therapeutic agent to the subject. In certain embodiments, the present disclosure relates to (a) an antibody and/or pharmaceutical composition of the present disclosure and (b) an additional therapeutic agent for use as a medicament. In certain embodiments, the present disclosure relates to (a) an antibody and/or pharmaceutical composition of the present disclosure and (b) an additional therapeutic agent for use in a method for the treatment of cancer. In a further embodiment, the present disclosure relates to a pharmaceutical composition, kit or kit-of-parts comprising (a) an antibody and/or pharmaceutical composition of the present disclosure and (b) an additional therapeutic agent. In certain embodiments, the additional therapeutic agent is a chemotherapeutic, a radiotherapeutic, or a checkpoint targeting agent.

In certain embodiments, an anti-PD-1 antibody is used in methods disclosed herein. In certain embodiments, the anti-PD-1 antibody is nivolumab, also known as BMS-936558 or MDX1106, developed by Bristol-Myers Squibb. In certain embodiments, the anti-PD-1 antibody is pembrolizumab, also known as lambrolizumab or MK-3475, developed by Merck & Co. In certain embodiments, the anti-PD-1 antibody is pidilizumab, also known as CT-011, developed by CureTech. In certain embodiments, the anti-PD-1 antibody is MEDI0680, also known as AMP-514, developed by Medimmune. In certain embodiments, the anti-PD-1 antibody is PDR001 developed by Novartis Pharmaceuticals. In certain embodiments, the anti-PD-1 antibody is REGN2810 developed by Regeneron Pharmaceuticals. In certain embodiments, the anti-PD-1 antibody is PF-06801591 developed by Pfizer. In certain embodiments, the anti-PD-1 antibody is BGB-A317 developed by BeiGene. In certain embodiments, the anti-PD-1 antibody is TSR-042 developed by AnaptysBio and Tesaro. In certain embodiments, the anti-PD-1 antibody is SHR-1210 developed by Hengrui.

Further non-limiting examples of anti-PD-1 antibodies that may be used in treatment methods disclosed herein are disclosed in the following patents and patent applications, all of which are herein incorporated by reference in their entireties for all purposes: U.S. Pat. Nos. 6,808,710; 7,332,582; 7,488,802; 8,008,449; 8,114,845; 8,168,757; 8,354,509; 8,686,119; 8,735,553; 8,747,847; 8,779,105; 8,927,697; 8,993,731; 9,102,727; 9,205,148; U.S. Publication No. US 2013/0202623 A1; U.S. Publication No. US 2013/0291136 A1; U.S. Publication No. US 2014/0044738 A1; U.S. Publication No. US 2014/0356363 A1; U.S. Publication No. US 2016/0075783 A1; and PCT Publication No. WO 2013/033091 A1; PCT Publication No. WO 2015/036394 A1; PCT Publication No. WO 2014/179664 A2; PCT Publication No. WO 2014/209804 A1; PCT Publication No. WO 2014/206107 A1; PCT Publication No. WO 2015/058573 A1; PCT Publication No. WO 2015/085847 A1; PCT Publication No. WO 2015/200119 A1; PCT Publication No. WO 2016/015685 A1; and PCT Publication No. WO 2016/020856 A1.

In certain embodiments, an anti-PD-L1 antibody is used in methods disclosed herein. In certain embodiments, the anti-PD-L1 antibody is atezolizumab developed by Genentech. In certain embodiments, the anti-PD-L1 antibody is durvalumab developed by AstraZeneca, Celgene, and Medimmune. In certain embodiments, the anti-PD-L1 antibody is avelumab, also known as MSB0010718C, developed by Merck Serono and Pfizer. In certain embodiments, the anti-PD-L1 antibody is MDX-1105 developed by Bristol-Myers Squibb. In certain embodiments, the anti-PD-L1 antibody is AMP-224 developed by Amplimmune and GSK.

Non-limiting examples of anti-PD-L1 antibodies that may be used in treatment methods disclosed herein are disclosed in the following patents and patent applications, all of which are herein incorporated by reference in their entireties for all purposes: U.S. Pat. Nos. 7,943,743; 8,168,179; 8,217,149; 8,552,154; 8,779,108; 8,981,063; 9,175,082; U.S. Publication No. US 2010/0203056 A1; U.S. Publication No. US 2003/0232323 A1; U.S. Publication No. US 2013/0323249 A1; U.S. Publication No. US 2014/0341917 A1; U.S. Publication No. US 2014/0044738 A1; U.S. Publication No. US 2015/0203580 A1; U.S. Publication No. US 2015/0225483 A1; U.S. Publication No. US 2015/0346208 A1; U.S. Publication No. US 2015/0355184 A1; and PCT Publication No. WO 2014/100079 A1; PCT Publication No. WO 2014/022758 A1; PCT Publication No. WO 2014/055897 A2; PCT Publication No. WO 2015/061668 A1; PCT Publication No. WO 2015/109124 A1; PCT Publication No. WO 2015/195163 A1; PCT Publication No. WO 2016/000619 A1; and PCT Publication No. WO 2016/030350 A1.

In certain embodiments, an anti-CTLA-4 antibody is used in methods disclosed herein. In certain embodiments, the anti-CTLA-4 antibody is ipilimumab developed by Bristol-Myers Squibb.

In certain embodiments, an anti-MSLN antibody disclosed herein is administered to a subject in combination with a compound that targets an immunomodulatory enzyme(s) such as IDO (indoleamine-(2,3)-dioxygenase) and/or TDO (tryptophan 2,3-dioxygenase). Therefore, in certain embodiments, the additional therapeutic agent is a compound that targets an immunomodulatory enzyme(s), such as an inhibitor of indoleamine-(2,3)-dioxygenase (IDO). In certain embodiments, such compound is selected from the group consisting of epacadostat (Incyte Corp; see, e.g., WO 2010/005958 which is herein incorporated by reference in its entirety), F001287 (Flexus Biosciences/Bristol-Myers Squibb), indoximod (NewLink Genetics), and NLG919 (NewLink Genetics). In certain embodiments, the compound is epacadostat. In another embodiment, the compound is F001287. In another embodiment, the compound is indoximod. In another embodiment, the compound is NLG919. In a specific embodiment, an anti-MSLN antibody disclosed herein is administered to a subject in combination with an IDO inhibitor for treating cancer. The IDO inhibitor as described herein for use in treating cancer is present in a solid dosage form of a pharmaceutical composition such as a tablet, a pill, or a capsule, wherein the pharmaceutical composition includes an IDO inhibitor and a pharmaceutically acceptable excipient. As such, the antibody as described herein and the IDO inhibitor as described herein can be administered separately, sequentially, or concurrently as separate dosage forms. In certain embodiments, the antibody is administered parenterally, and the IDO inhibitor is administered orally. In certain embodiments, the inhibitor is selected from the group consisting of epacadostat (Incyte Corporation), F001287 (Flexus Biosciences/Bristol-Myers Squibb), indoximod (NewLink Genetics), and NLG919 (NewLink Genetics). Epacadostat has been described in PCT Publication No. WO 2010/005958, which is herein incorporated by reference in its entirety for all purposes. In certain embodiments, the inhibitor is epacadostat. In another embodiment, the inhibitor is F001287. In another embodiment, the inhibitor is indoximod. In another embodiment, the inhibitor is NLG919.

In certain embodiments, an anti-MSLN antibody disclosed herein is administered to a subject in combination with a vaccine. The vaccine can be, e.g., a peptide vaccine, a DNA vaccine, or an RNA vaccine.

In certain embodiments, an anti-MSLN antibody disclosed herein is administered to a subject in combination with an adjuvant. Various adjuvants can be used depending on the treatment context. Non-limiting examples of appropriate adjuvants include, but not limited to, Complete Freund's Adjuvant (CFA), Incomplete Freund's Adjuvant (IFA), montanide ISA (incomplete Seppic adjuvant), the Ribi adjuvant system (RAS), Titer Max, muramyl peptides, Syntex Adjuvant Formulation (SAF), alum (aluminum hydroxide and/or aluminum phosphate), aluminum salt adjuvants, Gerbu® adjuvants, nitrocellulose absorbed antigen, encapsulated or entrapped antigen, 3 De-O-acylated monophosphoryl lipid A (3 D-MPL), immunostimulatory oligonucleotides, toll-like receptor (TLR) ligands, mannan-binding lectin (MBL) ligands, STING agonists, immunostimulating complexes such as saponins, Quil A, QS-21, QS-7, ISCOMATRIX, and others. Other adjuvants include CpG oligonucleotides and double stranded RNA molecules, such as poly(A) and poly(U). Combinations of the above adjuvants may also be used. See, e.g., U.S. Pat. Nos. 6,645,495; 7,029,678; and 7,858,589, all of which are incorporated herein by reference in their entireties. In certain embodiments, the adjuvant used herein is QS-21 STIMULON.

In certain embodiments, an anti-MSLN antibody disclosed herein is administered to a subject in combination with an additional therapeutic agent comprising a TCR. In certain embodiments, the additional therapeutic agent is a soluble TCR. In certain embodiments, the additional therapeutic agent is a cell expressing a TCR. Therefore, in certain embodiments, the present disclosure relates to an antibody and/or pharmaceutical composition of the present disclosure in combination with an additional therapeutic agent comprising a TCR for use as a medicament and/or for use in a method for the treatment of cancer.

In certain embodiments, an anti-MSLN antibody disclosed herein is administered to a subject in combination with a cell expressing a chimeric antigen receptor (CAR). In certain embodiments, the cell is a T cell.

In certain embodiments, an anti-MSLN antibody disclosed herein is administered to a subject in combination with a TCR mimic antibody. In certain embodiments, the TCR mimic antibody is an antibody that specifically binds to a peptide-MHC complex. For non-limiting examples of TCR mimic antibodies, see, e.g., U.S. Pat. No. 9,074,000 and U.S. Publication Nos. US 2009/0304679 A1 and US 2014/0134191 A1, all of which are incorporated herein by reference in their entireties.

In certain embodiments, an anti-MSLN antibody disclosed herein is administered to a subject in combination with a bispecific T-cell engager (BiTE) (e.g., as described in WO2005061547A2, which is incorporated by reference herein in its entirety) and/or a dual-affinity re-targeting antibody (DART) (e.g., as described in WO2012162067A2, which is incorporated by reference herein in its entirety). In certain embodiments, the BiTE and/or DART specifically binds to a tumor-associated antigen (e.g., a polypeptide overexpressed in a tumor, a polypeptide derived from an oncovirus, a polypeptide comprising a post-translational modification specific to a tumor, a polypeptide specifically mutated in a tumor) and a molecule on an effector cell (e.g., CD3 or CD16). In certain embodiments, the tumor-associated antigen is EGFR (e.g., human EGFR), optionally wherein the BiTE and/or DART comprises the VH and VL sequences of cetuximab. In certain embodiments, the tumor-associated antigen is Her2 (e.g., human Her2), optionally wherein the BiTE and/or DART comprises the VH and VL sequences of trastuzumab. In certain embodiments, the tumor-associated antigen is CD20 (e.g., human CD20).

The anti-MSLN antibody and the additional therapeutic agent (e.g., chemotherapeutic, radiotherapeutic, checkpoint targeting agent, IDO inhibitor, vaccine, adjuvant, a soluble TCR, a cell expressing a TCR, a cell expressing a chimeric antigen receptor, and/or a TCR mimic antibody) can be administered separately, sequentially, or concurrently as separate dosage forms. In certain embodiments, an anti-MSLN antibody is administered parenterally, and an IDO inhibitor is administered orally.

An antibody or pharmaceutical composition described herein may be delivered to a subject by a variety of routes. These include, but are not limited to, parenteral, intranasal, intratracheal, oral, intradermal, topical, intramuscular, intraperitoneal, transdermal, intravenous, intratumoral, conjunctival, intra-arterial, and subcutaneous routes. Pulmonary administration can also be employed, e.g., by use of an inhaler or nebulizer, and formulation with an aerosolizing agent for use as a spray. In certain embodiments, the antibody or pharmaceutical composition described herein is delivered subcutaneously or intravenously. In certain embodiments, the antibody or pharmaceutical composition described herein is delivered intra-arterially. In certain embodiments, the antibody or pharmaceutical composition described herein is delivered intratumorally. In certain embodiments, the antibody or pharmaceutical composition described herein is delivered into a tumor draining lymph node.

The amount of an antibody or composition which will be effective in the treatment and/or prevention of a condition will depend on the nature of the disease, and can be determined by standard clinical techniques.

The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight, and health), whether the patient is human or an animal, other medications administered, or whether treatment is prophylactic or therapeutic. Usually, the patient is a human, but non-human mammals, including transgenic mammals, can also be treated. Treatment dosages are optimally titrated to optimize safety and efficacy.

An anti-MSLN antibody described herein can also be used to assay MSLN (e.g., human MSLN) protein levels in a biological sample using classical immunohistological methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}$I, $^{121}$I), carbon (C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label an antibody described herein. Alternatively, a second antibody that recognizes an anti-MSLN antibody described herein can be labeled and used in combination with an anti-MSLN antibody to detect MSLN (e.g., human MSLN) protein levels. Therefore, in certain embodiments, the present disclosure relates to the use of an anti-MSLN antibody of the present disclosure for in vitro detection of MSLN (e.g., human MSLN) protein in a biological sample. In a further embodiment, the present disclosure relates to the use of an anti-MSLN antibody of the disclosure, for assaying and/or detecting MSLN (e.g., human MSLN) protein levels in a biological sample in vitro, optionally wherein the anti-MSLN antibody is conjugated to a radionuclide or detectable label, and/or carries a label described herein, and/or wherein an immunohistological method is used.

Assaying for the expression level of MSLN (e.g., human MSLN) protein is intended to include qualitatively or quantitatively measuring or estimating the level of MSLN (e.g., human MSLN) protein in a first biological sample either directly (e.g., by determining or estimating absolute protein level) or relatively (e.g., by comparing to the disease associated protein level in a second biological sample). MSLN (e.g., human MSLN) polypeptide expression level in the first biological sample can be measured or estimated and compared to a standard MSLN (e.g., human MSLN) protein level, the standard being taken, for example, from a second biological sample obtained from an individual not having the disorder or being determined by averaging levels from a population of individuals not having the disorder. As will be appreciated in the art, once the "standard" MSLN (e.g., human MSLN) polypeptide level is known, it can be used repeatedly as a standard for comparison. Therefore, in a further embodiment, the present disclosure relates to an in vitro method for assaying and/or detecting MSLN protein levels, for example human MSLN protein levels, in a biological sample, comprising qualitatively or quantitatively measuring or estimating the level of MSLN protein, for example of human MSLN protein, in a biological sample, by an immunohistological method.

As used herein, the term "biological sample" refers to any biological sample obtained from a subject, cell line, tissue, or other source of cells potentially expressing MSLN (e.g., human MSLN). Methods for obtaining tissue biopsies and body fluids from animals (e.g., humans or cynomolgus monkeys) are well known in the art. Biological samples include peripheral blood mononuclear cells (PBMCs).

An anti-MSLN antibody described herein can be used for prognostic, diagnostic, monitoring, and screening applications, including in vitro and in vivo applications well known and standard to the skilled artisan and based on the present description. Prognostic, diagnostic, monitoring, and screening assays and kits for in vitro assessment and evaluation of immune system status and/or immune response may be utilized to predict, diagnose, and monitor to evaluate patient samples, including those known to have or suspected of having an immune system-dysfunction or with regard to an anticipated or desired immune system response, antigen response, or vaccine response. The assessment and evaluation of immune system status and/or immune response are also useful in determining the suitability of a patient for a clinical trial of a drug or for the administration of a particular chemotherapeutic agent, a radiotherapeutic agent, or an antibody, including combinations thereof, versus a different agent or antibody. This type of prognostic and diagnostic monitoring and assessment is already in practice utilizing antibodies against the HER2 protein in breast cancer (HercepTest™, Dako) where the assay is also used to evaluate patients for antibody therapy using Herceptin® (trastuzumab). In vivo applications include directed cell therapy and immune system modulation and radio imaging of immune responses. Therefore, in certain embodiments, the present disclosure relates to an anti-MSLN antibody and/or pharmaceutical composition of the present disclosure for use as a diagnostic. In certain embodiments, the present disclosure relates to an anti-MSLN antibody and/or pharmaceutical composition of the present disclosure for use in a method for the prediction, diagnosis and/or monitoring of a subject having or suspected to have an immune system-dysfunction and/or with regard to an anticipated or desired immune system response, antigen response or vaccine response. In another embodiment, the present disclosure relates to the use of an anti-MSLN antibody of the disclosure, for predicting, diagnosing and/or monitoring of a subject having or suspected to have an immune system-dysfunction and/or with regard to an anticipated or desired immune system response, antigen response or vaccine response by assaying and/or detecting human MSLN protein levels in a biological sample of the subject in vitro.

In certain embodiments, an anti-MSLN antibody can be used in immunohistochemistry of biopsy samples. In certain embodiments, the method is an in vitro method. In another embodiment, an anti-MSLN antibody can be used to detect levels of MSLN (e.g., human MSLN), or levels of cells which contain MSLN (e.g., human MSLN) on their membrane surface, the levels of which can then be linked to certain disease symptoms. Anti-MSLN antibodies described herein may carry a detectable or functional label and/or may be conjugated to a radionuclide or detectable label. When fluorescence labels are used, currently available microscopy and fluorescence-activated cell sorter analysis (FACS) or combination of both methods procedures known in the art may be utilized to identify and to quantitate the specific binding members. Anti-MSLN antibodies described herein may carry or may be conjugated to a fluorescence label. Exemplary fluorescence labels include, for example, reactive and conjugated probes, e.g., Aminocoumarin, Fluorescein and Texas red, Alexa Fluor dyes, Cy dyes and DyLight dyes. An anti-MSLN antibody may carry or may be conjugated to a radioactive label or radionuclide, such as the isotopes $^3$H, $^{14}$C, $^{32}$P, $^{35}$S, $^{36}$Cl, $^{51}$Cr, $^{57}$Co, $^{58}$C, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and, $^{186}$Re. When radioactive labels are used, currently available counting procedures known in the art may be utilized to identify and quantitate the specific binding of an anti-MSLN antibody to MSLN (e.g., human MSLN). In the instance where the label is an enzyme, detection may be accomplished by any of the presently utilized colorimetric, spectrophotometric, fluorospectrophotometric, amperometric, or gasometric techniques as known in the art. This can be achieved by contacting a sample or a control sample with an anti-MSLN antibody under conditions that allow for the formation of a complex between the anti-MSLN antibody and MSLN (e.g., human MSLN). Any complexes formed between the anti-MSLN antibody and MSLN (e.g., human MSLN), are detected and compared in the sample and the control. In light of the specific binding of the anti-MSLN antibodies described herein for MSLN (e.g., human MSLN), the anti-MSLN antibodies can be used to specifically detect MSLN (e.g., human MSLN). The anti-MSLN antibodies described herein can also be used to purify MSLN (e.g., human MSLN) via immunoaffinity purification. Also included herein is an assay system which may be prepared in the form of a test kit, kit, or kit-of-parts for the quantitative analysis of the extent of the presence of, for instance, MSLN (e.g., human MSLN)/MSLN (e.g., human MSLN) ligand complexes. The system, test kit, kit, or kit-of-parts may comprise a labeled component, e.g., a labeled antibody, and one or more additional immunochemical reagents.

Polynucleotides, Vectors, and Methods of Producing Antibodies

In another aspect, provided herein are polynucleotides comprising a nucleotide sequence encoding an antibody, or a portion thereof, described herein or a fragment thereof (e.g., a VL and/or VH; and a light chain and/or heavy chain) that specifically binds to an MSLN (e.g., human MSLN) antigen, and vectors, e.g., vectors comprising such polynucleotides for recombinant expression in host cells (e.g., *E. coli* and mammalian cells). Provided herein are polynucleotides comprising nucleotide sequences encoding a heavy and/or light chain of any of the antibodies provided herein, as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecules having less than about 15%, 10%, 5%, 2%, 1%, 0.5%, or 0.1% (in particular less than about 10%) of other material, e.g., cellular material, culture medium, other nucleic acid molecules, chemical precursors, and/or other chemicals. In a specific embodiment, a nucleic acid molecule(s) encoding an antibody described herein is isolated or purified.

In particular aspects, provided herein are polynucleotides comprising nucleotide sequences encoding antibodies, which specifically bind to an MSLN (e.g., human MSLN) polypeptide and comprises an amino acid sequence as described herein, as well as antibodies which compete with such antibodies for binding to an MSLN (e.g., human MSLN) polypeptide (e.g., in a dose-dependent manner), or which binds to the same epitope as that of such antibodies.

In certain aspects, provided herein are polynucleotides comprising a nucleotide sequence encoding the light chain or heavy chain of antibody described herein. The polynucleotides can comprise nucleotide sequences encoding a light chain comprising the VL FRs and CDRs of antibodies described herein (see, e.g., Table 1) or nucleotide sequences encoding a heavy chain comprising the VH FRs and CDRs of antibodies described herein (see, e.g., Table 1). In certain embodiments, a polynucleotide encodes a VH, VL, heavy chain, and/or light chain of a described herein. In another embodiment, a polynucleotide encodes the first VH and the first VL of a described herein. In another embodiment, a polynucleotide encodes the second VH and the second VL of a described herein. In another embodiment, a polynucleotide encodes the first heavy chain and the first light chain of a described herein. In another embodiment, a polynucleotide encodes the second heavy chain and the second light chain of a described herein. In another embodiment, a polynucleotide encodes the VH and/or the VL, or the heavy chain and/or the light chain, of an antibody described herein.

Also provided herein are polynucleotides encoding an anti-MSLN antibody that are optimized, e.g., by codon/RNA optimization, replacement with heterologous signal sequences, and elimination of mRNA instability elements. Methods to generate optimized nucleic acids encoding an anti-MSLN antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly, all of which are herein incorporated by reference in their entireties. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In certain embodiments, it can be desirable to alter one or more codons to encode a conservative mutation, e.g., a similar amino acid with similar chemical structure and properties and/or function as the original amino acid. Such methods can increase expression of an anti-MSLN antibody or fragment thereof by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an anti-MSLN antibody encoded by polynucleotides that have not been optimized.

In certain embodiments, an optimized polynucleotide sequence encoding an anti-MSLN antibody described herein or a fragment thereof (e.g., VL domain and/or VH domain) can hybridize to an antisense (e.g., complementary) polynucleotide of an unoptimized polynucleotide sequence encoding an anti-MSLN antibody described herein or a fragment thereof (e.g., VL domain and/or VH domain). In specific embodiments, an optimized nucleotide sequence encoding an anti-MSLN antibody described herein or a fragment hybridizes under high stringency conditions to antisense polynucleotide of an unoptimized polynucleotide sequence encoding an anti-MSLN antibody described herein or a fragment thereof. In a specific embodiment, an optimized nucleotide sequence encoding an anti-MSLN antibody described herein or a fragment thereof hybridizes under high stringency, intermediate or lower stringency hybridization conditions to an antisense polynucleotide of an unoptimized nucleotide sequence encoding an anti-MSLN antibody described herein or a fragment thereof. Information regarding hybridization conditions has been described, see, e.g., U.S. Patent Application Publication No. US 2005/0048549 (e.g., paragraphs 72-73), which is herein incorporated by reference in its entirety.

The polynucleotides can be obtained, and the nucleotide sequence of the polynucleotides determined, by any method known in the art. Nucleotide sequences encoding antibodies described herein, e.g., antibodies described in Table 1, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17: 242-6, herein incorporated by reference in its entirety), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antigen-binding region of a described here or an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning.

If a clone containing a nucleic acid encoding a particular antigen-binding region or antibody is not available, but the sequence of the antigen-binding region or antibody molecule is known, a nucleic acid encoding the immunoglobulin can be chemically synthesized or obtained from a suitable source (e.g., an antibody cDNA library or a cDNA library generated from, or nucleic acid, preferably poly A+ RNA, isolated from, any tissue or cells expressing the antibody, such as hybridoma cells selected to express an antibody described herein) by PCR amplification using synthetic primers hybridizable to the 3' and 5' ends of the sequence, or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding anti-MSLN (e.g., human MSLN) antibodies described herein can be readily isolated and sequenced using conventional procedures (e.g., by using oligonucleotide probes that are capable of binding specifically to genes encoding the heavy and light chains of the anti-MSLN (e.g., human MSLN) antibodies). Hybridoma cells can serve as a source of such DNA. Once isolated, the DNA can be placed into expression vectors, which are then transfected into host cells such as E. coli cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of anti-MSLN antibodies in the recombinant host cells.

To generate whole antibodies or antigen-binding regions, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 1 or human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable region, constant regions, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant regions in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH domain and/or VL domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3, which is herein incorporated by reference in its entirety.

In certain aspects, provided herein are cells (e.g., host cells) expressing (e.g., recombinantly) antibodies described herein which specifically bind to MSLN (e.g., human MSLN), and related polynucleotides and expression vectors. Provided herein are vectors (e.g., expression vectors) comprising polynucleotides comprising nucleotide sequences encoding anti-MSLN antibodies or a fragment for recombinant expression in host cells, preferably in mammalian cells (e.g., CHO cells). Also provided herein are host cells comprising such vectors for recombinantly expressing anti-MSLN antibodies described herein (e.g., human or humanized antibody). In a particular aspect, provided herein are methods for producing an antibody described herein, comprising expressing the antibody from a host cell.

Recombinant expression of an antibody described herein (e.g., a full-length antigen-binding region or antibody or heavy and/or light chain of an antibody described herein) that specifically binds to MSLN (e.g., human MSLN) generally involves construction of an expression vector containing a polynucleotide that encodes the antibody. Once a polynucleotide encoding an antibody molecule, heavy and/or light chain of an antibody, or a fragment thereof (e.g., heavy and/or light chain variable regions) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing an antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding containing an antibody molecule described herein, a heavy or light chain of an antibody, a heavy or light chain variable region of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122, 464, which are herein incorporated by reference in their entireties) and variable regions of the antibody can be cloned into such a vector for expression of the entire heavy, the entire light chain, or both the entire heavy and light chains.

In certain embodiments, a vector comprises a polynucleotide encoding a VH, VL, heavy chain, and/or light chain of an antibody described herein. In another embodiment, a vector comprises a polynucleotide encoding the VH and the VL of an antibody described herein. In another embodiment, a vector comprises a polynucleotide encoding the heavy chain and the light chain of an antibody described herein.

An expression vector can be transferred to a cell (e.g., host cell) by conventional techniques and the resulting cells can then be cultured by conventional techniques to produce containing an antibody described herein or a fragment thereof. Thus, provided herein are host cells containing a polynucleotide encoding containing an antibody described herein or fragments thereof, or a heavy or light chain thereof, or fragment thereof, or a single-chain antibody described herein, operably linked to a promoter for expression of such sequences in the host cell.

In certain embodiments, a host cell comprises a polynucleotide encoding the VH and VL of an antibody described herein. In another embodiment, a host cell comprises a vector comprising a polynucleotide encoding the VH and VL of an antibody described herein. In another embodiment, a host cell comprises a first polynucleotide encoding the VH of an antibody described herein, and a second polynucleotide encoding the VL of an antibody described herein. In another embodiment, a host cell comprises a first vector comprising a first polynucleotide encoding the VH of an antibody described herein, and a second vector comprising a second polynucleotide encoding the VL of an antibody described herein.

In specific embodiments, a heavy chain/heavy chain variable region expressed by a first cell is associated with a light chain/light chain variable region of a second cell to form an anti-MSLN (e.g., human MSLN) antibody described herein. In certain embodiments, provided herein is a population of host cells comprising such first host cell and such second host cell.

In certain embodiments, provided herein is a population of vectors comprising a first vector comprising a polynucleotide encoding a light chain/light chain variable region of an anti-MSLN (e.g., human MSLN) antibody described herein, and a second vector comprising a polynucleotide encoding a heavy chain/heavy chain variable region of an anti-MSLN (e.g., human MSLN) antibody described herein.

A variety of host-expression vector systems can be utilized to express antibody molecules described herein (see, e.g., U.S. Pat. No. 5,807,715, which is herein incorporated by reference in its entirety). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with, e.g., recombinant bacteriophage DNA, plasmid DNA or cosmid DNA expression vectors containing antibody coding sequences; yeast (e.g., *Saccharomyces* and *Pichia*) transformed with, e.g., recombinant yeast expression vectors containing antibody coding sequences; insect cell systems infected with, e.g., recombinant virus expression vectors (e.g., baculovirus) containing antibody coding sequences; plant cell systems (e.g., green algae such as *Chlamydomonas reinhardtii*) infected with, e.g., recombinant virus expression vectors (e.g., cauliflower mosaic virus, CaMV; tobacco mosaic virus, TMV) or transformed with, e.g., recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7030, HsS78Bst, HeLa, and NIH 3T3, HEK-293T, HepG2, SP210, R1.1, B-W, L-M, BSC1, BSC40, YB/20 and BMT10 cells) harboring, e.g., recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein are Chinese hamster ovary (CHO) cells, for example CHO cells from the CHO GS System™ (Lonza). In certain embodiments, the heavy chain and/or light chain of an antibody produced by a CHO cell may have an N-terminal glutamine or glutamate residue replaced by pyroglutamate. In certain embodiments, cells for expressing antibodies described herein are human cells, e.g., human cell lines. In a specific embodiment, a mammalian expression vector is pOptiVEC™ or pcDNA3.3. In certain embodiments, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as CHO cells, in conjunction with a vector such as the major intermediate early gene promoter element from human cytomegalovirus, are an effective expression system for antibodies (Foecking M K & Hofstetter H (1986) Gene 45: 101-5; and Cockett M I et al., (1990) Biotechnology 8(7): 662-7, each of which is herein incorporated by reference in its entirety). In certain embodiments, antibodies described herein are produced by CHO cells or NS0 cells. In a specific embodiment, the expression of nucleotide sequences encoding antibodies described herein which specifically bind to MSLN (e.g., human MSLN) is regulated by a constitutive promoter, inducible promoter, or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2: 1791-1794), in which the coding sequence can be ligated individually into the vector in frame with the lac Z coding region so that a fusion protein is produced; pIN vectors (Inouye S & Inouye M (1985) Nuc Acids Res 13: 3101-3109; Van Heeke G & Schuster S M (1989) J Biol Chem 24: 5503-5509); and the like, all of which are herein incorporated by reference in their entireties. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spo-*

*doptera frugiperda* cells. The coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the molecule in infected hosts (e.g., see Logan J & Shenk T (1984) PNAS 81(12): 3655-9, which is herein incorporated by reference in its entirety). Specific initiation signals can also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol. 153: 516-544, which is herein incorporated by reference in its entirety).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7030, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, anti-MSLN (e.g., human MSLN) antibodies described herein are produced in mammalian cells, such as CHO cells.

In a specific embodiment, the antibodies described herein have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of α1,6-fucosyltransferase can be used to produce antibodies with reduced fucose content. The Potelligent® system (Lonza) is an example of such a system that can be used to produce antibodies with reduced fucose content.

For long-term, high-yield production of recombinant proteins, stable expression cells can be generated. For example, cell lines which stably express an anti-MSLN (e.g., human MSLN) antibody described herein can be engineered. In specific embodiments, a cell provided herein stably expresses a light chain/light chain variable region and a heavy chain/heavy chain variable region which associate to form an antigen-binding region or an antibody described herein.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-MSLN (e.g., human MSLN) described herein or a fragment thereof. Such engineered cell lines can be particularly useful in screening and evaluation of compositions that interact directly or indirectly with the antibody molecule.

A number of selection systems can be used, including but not limited to the herpes simplex virus thymidine kinase (Wigler M et al., (1977) Cell 11(1): 223-32), hypoxanthine-guanine phosphoribosyltransferase (Szybalska E H & Szybalski W (1962) PNAS 48(12): 2026-2034) and adenine phosphoribosyltransferase (Lowy I et al., (1980) Cell 22(3): 817-23) genes in tk-, hgprt- or aprt-cells, respectively, all of which are herein incorporated by reference in their entireties. Also, antimetabolite resistance can be used as the basis of selection for the following genes: dhfr, which confers resistance to methotrexate (Wigler M et al., (1980) PNAS 77(6): 3567-70; O'Hare K et al., (1981) PNAS 78: 1527-31); gpt, which confers resistance to mycophenolic acid (Mulligan R C & Berg P (1981) PNAS 78(4): 2072-6); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 926-932; and Morgan R A & Anderson W F (1993) Ann Rev Biochem 62: 191-217; Nabel G J & Felgner P L (1993) Trends Biotechnol 11(5): 211-5); and hygro, which confers resistance to hygromycin (Santerre R F et al., (1984) Gene 30(1-3): 147-56), all of which are herein incorporated by reference in their entireties. Methods commonly known in the art of recombinant DNA technology can be routinely applied to select the desired recombinant clone and such methods are described, for example, in Ausubel F M et al., (eds.), Current Protocols in Molecular Biology, John Wiley & Sons, N Y (1993); Kriegler M, Gene Transfer and Expression, A Laboratory Manual, Stockton Press, N Y (1990); and in Chapters 12 and 13, Dracopoli N C et al., (eds.), Current Protocols in Human Genetics, John Wiley & Sons, N Y (1994); Colbere-Garapin F et al., (1981) J Mol Biol 150: 1-14, all of which are herein incorporated by reference in their entireties.

The expression levels of an antibody molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987), which is herein incorporated by reference in its entirety). When a marker in the vector system is amplifiable, increase in the level of inhibitor present in culture of host cell will increase the number of copies of the marker gene. Since the amplified region is associated with the gene of interest, production of the protein will also increase (Crouse G F et al., (1983) Mol Cell Biol 3: 257-66, which is herein incorporated by reference in its entirety).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: about 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot N J (1986) Nature 322: 562-565; and Kohler G (1980) PNAS 77: 2197-2199, each of which is herein incorporated by reference in its entirety). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more genes/nucleotide sequences, or in the range of 2-5, 5-10, or 10-20 genes/nucleotide sequences. For example, a bicistronic nucleic acid construct can comprise, in the following order, a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody described herein is isolated or purified. In certain embodiments, an isolated antibody is one that is substantially free of other antibodies with different antigenic specificities than the isolated antibody. For example, in certain embodiments, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

Anti-MSLN (e.g., human MSLN) antibodies or fragments thereof can be produced by any method known in the art for the synthesis of proteins or antibodies, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, NY; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press, all of which are herein incorporated by reference in their entireties.

In a specific embodiment, an antibody described herein is prepared, expressed, created, or isolated by any means that involves creation, e.g., via synthesis, genetic engineering of DNA sequences. In certain embodiments, such an antibody comprises sequences (e.g., DNA sequences or amino acid sequences) that do not naturally exist within the antibody germline repertoire of an animal or mammal (e.g., human) in vivo.

In one aspect, provided herein is a method of making an anti-MSLN (e.g., human MSLN) antibody comprising culturing a cell or host cell described herein. In certain embodiments, the method is performed in vitro. In a certain aspect, provided herein is a method of making an anti-MSLN (e.g., human MSLN) antibody comprising expressing (e.g., recombinantly expressing) the antibody using a cell or host cell described herein (e.g., a cell or a host cell comprising polynucleotides encoding an antibody described herein). In certain embodiments, the cell is an isolated cell. In certain embodiments, the exogenous polynucleotides have been introduced into the cell. In certain embodiments, the method further comprises the step of purifying the antibody obtained from the cell or host cell.

In certain embodiments, an antibody is produced by expressing in a cell a polynucleotide encoding the VH and VL of an antibody described herein under suitable conditions so that the polynucleotides are expressed and the antibody is produced. In another embodiment, an antibody is produced by expressing in a cell a polynucleotide encoding the heavy chain and light chain of an antibody described herein under suitable conditions so that the polynucleotides are expressed and the antibody is produced. In certain embodiments, an antibody is produced by expressing in a cell a first polynucleotide encoding the VH of an antibody described herein, and a second polynucleotide encoding the VL of an antibody described herein, under suitable conditions so that the polynucleotides are expressed and the antibody is produced. In certain embodiments, an antibody is produced by expressing in a cell a first polynucleotide encoding the heavy chain of an antibody described herein, and a second polynucleotide encoding the light chain of an antibody described herein, under suitable conditions so that the polynucleotides are expressed and the antibody is produced.

Methods for producing polyclonal antibodies are known in the art (see, for example, Chapter 11 in: Short Protocols in Molecular Biology, (2002) 5th Ed., Ausubel F M et al., eds., John Wiley and Sons, New York, which is herein incorporated by reference in its entirety).

Monoclonal antibodies can be prepared using a wide variety of techniques known in the art, including the use of hybridoma, recombinant, and phage display technologies, or a combination thereof. For example, monoclonal antibodies can be produced using hybridoma techniques, including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981), each of which is herein incorporated by reference in its entirety. The term "monoclonal antibody" as used herein is not limited to antibodies produced through hybridoma technology. For example, monoclonal antibodies can be produced recombinantly from host cells exogenously expressing an antibody described herein or a fragment thereof, for example, light chain and/or heavy chain of such antibody.

In specific embodiments, a "monoclonal antibody," as used herein, is an antibody produced by a single cell (e.g., hybridoma or host cell producing a recombinant antibody), wherein the antibody specifically binds to MSLN (e.g., human MSLN) as determined, e.g., by ELISA or other antigen-binding or competitive binding assay known in the art or in the examples provided herein. In certain embodiments, a monoclonal antibody can be a chimeric antibody or a humanized antibody. In certain embodiments, a monoclonal antibody is a monovalent antibody or multivalent (e.g., bivalent) antibody. In certain embodiments, a monoclonal antibody is a monospecific or multispecific antibody (e.g., bispecific antibody). Monoclonal antibodies described herein can, for example, be made by the hybridoma method as described in Kohler G & Milstein C (1975) Nature 256: 495, which is herein incorporated by reference in its entirety, or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

As used herein, an antibody binds to an antigen multivalently (e.g., bivalently) when the antibody comprises at least two (e.g., two or more) monovalent binding regions, each monovalent binding region capable of binding to an epitope on the antigen. Each monovalent binding region can bind to the same or different epitopes on the antigen.

Methods for producing and screening for specific antibodies using hybridoma technology are routine and well known in the art. For example, in the hybridoma method, a mouse or other appropriate host animal, such as a sheep, goat, rabbit, rat, hamster, or macaque monkey, is immunized to elicit lymphocytes that produce or are capable of producing antibodies that will specifically bind to the protein (e.g., MSLN (e.g., human MSLN)) used for immunization. Alternatively, lymphocytes may be immunized in vitro. Lymphocytes then are fused with myeloma cells using a suitable fusing agent, such as polyethylene glycol, to form a hybridoma cell (Goding J W (Ed), Monoclonal Antibodies: Principles and Practice, pp. 59-103 (Academic Press, 1986), herein incorporated by reference in its entirety). Additionally, a RIMMS (repetitive immunization multiple sites) technique can be used to immunize an animal (Kilpatrick K E et al., (1997) Hybridoma 16:381-9, herein incorporated by reference in its entirety).

In certain embodiments, mice (or other animals, such as rats, monkeys, donkeys, pigs, sheep, hamster, or dogs) can be immunized with an antigen (e.g., MSLN (e.g., human MSLN)) and once an immune response is detected, e.g., antibodies specific for the antigen are detected in the mouse serum, the mouse spleen is harvested and splenocytes isolated. The splenocytes are then fused by well-known techniques to any suitable myeloma cells, for example, cells from cell line SP20 available from the American Type Culture Collection (ATCC®) (Manassas, VA), to form hybridomas. Hybridomas are selected and cloned by limited dilution. In certain embodiments, lymph nodes of the immunized mice are harvested and fused with NS0 myeloma cells.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as the NS0 cell line or those derived from MOPC-21 and MPC-11 mouse tumors available from the Salk Institute Cell Distribution Center, San Diego, CA, USA, and SP-2 or X63-Ag8.653 cells available from the American Type Culture Collection, Rockville, MD, USA. Human myeloma and mouse-human heteromyeloma cell lines also have been described for the production of human monoclonal antibodies (Kozbor D (1984) J Immunol 133: 3001-5; Brodeur et al., Monoclonal Antibody Production Techniques and Applications, pp. 51-63 (Marcel Dekker, Inc., New York, 1987), each of which is herein incorporated by reference in its entirety).

Culture medium in which hybridoma cells are growing is assayed for production of monoclonal antibodies directed against MSLN (e.g., human MSLN). The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding J W (Ed), Monoclonal Antibodies: Principles and Practice, supra). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein include, e.g., antibody fragments which recognize MSLN (e.g., human MSLN), and can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of an antibody molecule and contains the complete light chain paired with the VH and CH1 domains of the heavy chain. A F(ab')$_2$ fragment contains the two antigen-binding arms of an antibody molecule linked by disulfide bonds in the hinge region.

Further, the antibodies described herein can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in *E. coli*, and the *E. coli* is infected with helper phage. Phage used in these methods are typically filamentous phage, including fd and M13, and the VH and VL domains are usually recombinantly fused to either the phage gene III or gene VIII. Phage expressing an antigen-binding region that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/11236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108, all of which are herein incorporated by reference in their entireties.

As described in the above references, after phage selection, the antibody coding regions from the phage can be isolated and used to generate whole antibodies, including human antibodies, or any other desired antigen-binding fragment, and expressed in any desired host, including mammalian cells, insect cells, plant cells, yeast, and bacteria, e.g., as described below. Techniques to recombinantly produce antibody fragments such as Fab, Fab' and F(ab')$_2$ fragments can also be employed using methods known in the art such as those disclosed in PCT publication No. WO 92/22324; Mullinax R L et al., (1992) BioTechniques 12(6): 864-9; Sawai H et al., (1995) Am J Reprod Immunol 34: 26-34; and Better M et al., (1988) Science 240: 1041-1043, all of which are herein incorporated by reference in their entireties.

In certain embodiments, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229: 1202-7; Oi V T & Morrison S L (1986) BioTechniques 4: 214-221; Gillies S D et al., (1989) J Immunol Methods 125: 191-202; and U.S. Pat. Nos. 5,807,715, 4,816,567, 4,816,397, and 6,331,415, all of which are herein incorporated by reference in their entireties.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In certain embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA, and IgE, and any isotype, including $IgG_1$, $IgG_2$, $IgG_3$, and $IgG_4$. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) J Immunol 169: 1119-25; Caldas C et al., (2000) Protein Eng. 13(5): 353-60; Morea V et al., (2000) Methods 20(3): 267-79; Baca M et al., (1997) J Biol Chem 272(16): 10678-84; Roguska M A et al., (1996) Protein Eng 9(10): 895 904; Couto J R et al., (1995) Cancer Res. 55 (23 Supp): 5973s-5977s; Couto J R et al., (1995) Cancer Res 55(8): 1717-22;

Sandhu J S (1994) Gene 150(2): 409-10; and Pedersen J T et al., (1994) J Mol Biol 235(3): 959-73, all of which are herein incorporated by reference in their entireties. See also, U.S. Application Publication No. US 2005/0042664 A1 (Feb. 24, 2005), which is herein incorporated by reference in its entirety.

Methods for making multispecific antibodies (e.g., bispecific antibodies) have been described, see, for example, U.S. Pat. Nos. 7,951,917; 7,183,076; 8,227,577; 5,837,242; 5,989,830; 5,869,620; 6,132,992; and 8,586,713, all of which are herein incorporated by reference in their entireties.

Bispecific, bivalent antibodies, and methods of making them, are described, for instance in U.S. Pat. Nos. 5,731,168, 5,807,706, 5,821,333, and U.S. Appl. Publ. Nos. 2003/020734 and 2002/0155537; each of which is herein incorporated by reference in its entirety. Bispecific tetravalent antibodies, and methods of making them are described, for instance, in Int. Appl. Publ. Nos. WO 02/096948 and WO 00/44788, the disclosures of both of which are herein incorporated by reference in its entirety. See generally, Int. Appl. Publ. Nos. WO 93/17715, WO 92/08802, WO 91/00360, and WO 92/05793; Tutt et al., J. Immunol. 147:60-69 (1991); U.S. Pat. Nos. 4,474,893; 4,714,681; 4,925,648; 5,573,920; and 5,601,819; and Kostelny et al., J. Immunol. 148:1547-1553 (1992); each of which is herein incorporated by reference in its entirety.

A bispecific antibody as described herein can be generated according to the DuoBody® technology platform (Genmab A/S) as described, e.g., in International Publication Nos. WO 2011/131746, WO 2011/147986, WO 2008/119353, and WO 2013/060867, and in Labrijn A F et al., (2013) PNAS 110(13): 5145-5150. The DuoBody® technology can be used to combine one half of a first monospecific antibody, or first antigen-binding region, containing two heavy and two light chains with one half of a second monospecific antibody, or second antigen-binding region, containing two heavy and two light chains. The resultant heterodimer contains one heavy chain and one light chain from the first antibody, or first antigen-binding region, paired with one heavy chain and one light chain from the second antibody, or second antigen-binding region. When both of the monospecific antibodies, or antigen-binding regions, recognize different epitopes on different antigens, the resultant heterodimer is a bispecific antibody.

The DuoBody® technology requires that each of the monospecific antibodies, or antigen-binding regions includes a heavy chain constant region with a single point mutation in the CH3 domain. The point mutations allow for a stronger interaction between the CH3 domains in the resultant bispecific antibody than between the CH3 domains in either of the monospecific antibodies, or antigen-binding regions. The single point mutation in each monospecific antibody, or antigen-binding region, is at residue 366, 368, 370, 399, 405, 407, or 409, numbered according to the EU numbering system, in the CH3 domain of the heavy chain constant region, as described, e.g., in International Publication No. WO 2011/131746. Moreover, the single point mutation is located at a different residue in one monospecific antibody, or antigen-binding region, as compared to the other monospecific antibody, or antigen-binding region. For example, one monospecific antibody, or antigen-binding region, can comprise the mutation F405L (i.e., a mutation from phenylalanine to leucine at residue 405), while the other monospecific antibody, or antigen-binding region, can comprise the mutation K409R (i.e., a mutation from lysine to arginine at residue 409), numbered according to the EU numbering system. The heavy chain constant regions of the monospecific antibodies, or antigen-binding regions, can be an $IgG_1$, $IgG_2$, $IgG_3$, or $IgG_4$ isotype (e.g., a human $IgG_1$ isotype), and a bispecific antibody produced by the DuoBody® technology can retain Fc-mediated effector functions.

Another method for generating bispecific antibodies has been termed the "knobs-into-holes" strategy (see, e.g., Intl. Publ. WO2006/028936). The mispairing of Ig heavy chains is reduced in this technology by mutating selected amino acids forming the interface of the CH3 domains in IgG. At positions within the CH3 domain at which the two heavy chains interact directly, an amino acid with a small side chain (hole) is introduced into the sequence of one heavy chain and an amino acid with a large side chain (knob) into the counterpart interacting residue location on the other heavy chain. In some embodiments, compositions of the disclosure have immunoglobulin chains in which the CH3 domains have been modified by mutating selected amino acids that interact at the interface between two polypeptides so as to preferentially form a bispecific antibody. The bispecific antibodies can be composed of immunoglobulin chains of the same subclass (e.g., $IgG_1$ or $IgG_3$) or different subclasses (e.g., $IgG_1$ and $IgG_3$, or $IgG_3$ and $IgG_4$).

Bispecific antibodies can, in some instances contain, $IgG_4$ and $IgG_1$, $IgG_4$ and $IgG_2$, $IgG_4$ and $IgG_3$, or $IgG_1$ and $IgG_3$ chain heterodimers. Such heterodimeric heavy chain antibodies can routinely be engineered by, for example, modifying selected amino acids forming the interface of the CH3 domains in human $IgG_4$ and the $IgG_1$ or $IgG_3$, so as to favor heterodimeric heavy chain formation.

In certain embodiments, an antibody described herein, which binds to the same epitope of MSLN (e.g., human MSLN) as an anti-MSLN (e.g., human MSLN) antibody described herein, is a human antibody. In certain embodiments, an antibody described herein, which competitively blocks (e.g., in a dose-dependent manner) any one of the antibodies described herein, from binding to MSLN (e.g., human MSLN), is a human antibody. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., MSLN (e.g., human MSLN)). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM, and IgE antibodies. For an overview of this technology for producing human antibodies, see Lonberg N & Huszar D (1995) Int Rev Immunol 13:65-93, herein incorporated by reference in its entirety. For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, all of which are herein incorporated by reference in their entireties. Examples of mice capable of producing human antibodies include the Xeno-Mouse™ (Abgenix, Inc.; U.S. Pat. Nos. 6,075,181 and 6,150,184), the HuAb-Mouse™ (Medarex, Inc./Gen Pharm; U.S. Pat. Nos. 5,545,806 and 5,569,825), the Trans Chromo Mouse™ (Kirin) and the KM Mouse™ (Medarex/Kirin), all of which are herein incorporated by reference in their entireties.

Human antibodies that specifically bind to MSLN (e.g., human MSLN) can be made by a variety of methods known in the art, including the phage display methods described above using antibody libraries derived from human immunoglobulin sequences. See also, U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741, all of which are herein incorporated by reference in their entireties.

In certain embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that specifically bind to a target antigen (e.g., MSLN (e.g., human MSLN)). Such methods are known and are described in the art, see, e.g., Shinmoto H et al., (2004) Cytotechnology 46: 19-23; Naganawa Y et al., (2005) Human Antibodies 14: 27-31, each of which is herein incorporated by reference in its entirety.

Kits

Also provided are kits comprising one or more antibodies described herein, or pharmaceutical compositions or conjugates thereof. In a specific embodiment, provided herein is a pharmaceutical pack or kit comprising one or more containers filled with one or more of the ingredients of the pharmaceutical compositions described herein, such as one or more antibodies provided herein. In certain embodiments, the kits contain a pharmaceutical composition described herein and any prophylactic or therapeutic agent, such as those described herein. In certain embodiments, the kits may contain a T cell mitogen, such as, e.g., phytohaemagglutinin (PHA) and/or phorbol myristate acetate (PMA), or a TCR complex stimulating antibody, such as an anti-CD3 antibody and anti-CD28 antibody. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided, are kits that can be used in the above methods. In certain embodiments, a kit comprises an antibody described herein, preferably purified antibody, in one or more containers. In a specific embodiment, kits described herein contain a substantially isolated MSLN (e.g., human MSLN) antigen as a control. In another specific embodiment, the kits described herein further comprise a control antibody which does not react with MSLN (e.g., human MSLN) antigen. In another specific embodiment, kits described herein contain one or more elements for detecting the binding of an antibody to an MSLN (e.g., human MSLN) antigen (e.g., the antibody can be conjugated to a detectable substrate such as a fluorescent compound, an enzymatic substrate, a radioactive compound, or a luminescent compound, or a second antibody which recognizes the first antibody can be conjugated to a detectable substrate). In specific embodiments, a kit provided herein can include a recombinantly produced or chemically synthesized MSLN (e.g., human MSLN) antigen. The MSLN (e.g., human MSLN) antigen provided in the kit can also be attached to a solid support. In a more specific embodiment, the detecting means of the above-described kit includes a solid support to which an MSLN (e.g., human MSLN) antigen is attached. Such a kit can also include a non-attached reporter-labeled anti-human antibody or anti-mouse/rat antibody. In this embodiment, binding of the antibody to the MSLN (e.g., human MSLN) antigen can be detected by binding of the said reporter-labeled antibody. In certain embodiments, the present disclosure relates to the use of a kit of the present disclosure for in vitro assaying and/or detecting MSLN (e.g., human MSLN) antigen in a biological sample.

EXAMPLES

The following examples are offered by way of illustration and not by way of limitation.

Example 1: Binding Kinetics and Optimization of Anti-MSLN 1A12 Antibody Variants Variants of the anti-MSLN 1A12 antibody (see Table 1 above) were made to improve properties and optimize the molecule. Variants of the parental 1A12 variable domains were formatted into aglycosylated (N297A), human kappa IgG1 constructs and expressed in 293 Freestyle cells using lentiviral transduction. Culture supernatants were harvested and purified using protein A affinity chromatography and further purified by size exclusion chromatography using an Agilent high pressure liquid chromatography system (HPLC-SEC). Surface plasmon resonance was used to collect kinetic binding data on a Carterra LSA system. Purified 1A12 antibody variants were captured onto a LSA biosensor chip (HC30M) with immobilized anti-human IgG, and purified MSLN ectodomain was used as an analyte.

Figure 2:
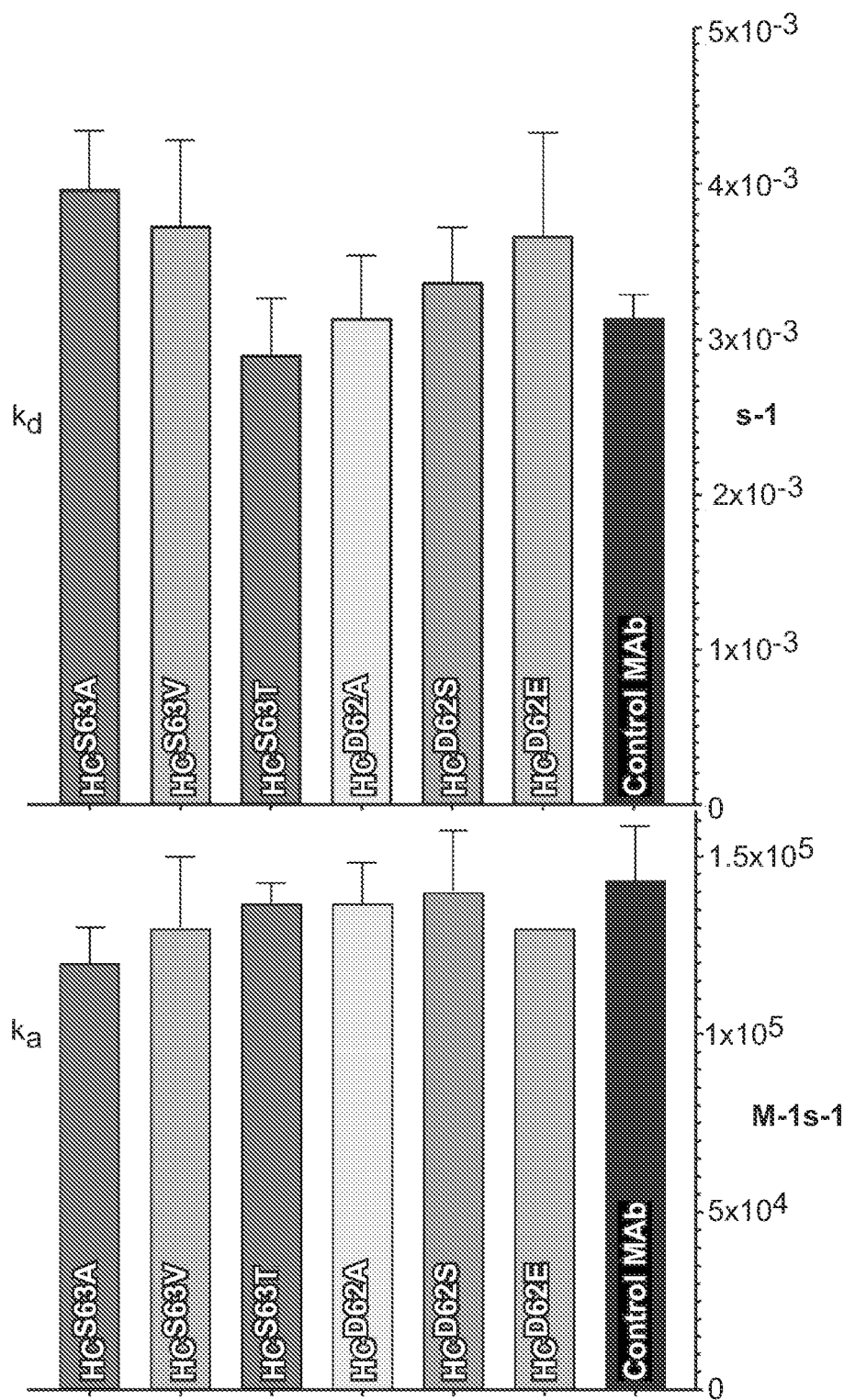
FIG. 2 is a graph showing $K_a$ and $K_d$ (left and right, respectively) for heavy chain variants of the anti-MSLN 1A12 antibody. Control MAb represents the anti-MSLN 1A12 antibody alone.

In order to repair a predicted deamidation site, the "NS" motif of the 1A12 CDRL3 (SEQ ID NO: 8) were mutated. However, certain mutations had deleterious effects on antibody off rate and antibody expression. Mutations of position 92 (N) in the light chain (SEQ ID NO: 10) to either alanine or serine affected antibody binding, resulting in a slower off-rate (FIG. 1A). N92S and S93A mutations also affected antibody expression (FIG. 1). Mutating the "DS" motif in the heavy chain CDRH2 (SEQ ID NO: 4) to repair a predicted isomerization site did not affect antibody binding kinetics. Conservative substitutions at positions 62 (N) and 63 (N+1) in the heavy chain (SEQ ID NO: X) were well tolerated (FIG. 2).

Figure 3:
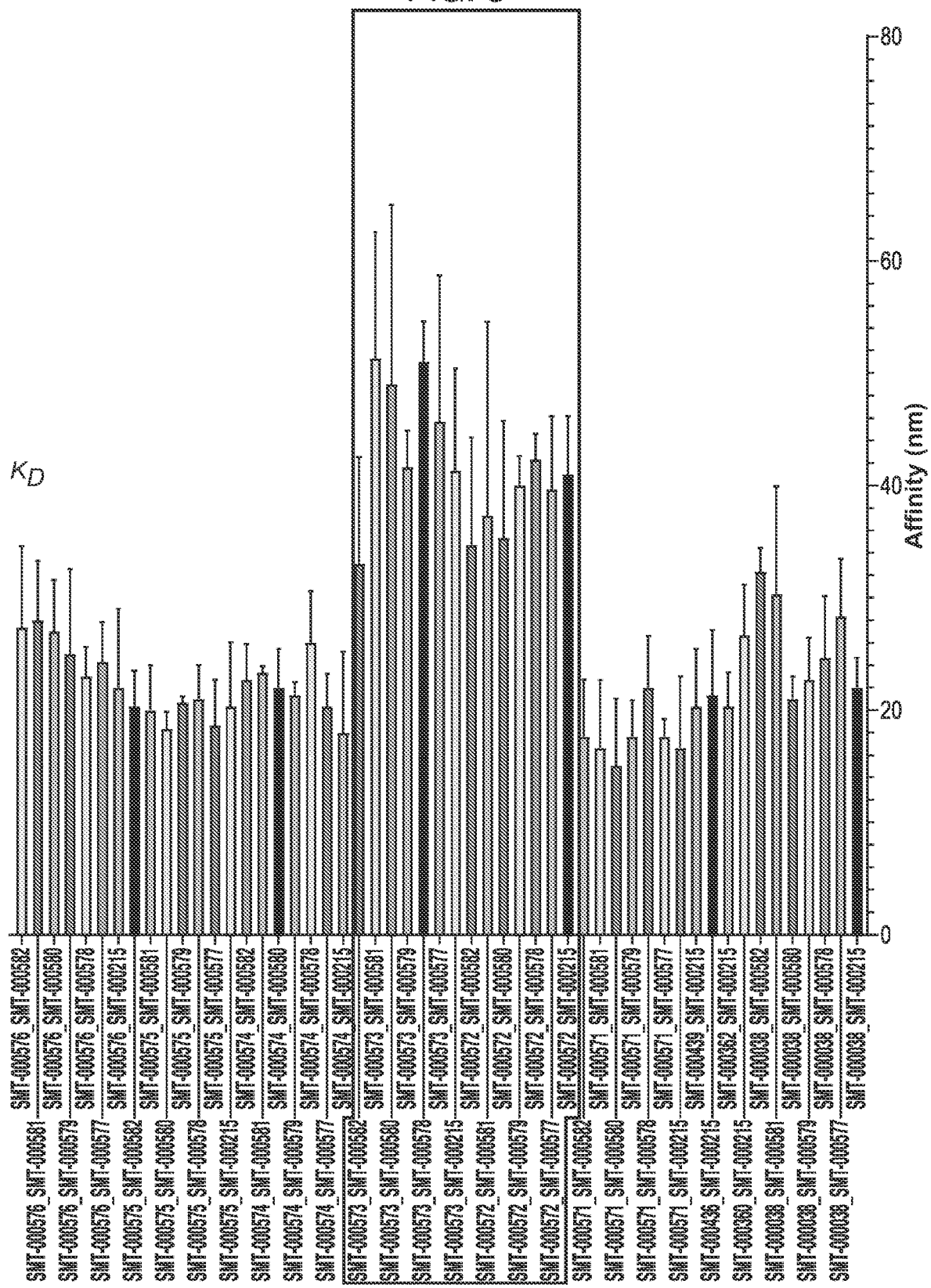
FIG. 3 is a graph showing the affinity for MSLN of various pairs of light chain and heavy chain variants of the anti-MSLN 1A12 antibody. Control MAb represents the anti-MSLN 1A12 antibody alone.

Pairs of LC/HC variants of the anti-MSLN 1A12 antibody, with CDRL3 or CDRH2 mutations to repair the predicted deamidation and isomerization sites, were assessed for changes in affinity compared to the control 1A12 antibody. These combinations yielded multiple pairwise solutions to improve antibody function and developability (FIG. 3). In particular, combinations including N92A or N92S resulted in a higher affinity ($K_D$) compared to control.

Example 2: Bispecific Antibodies

Bispecific IgG-scFv antigen-binding molecules that specifically bind MSLN and human CD3 were prepared in the structural format illustrated in FIG. 4, using the Fab domains of the 1A12 anti-MSLN antibody (see Table 1 above) and anti-CD3 variable domains of Micro194 (VH/VL=SEQ ID NOs. 57/58), a humanized version of the OKT3 antibody (VH/VL=SEQ ID NOs: 59/60), or a humanized version of the UCHT1 antibody (VH/VL=SEQ ID NOs: 61/62).

The methods for producing these molecules followed standard protein expression protocols that are described in various references. Briefly, the "Daedalus" human cell line expression platform was employed for the production and purification of secreted proteins. The expression system made use of suspension adapted HEK293 Freestyle cells and a highly optimized lentiviral transduction protocol to generate cell lines that secrete proteins at high levels. The lentiviral vector contained a cis-linked fluorescent protein reporter driven by an internal ribosome entry site (IRES) that allowed for tracking of relative protein expression levels. All mammalian proteins described were purified directly from conditioned media using HisTrap FF Crude columns (GE #17528601) and subsequently polished on a Superose 6 10/300 GL SEC column (GE #17517201) using an AKTA pure 25 instrument.

Figure 5A:
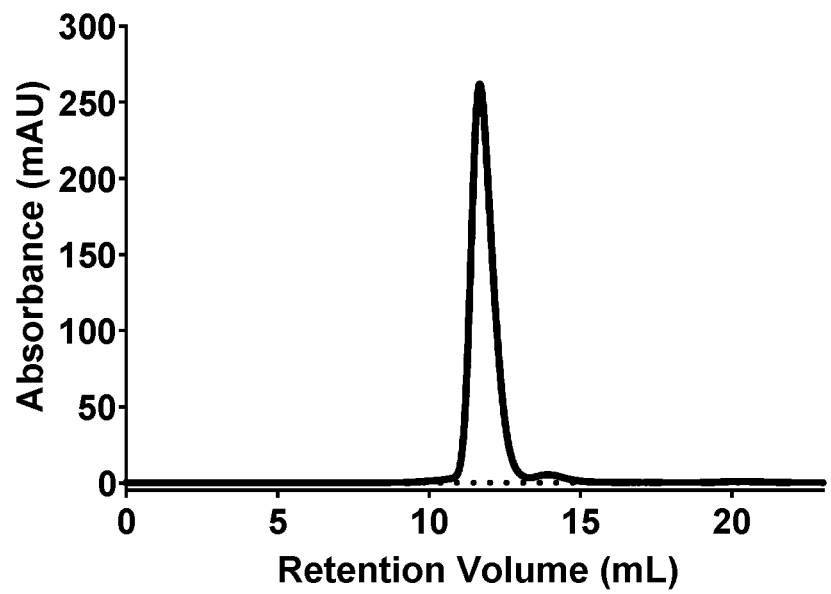
FIGS. 5A-5B are size exclusion chromatograms showing protein enrichment before (FIG. 5A) and after (FIG. 5B) Ni-NTA purification of a bispecific molecule comprising an anti-MSLN 1A12 binding domain and a humanized UCHT1 anti-CD3 scFv moiety, having the structure illustrated in FIG. 4.
Figure 5B:
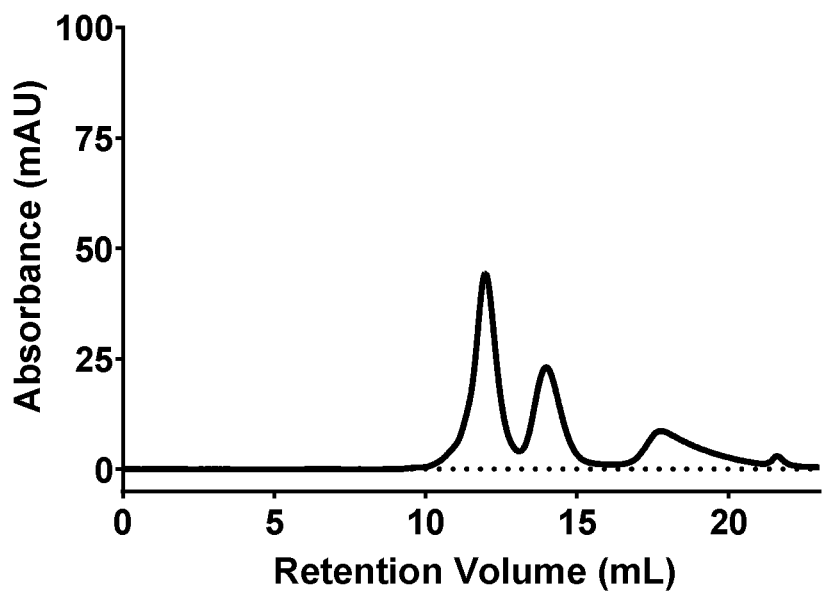
Figure 6A:
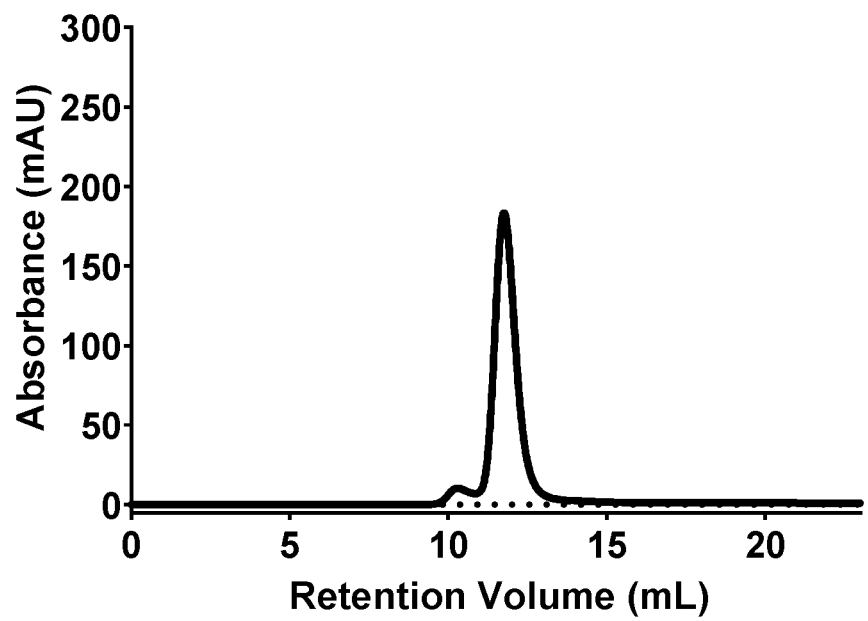
FIGS. 6A-6B are size exclusion chromatograms showing protein enrichment before (FIG. 6A) and after (FIG. 6B) Ni-NTA purification of a bispecific molecule comprising an anti-MSLN 1A12 binding domain and a Micro194 anti-CD3 scFv moiety, having the structure illustrated in FIG. 4.
Figure 6B:
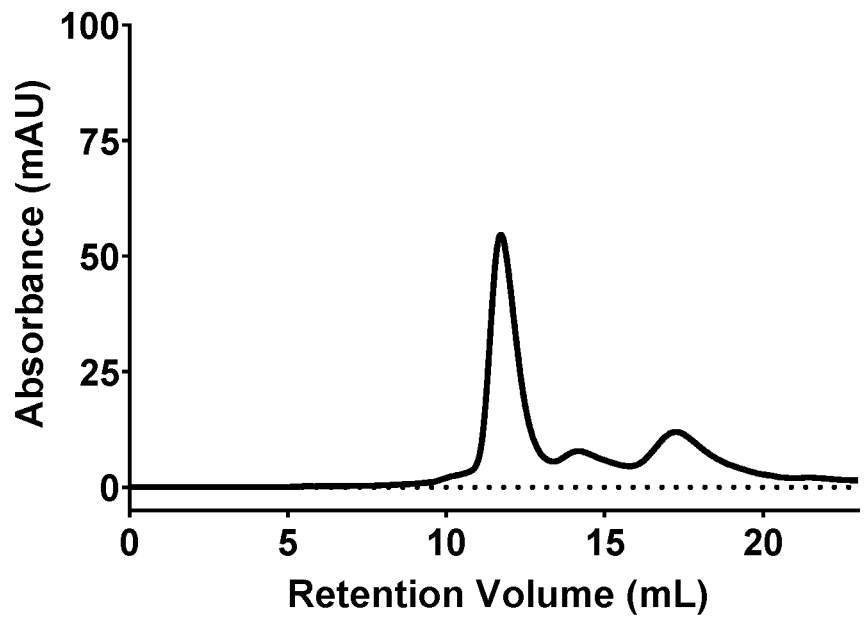

The bispecific antigen-binding molecules were purified and characterized using standard techniques. Representative chromatograms showing the purification of the IgG-scFv molecule with the structure of FIG. 4 are shown in FIGS. 5A-B (UCHT1 scFv) and 6A-B (Micro194 scFv), confirming successful production with minimal aggregates.

The affinity of bispecific IgG-scFv molecules for MSLN was assessed using the same methods as the anti-MSLN 1A12 variant antibodies described in Example 1.

Figure 7:
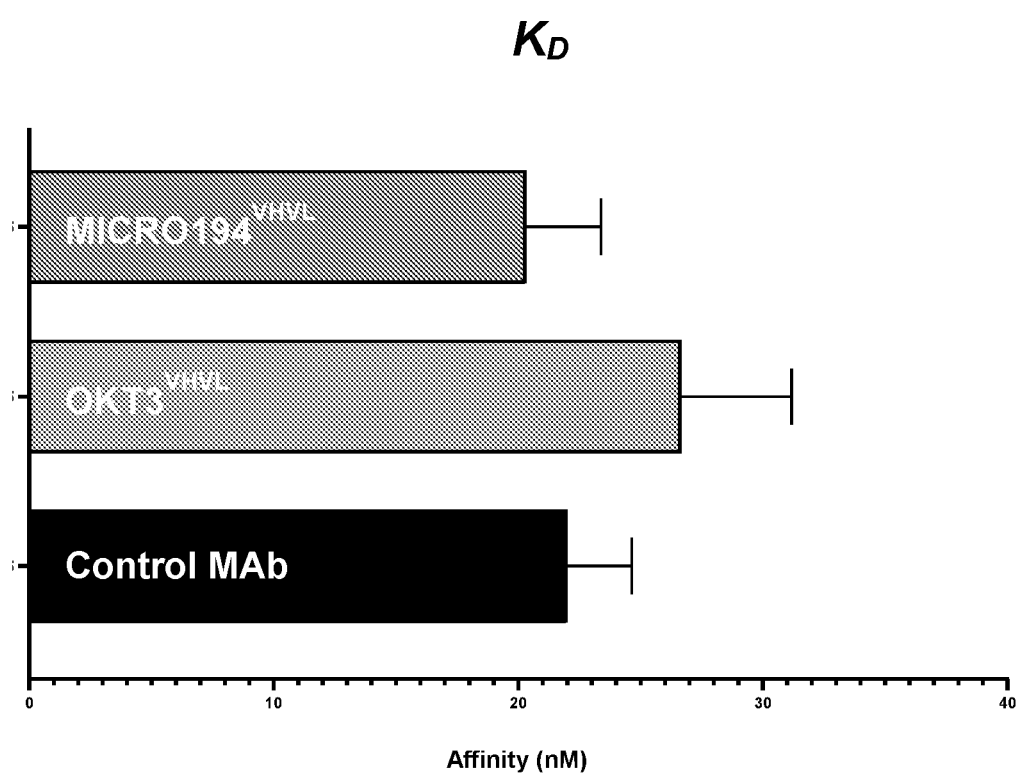
FIG. 7 is a graph showing the affinity for MSLN of bispecific molecules each comprising an anti-MSLN 1A12 binding domain and an anti-CD3 binding moiety as indicated, each having the structure illustrated in FIG. 4. Control MAb represents the anti-MSLN 1A12 antibody alone.

As shown in FIG. 7, fusing different CD3-engaging scFv moieties to the light chain of anti-MSLN 1A12 (SEQ ID NO: 10) did not affect affinity for MSLN.

Example 3: FACS-Based Cytotoxicity Assay to Assess T Cell-Mediated Killing of MSLN-Expressing Cells in the Presence of Anti-MSLN×Anti-CD3 Bispecific Molecules In order to monitor the specific killing of MSLN-expressing cells, cells with high surface expression of MSLN (SKOV3 and OVCAR3 ovarian carcinoma lines) were used in T cell killing assays. Briefly, a cytotoxicity assay was conducted using an automated platform programmed to simultaneously conduct unbiased 96 well assays in which 100,000 T cells (obtained from healthy donors, qualified by flow cytometry for CD3, CD28, CD4, CD8 pre- and post-EasySep™ no-touch purification) were mixed with 20,000 Luc-iRFP cancer cells (5:1 E:T ratio) in the presence or absence of 1A12:Micro194 or 1A12:OKT3 bispecific molecules (8 concentrations, ranging from 0-1 mg/ml). HPN536, a trispecific antibody that binds to MSLN, CD3, and serum albumin (also called TriTAC, see WO 2018/209304, the contents of which are incorporated by reference herein), was also assayed for comparison. Cytotoxicity was determined on day 5 for SKOV3 cells or day 2 for OVCAR3 cells after contacting the cells with the bispecific molecule.

Figure 8A:
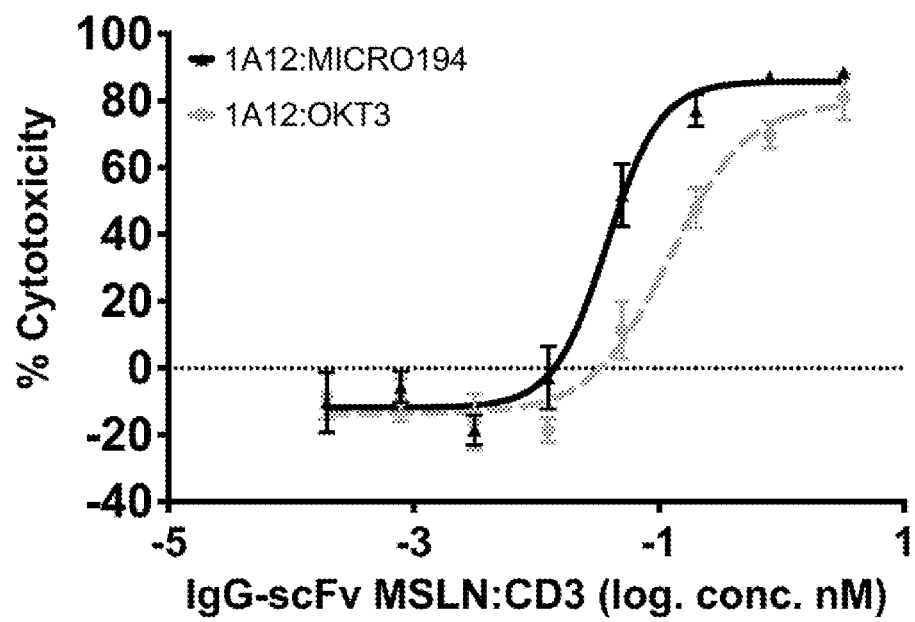
FIGS. 8A-8B are graphs showing the results of the ability of bispecific molecules each comprising an anti-MSLN 1A12 binding domain and an anti-CD3 binding moiety as indicated, each having the structure illustrated in FIG. 4, to induce cytotoxicity in SKOV3 (FIG. 8A) or OVCAR3 (FIG. 8B) human ovarian cancer cells. Cytotoxicity is reported as a percentage of dead cells as a function of the concentration of the bispecific molecule, determined on day 5 for SKOV3 cells or day 2 for OVCAR3 cells after contacting the cells with the bispecific molecule.
Figure 8A:
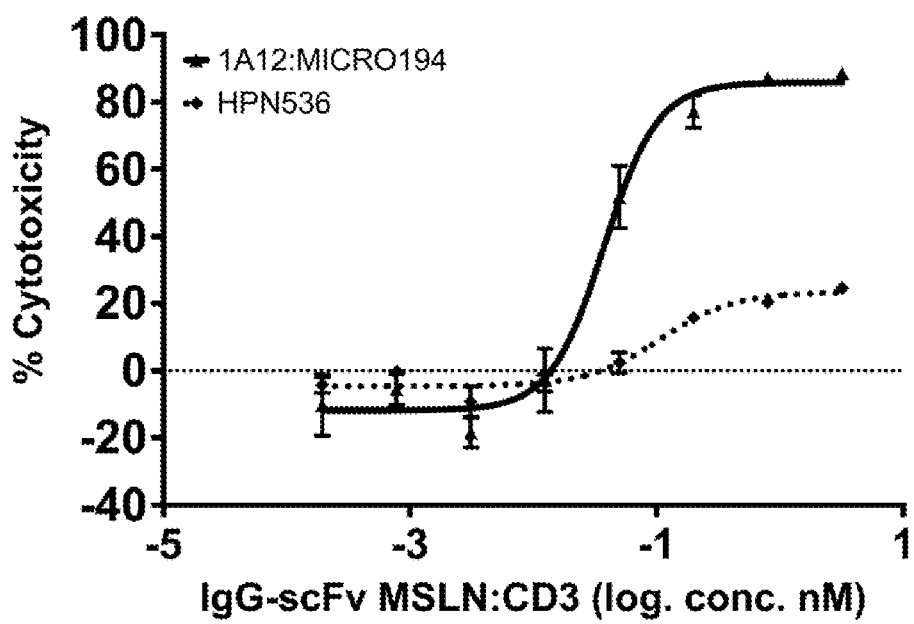
Figure 8B:
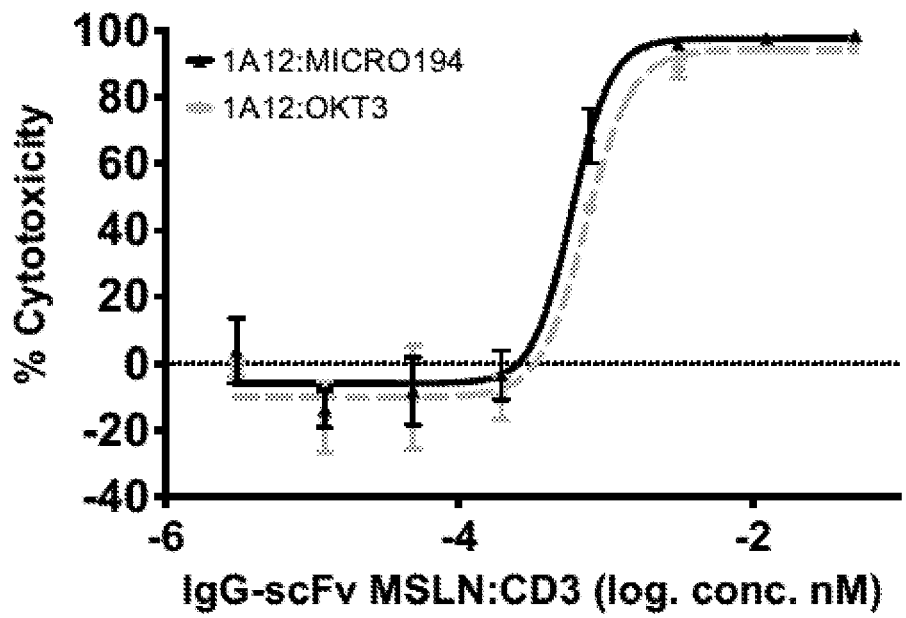
Figure 8B:
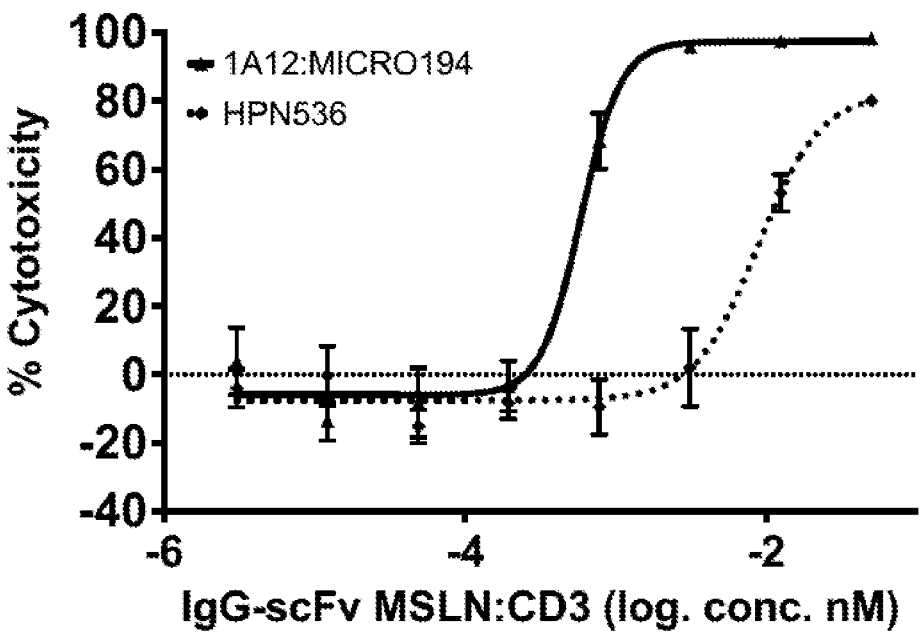

As shown in FIGS. 8A-8B, the 1A12:Micro194 molecule had a greater cytotoxic potency than the 1A12:OKT3 molecule with humanized OKT3 scFv, particularly against SKOV3 cells. The 1A12:Micro194 IgG-scFv molecule was considerably more potent than the HPN536 trispecific antibody against both types of MSLN-expressing cells.

Figure 9A:
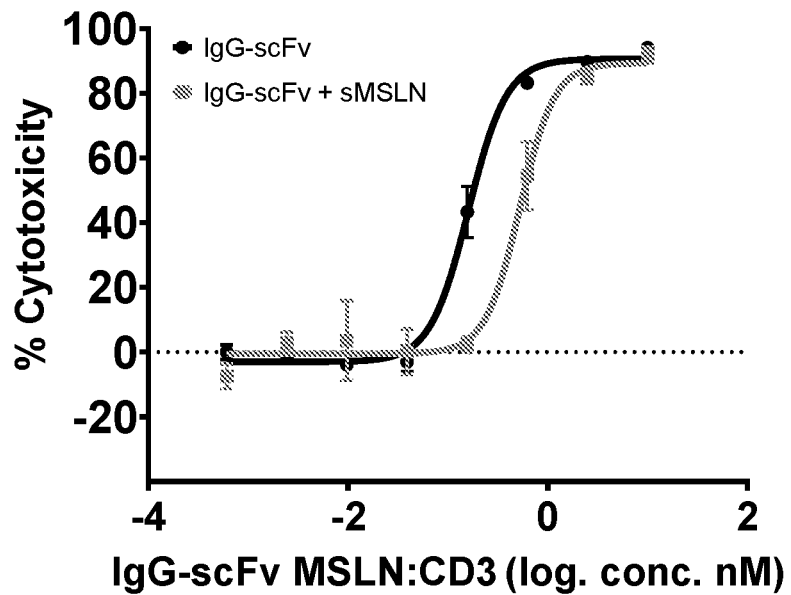
FIGS. 9A-9B are graphs showing the results of the ability of a bispecific molecule comprising an anti-MSLN 1A12 binding domain and an anti-CD3 binding moiety, having the structure illustrated in FIG. 4 (FIG. 9A), and the ability of a TriTAC molecule which binds MSLN, CD3 and serum albumin (FIG. 9B), to induce cytotoxicity in SKOV3 cells. The ability of the bispecific molecule and TriTAC molecule to induce cytotoxicity is challenged by soluble MSLN (TriTAC+sMSLN and IgG-scFv+sMSLN, respectively).
Figure 9B:
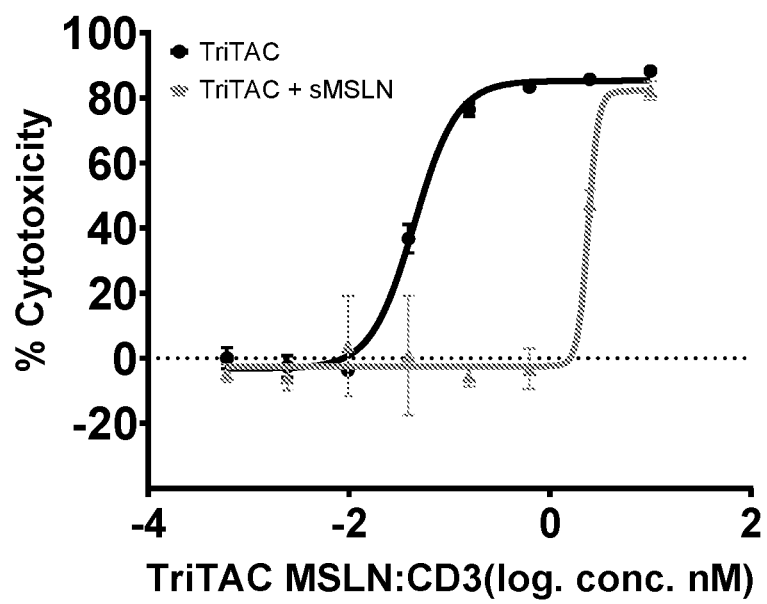

The ability of IgG-scFv and HPN536 (TriTAC) molecules to induce cytotoxicity in SKOV3 cells was compared in the presence or absence of soluble MSLN (sMSLN). As shown in FIG. 9A, cytotoxic potency of the IgG-scFv molecule decreased significantly in the presence of sMSLN. Without wishing to be bound by theory, the high affinity for both soluble MSLN-related proteins and cell surface MSLN leads the HPN536 molecule to be susceptible to the presence of sMSLN, decreasing cytotoxic potency. In contrast, the IgG-scFv molecule with the structure shown in FIG. 4 had high avidity for cell surface MSLN and low affinity for soluble MSLN-related proteins, and resulted in a smaller shift in cytotoxic potency (FIG. 9B).

Example 4: In Vivo Efficacy

Figure 10:
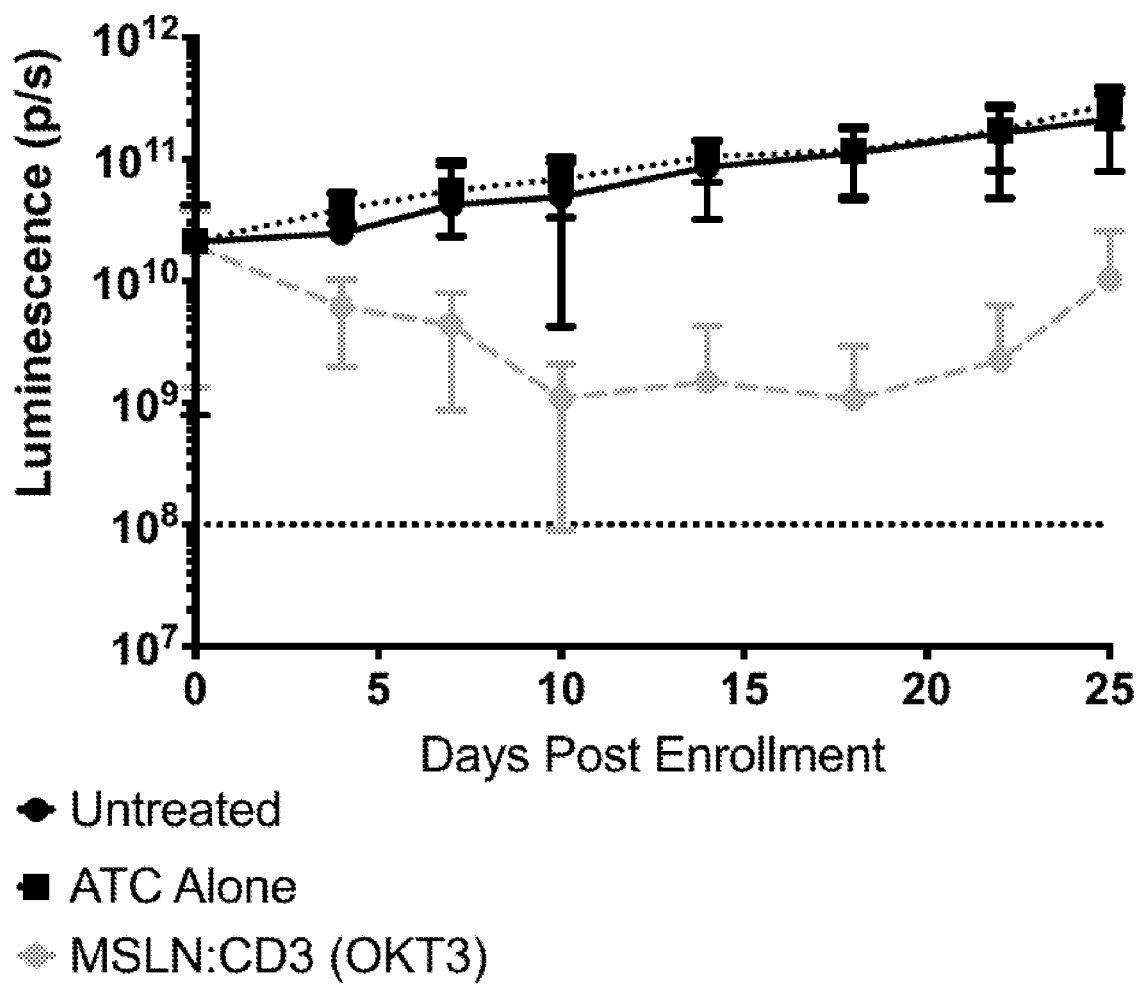
FIG. 10 is a graph showing the growth of tumors over time in NOD/SCID/IL-2R$\gamma$c$^{null}$ (NSG) mice engrafted intra-peritoneally with luciferase expressing SKOV3 cells, treated with a bispecific molecule comprising an anti-MSLN 1A12 binding domain and an anti-CD3 OKT3 binding moiety having the structure illustrated in FIG. 4. Untreated mice and mice treated with activated T cells (ATC) alone were used as controls. The y-axis is a measure of luminescence in photons per second (p/s) detected via bioluminescence imaging.

NOD/SCID/IL-2Rγc$^{null}$ (NSG) immunodeficient mice were engrafted intraperitoneally with luciferase-expressing SKOV3 cells. Mice were treated with the 1A12:OKT3 bispecific molecule comprising an anti-MSLN 1A12 binding domain and a humanized anti-CD3 OKT3 binding moiety. Untreated mice and mice treated with activated T cells (ATC) alone were used as controls. ATC were CD3+ Pan T cells isolated from peripheral blood mononuclear cells (PBMCs) and stimulated for rapid expansion. FIG. 10 shows that the 1A12:OKT3 bispecific molecule diminished the growth of tumors over time as compared to controls.

Example 5: Improved MSLN-CD3 Variants

Variants and Characteristics 24 unique variants of bispecific anti-MSLN/anti-CD3 IgG-scFv T cell engager molecules were prepared in the structural format illustrated in FIG. 4, using the Fab domains of the 1A12 anti-MSLN antibody or 1A12 variants described in Example 1 and Micro194 anti-CD3 scFv (see Table 2). These variants incorporated several different: (i) linker lengths between the VH and VL domains, (ii) light chain isomerization repairs, (iii) heavy chain deamination repairs, and (iv) effector function silencing solutions. The variant characteristics and results for expression and aggregation assays are shown below in Table 3.

The linker region separating the C-terminus of the light chain from the scFv (LC-Linker-scFv) is important for optimizing the potency of the bispecific T cell engager. The other important linker separates the variable domains of the scFv (VH-Linker-VL). Optimizing these linkers for length and flexibility was found to be important for function, manufacturing, and immunogenicity of the bispecific molecules. A novel glycine and serine containing linker was designed to maximize the flexibility of the linkage between both the light chain and the scFv and the variable domains of the scFv. The general architecture of this linker was GGGGS-(X)-SGGGG (SEQ ID NO: 85), where X is any combination of common flexible or rigid linker sequences (e.g., glycine-serine, proline-threonine, lysine-serine, human antibody hinge regions, etc.). Ultimately, the GGGGS-GGGSGGG-SGGGG (SEQ ID NO: 73) linker was determined to be the optimal length to prevent diabody formation.

Expression levels of the IgG-scFv molecules were assayed using either an analytical Protein A affinity chromatography titer assay, or a variable-pathlength slope spectroscopy SoloVPE A280 measurement, and applying a theoretical extinction coefficient for the protein at 1 mg/mL. The equation used to determine the molar extinction coefficient was $\varepsilon_{280}$=5500(# of Trp)+1490(# of Tyr)+125(# of S—S bonds). Size exclusion chromatography (SEC-HPLC) was used to separate IgG-scFv molecules based on differences in their hydrodynamic volumes. Protein samples were loaded onto a Waters XBridge Protein BEH SEC 200A column (3.5 µm, 7.8×300 mm) and equilibrated in 100 mM sodium phosphate, 250 mM sodium chloride, pH 6.8 running buffer. Purity was determined by calculating the percentage of each separated component as compared to the total integrated area.

IgG-scFv variants M-3643, M-3642, M-3648, M-3651, M-3654 and M-3641 (shown in bold in Table 3) had superior expression levels and minimal total aggregate compared to the other IgG-scFv molecules tested. Based on this data, these 6 variants were chosen to analyze further.

TABLE 3

IgG-scFv Variant Characteristics

| IgG-scFv | Variant Characteristics | | | | Expression | Stable Pools: | SEC |
| | Linker (scFv) | LC Isom Repair | HC Deam Repair | Fc Silencer | Expression (N297A versions) | Day 10 Titer (mg/mL) | Total Aggregate (%) |
|---|---|---|---|---|---|---|---|
| M-3643 | 17 | | | LEASPS | | 0.97 | 3.65 |
| M-3642 | 17 | | | LEPG | | 0.97 | 4.26 |
| M-3648 | 17 | N92K | D62E | LEPG | | 1 | 1.14 |
| M-3651 | 17 | S93V | D62E | LEPG | | 0.95 | 3.88 |
| M-3654 | 17 | N92K | D62S | LEPG | | 0.9 | 0.99 |
| M-3657 | 17 | S93V | D62S | LEPG | | 0.69 | 3.12 |
| M-3660 | 13 | N92K | D62E | LEPG | Low Expression | 0.01 | 62.71 |
| M-3641 | 17 | | | N297A | | 1.16 | 6.37 |
| | | | | | | Underlined = ~1 mg/mL | Underlined = >10% |

Thermal Hold

A thermal hold assay was performed to assess conformational stability of the IgG-scFv molecules. Samples were place in a 96-well Biorad PCR plate and heated to various temperatures from 69° C. to 74° C. for 5 minutes using a Biorad Thermal Cycler. After heating, protein precipitation was determined by reading the absorbance at 350 nm (A350) using an M5 plate reader. Results showed that M-3654 was more resistant to temperature denaturation (Table 4).

TABLE 4

Thermal Hold Assay

| | | Thermal Hold | | | | | | | |
| | | 69° C. | 69.4° C. | 70° C. | 71° C. | 72.2° C. | 73.2° C. | 73.7° C. | 74° C. |
|---|---|---|---|---|---|---|---|---|---|
| Standards | 1 | 0.17 | 0.20 | 0.20 | 0.17 | 0.18 | 0.23 | 0.41 | 0.45 |
| | 2 | 0.54 | 1.16 | 1.65 | 1.91 | 2.09 | 2.22 | 2.16 | 2.19 |
| | 3 | 0.17 | 0.22 | 0.63 | 1.84 | 2.09 | 2.21 | 2.21 | 2.19 |
| | 4 | 1.47 | 1.59 | 1.66 | 1.77 | 1.82 | 1.71 | 1.82 | 1.73 |
| Variant | M-3643 | 1.92 | 2.01 | 2.04 | 1.96 | 1.88 | 2.06 | 2.01 | 1.92 |
| | M-3642 | 1.41 | 1.68 | 1.89 | 1.93 | 2.07 | 2.09 | 1.81 | 1.86 |
| | M-3648 | 1.64 | 1.86 | 2.02 | 2.11 | 2.08 | 2.11 | 2.00 | 1.97 |
| | M-3651 | 2.04 | 2.08 | 2.02 | 2.03 | 2.05 | 2.13 | 1.93 | 1.90 |
| | M-3654 | 0.56 | 1.21 | 1.79 | 2.00 | 1.99 | 1.99 | 1.92 | 1.82 |
| | M-3657 | 1.85 | 2.04 | 2.13 | 2.08 | 2.03 | 1.96 | 1.92 | 1.91 |
| | M-3654 | 1.80 | 2.01 | 2.21 | 2.10 | 2.21 | 2.22 | 2.12 | 2.06 |

Chemical Unfolding

The inflection point of a chemical unfolding curve is thought to be related to conformational stability and stability during long-term storage, with a greater inflection point relating to a more structurally or conformationally stable molecule. A chemical unfolding curve was produced for each IgG-scFv molecule by exposing the molecule to increasing concentrations of the denaturant, guanidine hydrochloride. After 72 hours, the intrinsic fluorescence of the samples was measured using a SUPR-UV plate reader. The collected raw data was then processed, and the chemical unfolding curve and its inflection point calculated from the processed data as a function of denaturant condition.

M-3641 (an aglycosylated N297A mutant) was found to be less stable than variants incorporating other effector-silencing Fc mutations (Table 5).

TABLE 5

Chemical Unfolding

| | Inflection Pt 1 (M) | Std Dev IP1 |
|---|---|---|
| M-3643 | 2.055 | 0.018 |
| M-3642 | 2.088 | 0.005 |
| M-3648 | 2.107 | 0.008 |
| M-3651 | 2.115 | 0.001 |
| M-3654 | 2.104 | 0.007 |
| M-3657 | 2.142 | 0.017 |
| M-3641 | 1.862 | 0.071 |

Low pH Aggregation

The low pH aggregation assay can be used to help select candidates that are suitable for low pH viral inactivation. In this assay, samples comprising various IgG-scFv molecules were titrated to pH 3.3 using acetic acid and held for 30 minutes before being neutralized to pH 5 with tris base. The samples were characterized using SEC-HPLC as described above. Samples that were diluted with PBS using the same volume of acetic acid and tris base were used as a control. Molecules that demonstrated a significant increase in high molecular weight were considered unstable during low pH exposure, and in need of further method development if low pH viral inactivation were to be used.

Of all variants tested in this low pH aggregation assay, M-3654 was the most stable at low pH (suggesting that the repair mutations improved the behavior of this molecule), and M-3641 was the least stable (Table 6).

TABLE 6

Low pH Hold

Low pH

| | Low pH HMW Rep 1 | Low pH HMW Rep 2 | % HMW Low pH control | Low pH – Control |
|---|---|---|---|---|
| M-3643 | 3.32 | 3.35 | 2.14 | 1.20 |
| M-3642 | 3.46 | 3.61 | 2.38 | 1.16 |
| M-3648 | 1.61 | 1.71 | 1.83 | -0.17 |
| M-3651 | 3.57 | 3.92 | 1.08 | 2.67 |
| M-3654 | 1.37 | 1.55 | 1.42 | 0.04 |
| M-3657 | 2.96 | 3.14 | 1.72 | 1.33 |
| M-3641 | 10.08 | 9.98 | 3.55 | 6.48 |

Product Quality

SEC and non-reduced (NR) and reduced (R) capillary electrophoresis sodium dodecyl sulfate (CE-SDS) showed that the M-3654 IgG-scFv molecule had low levels of high molecular weight and low molecular weight contaminant species (Table 7). rCE-SDS under denaturing and reducing conditions also demonstrated the clean separation of the heavy and light chains of M-3654, indicating that M-3654 behaves as expected for an antibody, even with isomerization and deamination sites mutated.

TABLE 7

Product quality

| M-3654 | Conditions | LMW | HMW/ Post Main | Main Peak |
|---|---|---|---|---|
| SEC | Native | 2.6% | 1% | 96.4% |
| rCE-SDS | Denaturing and Reducing | 0.8% | 1.7% | 97.4% |
| nrCE-SDS | Denaturing | 17.9% | 0% | 82.2% |

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entireties and for all purposes to the same extent as if each individual reference (e.g., publication or patent or patent application) was specifically and individually indicated to be incorporated by reference in its entirety for all purposes.

Other embodiments are within the following claims.

What is claimed:

1. An isolated antibody molecule that specifically binds human MSLN, the antibody molecule comprising: a VH comprising CDRs CDRH1, CDRH2, and CDRH3; and a VL comprising CDRs CDRL1, CDRL2, and CDRL3, wherein CDRH1, CDRH2, CDRH3, CDRL1, CDRL2, and CDRL3 comprise the amino acid sequences set forth in SEQ ID NOs: 3, 30, 5, 6, 7, and 35, respectively.

2. The isolated antibody molecule of claim 1, wherein the VH comprises the amino acid sequence set forth in SEQ ID NO: 18; and/or the VL comprises the amino acid sequence set forth in SEQ ID NO: 23.

3. The isolated antibody molecule of claim 1, wherein the VH and VL comprise the amino acid sequences set forth in SEQ ID NOs: 18 and 23, respectively.

4. The isolated antibody molecule of claim 1, wherein the antibody comprises a heavy chain constant region selected from the group consisting of human IgG$_1$, human IgG$_2$, human IgG$_3$, human IgG$_4$, human IgA$_1$, and human IgA$_2$.

5. The isolated antibody molecule of claim 4, wherein the heavy chain constant region:
   (a) comprises the amino acid sequence set forth in SEQ ID NO: 53, 54, 55, 56, or 72; and/or
   (b) is a variant of a wild-type heavy chain constant region, wherein the variant heavy chain constant region binds to an FcγR with lower affinity than the wild-type heavy chain constant region binds to the FcγR.

6. The isolated antibody molecule of claim 1, wherein the antibody molecule comprises: a heavy chain comprising the amino acid sequence set forth in SEQ ID NO: 83 or 84; and/or a light chain comprising the amino acid sequence set forth in SEQ ID NO: 47.

7. The isolated antibody molecule of claim 6, wherein the heavy chain and light chain comprise the amino acid sequences set forth in SEQ ID NOs: 83 and 47, respectively.

8. The isolated antibody molecule of claim 1, further comprising a CD3 binding moiety.

9. The isolated antibody molecule of claim 8, wherein:
   (a) the CD3 binding moiety is an antibody; or
   (b) the CD3 binding moiety is a single-chain fragment variable (scFv).

10. The isolated antibody molecule of claim 9, wherein the scFv comprises the amino acid sequence set forth in SEQ ID NO: 76.

11. The isolated antibody molecule of claim 9, wherein the CD3 binding moiety is covalently linked to the light chain.

12. The isolated antibody molecule of claim 11, wherein the CD3 binding moiety is covalently linked to the C-terminus of the light chain via a peptide linker, optionally wherein the peptide linker comprises the amino acid sequence set forth in SEQ ID NO: 63, 64, 73, 74, or 75.

13. The isolated antibody molecule of claim 12, wherein the light chain comprises the amino acid sequence set forth in SEQ ID NO: 77.

14. An isolated antibody molecule that specifically binds human MSLN, the antibody molecule comprising a heavy chain and a light chain comprising the amino acid sequences, set forth in:
   (a) SEQ ID NOs: 83 and 47, respectively; or
   (b) SEQ ID NOs: 84 and 47, respectively.

15. The isolated antibody molecule of claim 14, further comprising a CD3 binding moiety.

16. The isolated antibody molecule of claim 15, wherein:
   (a) the CD3 binding moiety is an antibody; or
   (b) the CD3 binding moiety is a single-chain fragment variable (scFv).

17. The isolated antibody molecule of claim 16, wherein the scFv comprises the amino acid sequence set forth in SEQ ID NO: 76.

18. The isolated antibody molecule of claim 15, wherein the CD3 binding moiety is covalently linked to the light chain.

19. The isolated antibody molecule of claim 15, wherein the CD3 binding moiety is covalently linked to the C-terminus of the light chain via a peptide linker, optionally wherein the peptide linker comprises the amino acid sequence set forth in SEQ ID NO: 63, 64, 73, 74, or 75.

20. The isolated antibody molecule of claim 19, wherein the light chain comprises the amino acid sequence set forth in SEQ ID NO: 77.

21. The isolated antibody molecule of claim 14, wherein the heavy chain and the light chain comprise the amino acid sequences set forth in SEQ ID NOs: 83 and 77, respectively.

22. The isolated antibody molecule of claim 1, wherein the antibody molecule is conjugated to a cytotoxic agent, cytostatic agent, toxin, radionuclide, or detectable label.

23. The isolated antibody molecule of claim 14, wherein the antibody molecule is conjugated to a cytotoxic agent, cytostatic agent, toxin, radionuclide, or detectable label.

24. A composition comprising the antibody molecule of claim 1 and a pharmaceutically acceptable carrier or pharmaceutically acceptable excipient.

25. A composition comprising the antibody molecule of claim 14 and a pharmaceutically acceptable carrier or pharmaceutically acceptable excipient.

26. A composition comprising the antibody molecule of claim 21 and a pharmaceutically acceptable carrier or pharmaceutically acceptable excipient.

* * * * *